United States Patent
Turon Dols et al.

(10) Patent No.: US 11,884,542 B2
(45) Date of Patent: Jan. 30, 2024

(54) PERMANENTLY POLARIZED HYDROXYAPATITE, A PROCESS FOR ITS MANUFACTURE AND USES THEREOF

(71) Applicants: B. BRAUN SURGICAL, S.A., Rubí (ES); UNIVERSITAT POLITÉCNICA DE CATALUNYA, Barcelona (ES)

(72) Inventors: Pau Turon Dols, Rubí (ES); Luis Javier Del Valle Mendoza, Barcelona (ES); Jordi Puiggalí Bellalta, Barcelona (ES); Carlos Enrique Alemán Llansó, Barcelona (ES)

(73) Assignees: B. BRAUN SURGICAL, S.A., Rubí (ES); UNIVERSITAT POLITÉCNICA DE CATALUNYA, Barcelona (ES)

( * ) Notice: Subject to any disclaimer, the term of this patent is extended or adjusted under 35 U.S.C. 154(b) by 1379 days.

(21) Appl. No.: 16/322,195

(22) PCT Filed: Aug. 1, 2017

(86) PCT No.: PCT/EP2017/069437
§ 371 (c)(1),
(2) Date: Jan. 31, 2019

(87) PCT Pub. No.: WO2018/024727
PCT Pub. Date: Feb. 8, 2018

(65) Prior Publication Data
US 2020/0180960 A1 Jun. 11, 2020

(30) Foreign Application Priority Data

Aug. 2, 2016 (EP) ..................... 16382381
Nov. 11, 2016 (EP) ..................... 16382524

(51) Int. Cl.
*A61K 47/02* (2006.01)
*A61L 24/02* (2006.01)
*A61L 27/12* (2006.01)
*C01B 25/32* (2006.01)
*B01J 20/04* (2006.01)
*B01J 27/18* (2006.01)
*B01J 35/00* (2006.01)
*C08K 3/32* (2006.01)
*H01M 10/0562* (2010.01)

(52) U.S. Cl.
CPC ............ *C01B 25/327* (2013.01); *A61K 47/02* (2013.01); *A61L 24/02* (2013.01); *A61L 27/12* (2013.01); *B01J 20/048* (2013.01); *B01J 27/1806* (2013.01); *B01J 35/0033* (2013.01); *C08K 3/32* (2013.01); *H01M 10/0562* (2013.01); *C01P 2002/72* (2013.01); *C01P 2002/85* (2013.01); *C01P 2004/03* (2013.01); *C01P 2006/40* (2013.01); *C08K 2003/325* (2013.01); *H01M 2300/0068* (2013.01)

(58) Field of Classification Search
CPC ....... A61K 47/02; C01B 25/327; A61L 24/02; A61L 27/12
See application file for complete search history.

(56) References Cited

U.S. PATENT DOCUMENTS

2017/0173213 A1* 6/2017 Yates .................. C25D 9/04

OTHER PUBLICATIONS

Jerry C.C. Chan et al. Solid-state P-31 NMR study of octacalcium phosphate incorporated with succinate, Phy Chem Chem Phy, 12, 6692-6697. (Year: 2010).*
Jerry C.C. Chan et al. Solid-State NMR Study of the Transformation of Octacalcium Phosphate to Hydroxyapatite: A Mechanistic Model for Central Dark Line Formation, JACS, 128, 6909-6918. (Year: 2006).*
Amir Hossein Rajabi e tal. Piezoelectric materials for tissue regeneration: A review, Acta Biomaterialia, 24, 12-23. (Year: 2015).*
Dawnielle Farrar et al. Permanent polarity and piezoelectircity of electrospun alpha-helical poly(alpha-aminoacid) bibers, Advanced materials,21,3954-3958. (Year: 2011).*
Yao-Hung Tseng et al. Solid-state NMR study of the transformation of octacalcium phosphate to hydroxyapatite: A mechanistic model for central dark line formation, JACS, 128, 6909-6918. (Year: 2006).*
PCT International Search Report and Written Opinion completed by the ISA/EP on Oct. 6, 2017 and issued in connection with PCT/EP2017/069437.
Kobayashi, T., et al. "Enhanced osteobonding by negative surface charges of electrically polarized hydroxyapatite" Journal of Biomedical Materials Research, Dec. 15, 2001, pp. 477-484.
Horiuchi, N., et al. "Proton conduction related electrical dipole and space charge polarization in hydroxyapatite" Journal of Applied Physics, American Institute of Physics, US, vol. 112, No. 7, Oct. 1, 2012, pp. 74901-74901.
Yu, et al. "Local structure of hydroxy-peroxy apatite: A combined XRD, FT-IR, Raman, SEM, and solid-state NMR study" Journal of Physics and Chemistry of Solids, Pergamon Press, London GB, vol. 68, No. 10, Oct. 1, 2007, pp. 1863-1871.
Nakamura, M., et al. "Role of blood coagulation components as intermediators of high osteoconductivity of electrically polarized hydroxyapatite", Journal of Biomedical Materials Research, Part A, vol. 79A, No. 3, Dec. 1, 2006, pp. 627-634.
Gittings, et al. "Characterisation of ferroelectric-calcium phosphate composites and ceramics", Journal of The European Ceramic Society, Elsevier Science Publishers, Barking, Essex, GB, vol. 27, No. 13-15, Jan. 2007, pp. 4187-4190.
Ueshima, M., et al. "Electrovectorial effect of Polarized Hydroxyapatite on Quasi-Epitaxial Growth at Nano-Interfaces", Solid State Ionics, North Holland Pub. Company, Amsterdam, NL, NL, vol. 151, No. 1-4, Nov. 1, 2002, pp. 29-34.
Tofail, S., et al. "Electro-thermal Polarisation of Hydroxyapatite Ceramics and Coatings for Bone Tissue Engineering Applications" in "Electrically Active Materials for Medical Devices", 2016, Imperial College Press, London, pp. 115-134.

* cited by examiner

*Primary Examiner* — Michael G. Hartley
*Assistant Examiner* — Jagadishwar R Samala
(74) *Attorney, Agent, or Firm* — Barnes & Thornburg LLP

(57) ABSTRACT

The present invention relates to a permanently polarized hydroxyapatite and a composition or material comprising thereof. The present invention further relates to a process for obtaining a permanently polarized hydroxyapatite and to different uses of the permanently polarized hydroxyapatite or the composition or material comprising thereof.

19 Claims, 33 Drawing Sheets

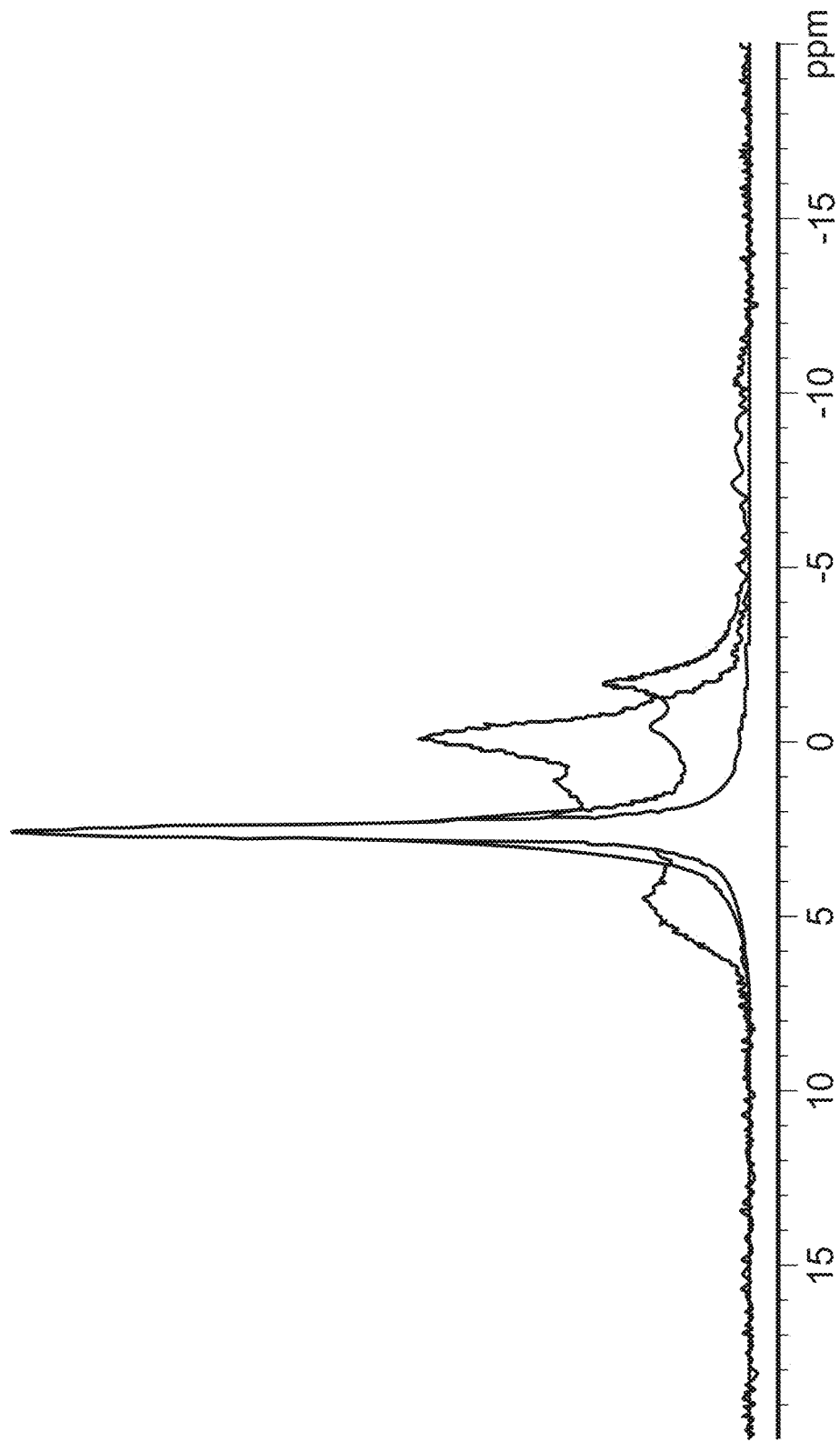

SAMPLES AS PREPARED

| System | Electrical resistance ($\Omega \cdot cm^2$) | Surface capacitance ($\mu F/g$) |
|---|---|---|
| cHAp/tsp | $0.67 \cdot 10^6$ | $386 \pm 16$ |
| Nakamura et al. 300 °C | $0.45 \cdot 10^7$ | $136 \pm 14$ |
| Nakamura et al. 800 °C | $0.37 \cdot 10^7$ | $173 \pm 27$ |
| Ueshima et al. (300 °C) | $0.39 \cdot 10^7$ | $153 \pm 15$ |
| Ueshima et al. (850 °C) | $0.29 \cdot 10^7$ | $249 \pm 9$ |

Figure 27

RE-EVALUATION OF THE SAME SAMPLES AFTER 3 MONTHS

| System | Electrical resistance ($\Omega \cdot cm^2$) | Surface capacitance ($\mu F/g$) |
|---|---|---|
| cHAp/tsp | $0.73 \cdot 10^6$ | $356 \pm 7$ |
| Nakamura et al. 300 °C | $0.76 \cdot 10^7$ | $49 \pm 9$ |
| Nakamura et al. 800 °C | $0.59 \cdot 10^7$ | $71 \pm 12$ |
| Ueshima et al. (300 °C) | $0.63 \cdot 10^7$ | $58 \pm 9$ |
| Ueshima et al. (850 °C) | $0.47 \cdot 10^7$ | $94 \pm 12$ |

Figure 29

PERMANENTLY POLARIZED HYDROXYAPATITE, A PROCESS FOR ITS MANUFACTURE AND USES THEREOF

CROSS-REFERENCE TO RELATED APPLICATIONS

This application is a U.S. national counterpart application of international application serial No. PCT/EP2017/069437, filed Aug. 1, 2017, which claims priority to European Patent Application Nos. 16382381.8 filed Aug. 2, 2016 and European Patent Application No. 16382524.3 filed Nov. 11, 2016.

FIELD OF THE INVENTION

The present invention relates to a permanently polarized hydroxyapatite, a process for manufacturing said permanently polarized hydroxyapatite and uses thereof.

BACKGROUND OF THE INVENTION

Hydroxyapatite (HAp), $Ca_{10}(PO_4)_6(OH)_2$, is the major inorganic component of biological hard tissues such as bone and tooth.[1,2] Synthetic HAp, which shows excellent ability to interact with living systems, has been investigated for biomedical applications, as for example drug and gene delivery, tissue engineering and bone repair.[3-8]

An important difference between amorphous calcium phosphate (ACP) and crystalline synthetic HAp (cHAp) is the alignment of the OH⁻ ions along the c-axis in the latter. The crystal structure of stoichiometric cHAp, which contains no OH⁻ defects, is monoclinic at room temperature.[9,10] The monoclinic cHAp changes to hexagonal phase at about 210° C., which means a change from an ordered to a disordered distribution of OH⁻ ions along the c-axis. In addition to thermal phase transition, OH⁻ defects also cause a phase transition.[9,10] In this case, the hexagonal phase becomes the most stable form of cHAp in the pH range of 4-12 because of the disorder caused by the presence of vacancies and presence of oxygen radicals in the columns of OH⁻ groups. Although electrical and dielectric properties of cHAp were found to be altered by thermally-induced changes in the positions of OH⁻ ions,[11-13] the observed polarization effects were not stable at room temperature (i.e. the OH⁻ re-reorientation has a short relaxation time).

Yamashita and co-workers[14,15] provoked quasi-permanent polarization effects in the polycrystalline HAp samples by applying a constant DC electric field of 1.0-4.0 kV/cm to samples sintered previously at 1250° C. for 2 h. This approach is based on a constant electric field at a temperature <700° C. The maximum current density (~$10^{-9}$ A/cm²) determined by thermally stimulated depolarization current (TSDC) measurements was obtained when the temperature in the polarization step was fixed at 400° C. Indeed, the current density was observed to decrease rapidly when the polarization temperature was higher than 450° C. Results indicated that the polarization was consequence of the electrical dipoles associated to the formation of defects inside crystal grains and of the space charge polarization originated in the grain boundaries. The thermally stimulated polarization process was found to exert different effects on the HAp surface properties.[16,17] Although the influence of polarization exhibited no effect on the surface roughness, crystallinity and constituent elements of cHAp, the wettability[16] and adhesion of osteoblastic cells is higher onto polarized samples than onto as prepared ones.[17] The latter phenomena were attributed to the increase in the surface free energies in comparison with non-polarized cHAp surfaces.

In this sense, document ES2323628 discloses that calcium hydroxyapatite in solid solution is obtained by sintering the prepared powder by a given method at 1200° C. for 1-5 hours. The ceramic material can be polarized at a T higher than 1000° C. or at a constant electric field higher than 100.000 V/cm. Nevertheless, the energy is not stored in such conditions and accordingly it is better to work under 1000° C. or a voltage between 10 and 100.000 V/cm.

Fu, Cong et al. discloses in "Hydroxyapatite thin films with giant electrical polarization", Chemistry of Materials (2015) 27(4), 1164-1171, that carbonated hydroxyapatite formed on titanium and stainless steel electrodes and further hydrothermal crystallization at 200° C. using a solution that contains 0.3 M of urea was found to display polarization with a stored charge in excess of 66.000 microcoulombs per square centimeter. In addition, this exhibited polarization on carbonated hydroxyapatite depends on the temperature and is not permanent. In contrast, the present invention does not disclose carbonated hydroxyapatite and the goal is to obtain a permanent polarization.

Recently, the present inventors examined the capacity of prepared ACP and cHAp to interact with different phosphates and a biophosphonate (BPs),[18] which is a very relevant topic in the field of biomaterials for biomedical applications. Thus, polyphosphate (polyP), which is an orthophosphate polymer found in mammalian organisms,[19] promotes bone regeneration when adsorbed onto HAp.[20-24] Specifically, polyP stabilizes basic cell growth and differentiation enhancing bone regeneration.[25-27] Further, other studies reported that polyP and pyrophosphate ($P_2O_7^{4-}$) inhibit HAp crystal growth.[28,29] More recently, Grynpas and coworkers[30] proposed that the production of polyP plays an important role in cartilage mineralization and bone formation, which was attributed to the local accumulation of phosphate ($PO_4^{3-}$) and calcium ($Ca^{2+}$) through the formation of strong complexes. This hypothesis was supported by both the adsorption of polyP onto HAp and the correlation between the hydrolytic correlation of polyP in $Ca^{2+}$-polyP complexes and the increment of $PO_4^{3-}$ and $Ca^{2+}$ concentrations. On the other hand, in BPs the oxygen atom that links the phosphate groups of pyrophosphates is replaced by a carbon atom, which results in the inhibition of both hydrolytic and enzymatic degradations.[31] The affinity of BPs towards HAp increases by incorporating amino functionalities to the tertiary carbon atom, which has been associated to the formation of strong hydrogen bonds between the two species.[32,33] Furthermore, BPs are primary agents in the current pharmacological arsenal against different bone diseases (e.g. osteoporosis, Paget disease of bone and malignancies metastatic to bone).[34]

Recent observations evidenced that the adsorption of polyP and $P_2O_7^{4-}$ onto as prepared ACP and cHAp is favored at pH 7 with respect to basic pH 9, even though some limitations in the association processes were found when the results obtained using different adsorbate concentrations were compared.[18] Studies on the adsorption of amino-tris(methylenephosphonic acid), hereafter denoted ATMP, suggested that the affinity of ACP and cHAp towards this BP is lower than towards polyP and $P_2O_7^{4-}$.[18]

M. Ueshima, S. Nakamura, M. Oghaki, K. Yamashita, Solid State Ionics 2002, 151, 29-34[63] disclose the polarization of bioactive (HAp) materials by preparing HAp powders via a precipitations reaction, then uniaxially pressing the powders into pellets and sintering those at 1250° C. for 2 h under a water vapor stream. The obtained specimens are sandwiched between Pt electrodes, heated to room temperature, 300° C. and 800° C. in air, respectively, and then subjected to electrical polarization treatment in DC fields of 1 and 10 kV/cm for 1 h and thereafter cooled to room temperature under polarization.

M. Nakamura, Y. Sekijima, S. Nakamura, T. Kobayashi, K. Niwa, K. Yamashita, *J. Biomed. Mater. Res.* 2006, 79A, 627-634[62] disclose the preparation of polarized HAp samples as shown in the material and methods section wherein, in particular, the sinterization is carried out in saturated water vapor atmosphere at 1250° C. for 2 hours and the samples are electrically polarized in a DC. field of 1.0 kV cm$^{-1}$ with a pair of platinum electrodes in air at 300° C. for 1 h. Said polarized HAp are implanted into the tibia of rats in order to detect the interactions between the implanted HAp and blood coagulation components. The mechanism of the enhanced osteoconductivity caused by electrical polarization is also discussed.

Accordingly, in view of above, the present inventors have surprisingly found that it is possible to obtain a permanently polarized hydroxyapatite with specific electrochemical and electrical properties associated with a huge range of possibilities of use as disclosed below.

SUMMARY OF THE INVENTION

A first aspect of the present invention relates to a permanently polarized hydroxyapatite and a composition or material comprising thereof.

A second aspect of the present invention relates to a process for obtaining a permanently polarized hydroxyapatite.

A third aspect of the present invention relates to another process for obtaining a permanently polarized hydroxyapatite.

A fourth aspect of the present invention relates to a permanently polarized hydroxyapatite obtained or obtainable by a process according to the second or third aspect of the present invention.

A fifth aspect of the present invention relates to different uses of the permanently polarized hydroxyapatite.

BRIEF DESCRIPTION OF THE DRAWINGS

FIG. 18A-D. FIG. 18A shows the $^{31}P$ spectrum of HAp sample as obtained by synthesis (cHAp/p) where the co-existence of crystalline and disordered phase(s) (amorphous calcium phosphate) is present. The crystallinity is 43%. Weak signals are probably due to hydrogenphosphate and dihydrogenphosphate. FIG. 18B shows the $^{31}P$ spectrum of sintered HAp sample (cHAp/s) where a re-organization is observed. The co-existence of several crystalline and disordered phase(s) (amorphous calcium phosphate) is also present. The crystallinity is 65%. Weak signals are probably due to hydrogenphosphate and dihydrogenphosphate. FIG. 18C shows the $^{31}P$ spectrum of HAp sample after permanent polarization according to the present invention (cHAp/tsp) where the crystallinity is 76%. Weak signals are no longer present. FIG. 18D shows the overlapping of spectra from FIGS. 18A-C.

FIG. 27. Comparative table between the system of the present invention and those of state of the art with respect to the electrical resistance and surface capacitance with the following conditions with samples as prepared:
Conditions of Nakamura et al. (J. Biomed. Mater. Res. 2006, 79A, 627-634):
i) Synthesis by precipitation at room temperature;
ii) Drying at 850° C. for 2 h
iii) Calcination at 1250° C. in saturated water atmosphere for 2 h
iv) Polarization at 1 kV/cm for 1 h at 300 or 800° C.
Conditions of Ueshima et al. (Solid State Ionics 2002, 151, 29-34):
i) Synthesis by precipitation at room temperature;
ii) Drying at 850° C. for 2 h
iii) Calcination at 1250° C. in saturated water atmosphere for 2 h
iv) Polarization at 10 kV/cm for 1 h at 300 or 850° C.

FIG. 29. Re-evaluation of the samples as in FIG. 27 after 3 months.

DETAILED DESCRIPTION OF THE INVENTION

Figure 18A:
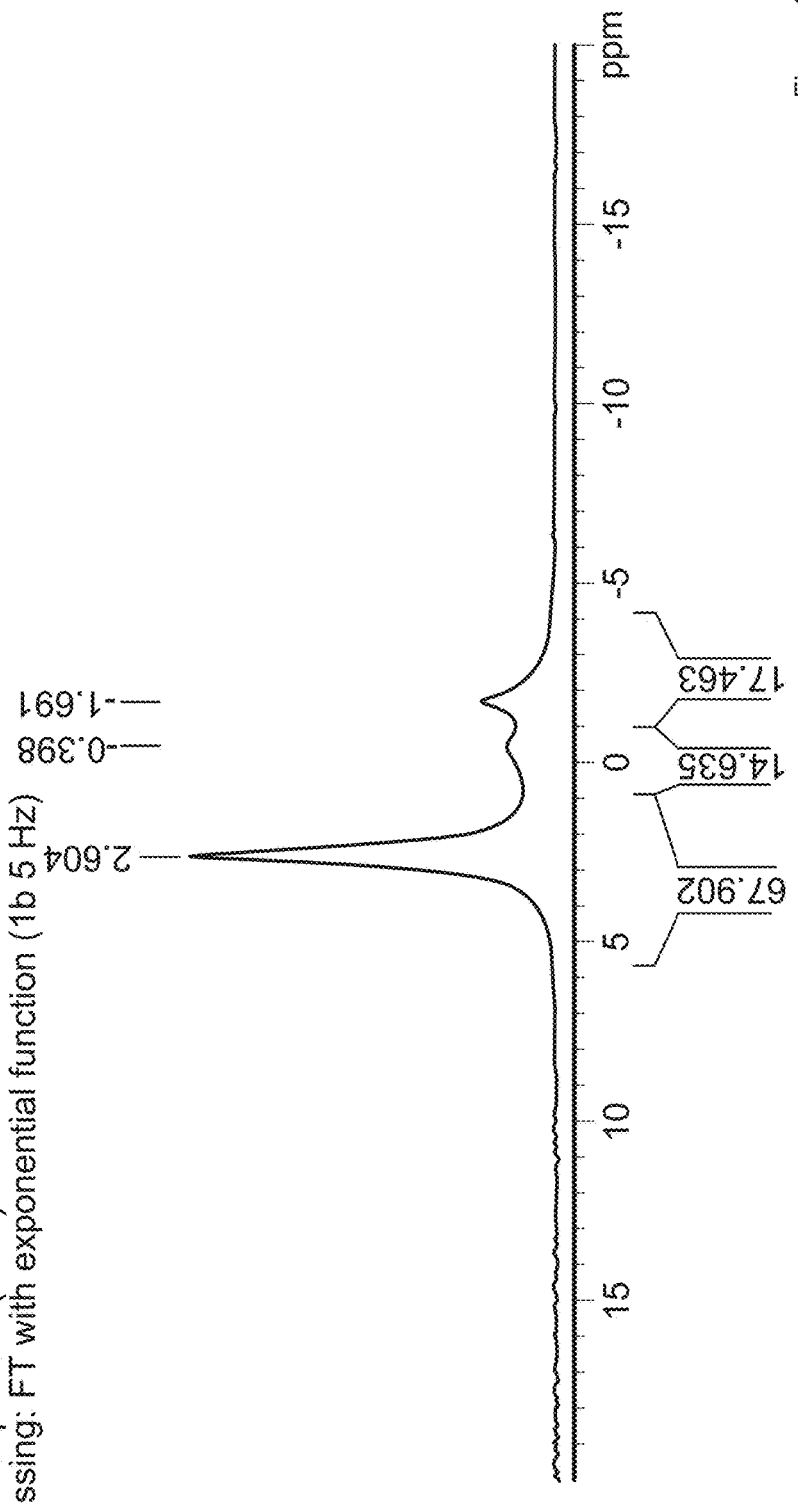
Figure 18B:
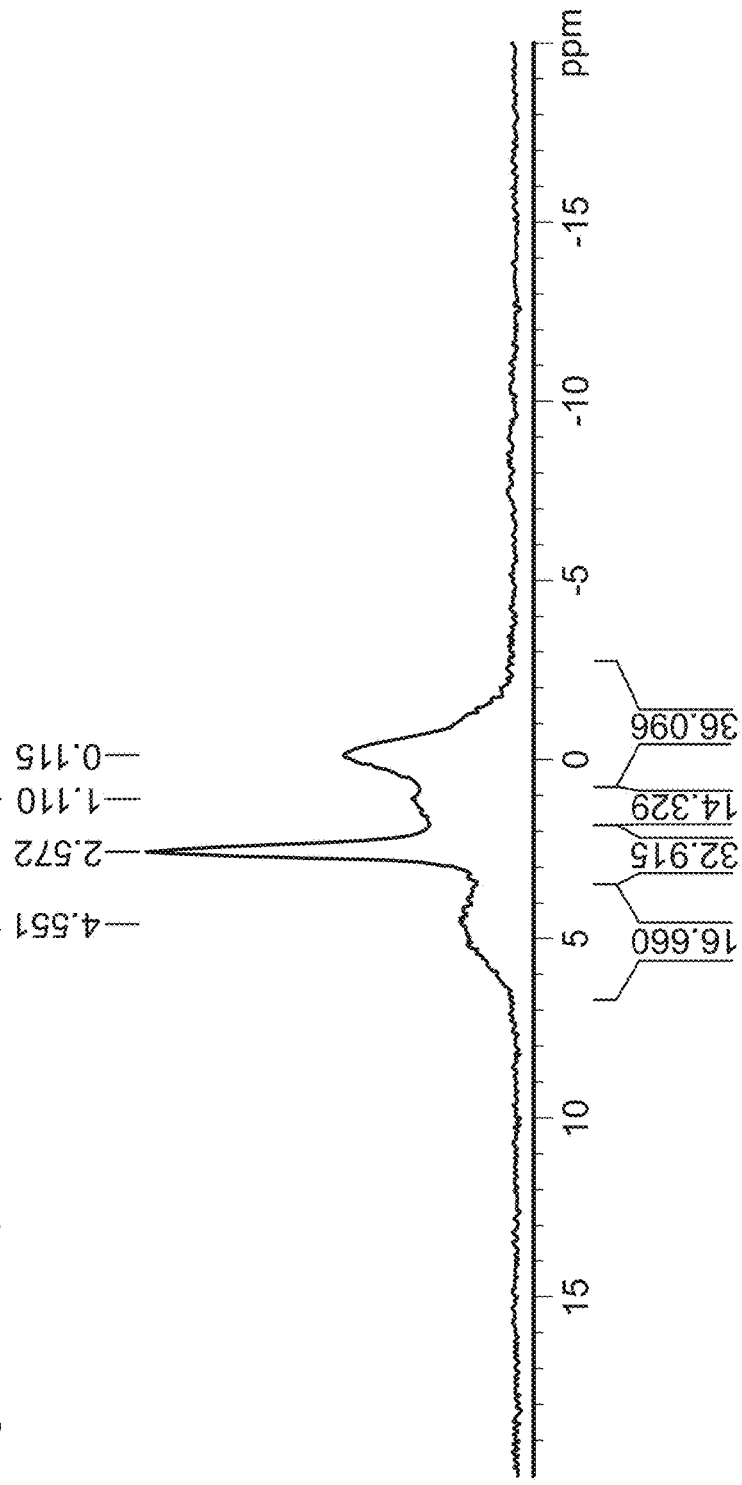
Figure 18C:
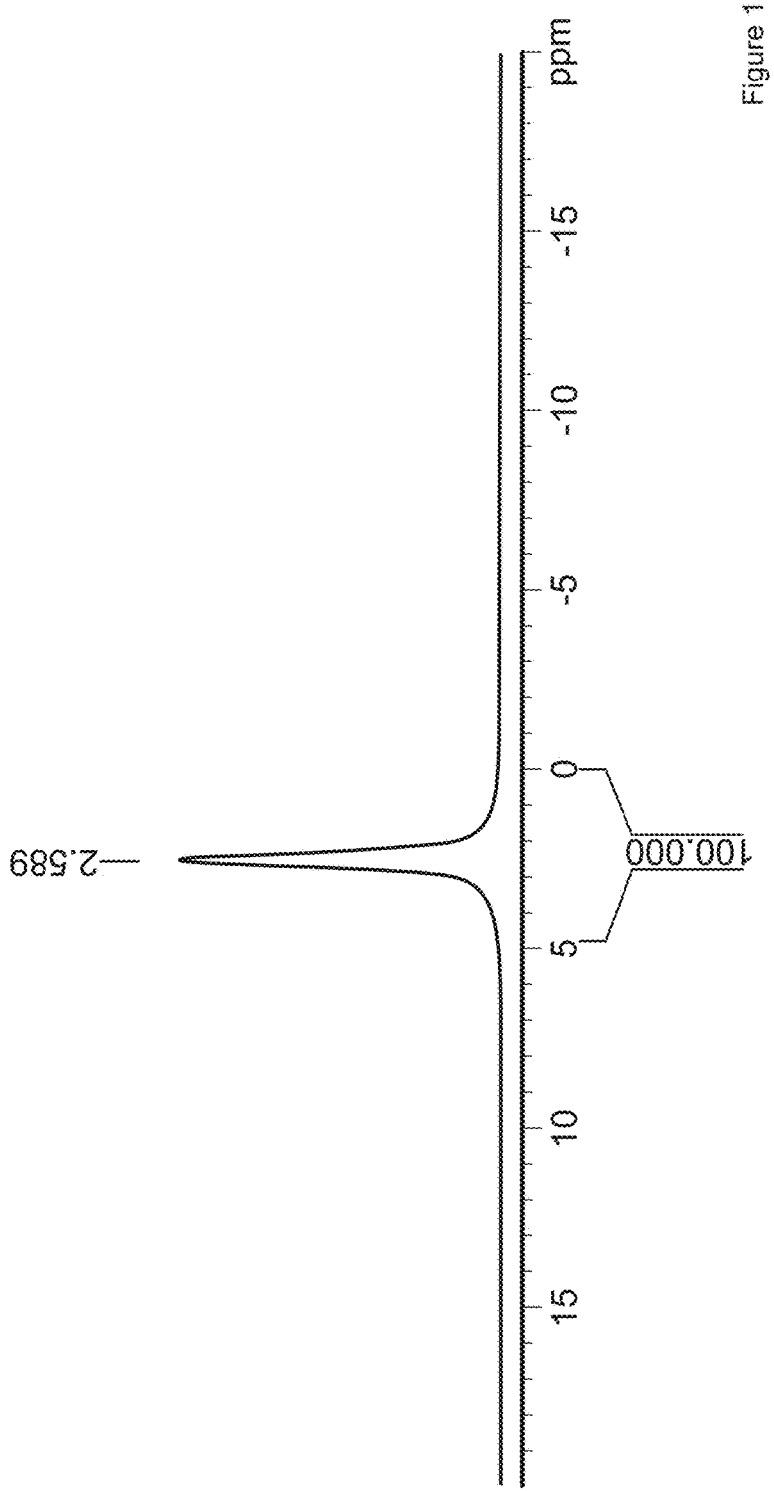

In a first aspect, the present invention relates to permanently polarized hydroxyapatite characterized in that its crystallinity is over 65%, preferably, over 70%, more preferably, over 75%, and its corresponding NMR $^{31}P$ spectrum is as shown on FIG. 18C.

In the present invention, the term "permanently polarized" means that the hydroxyapatite has undergone a complete structural redistribution, almost perfect, with a high crystallinity degree, i.e. particularly with a low amount of amorphous calcium phosphate and the presence of vacancies detected by increased electrochemical activity and the accumulation of charge per unit mass and surface. It has an electrochemical activity and ionic mobility which do not disappear over. The chemical differences between the permanently polarized hydroxyapatite and the corresponding synthesized and sintered hydroxyapatite are shown on NMR $^{31}P$ spectra according to FIGS. 18A-C.

FIGS. 18A-C display the solid state $^{31}P$ NMR spectra of cHAp/p, cHAp/s and cHAp/tsp samples (according to the present invention). The main resonance peak, present in cHAp/p, cHAp/s and cHAp/tsp at 2.9 ppm corresponds to bulk phosphate groups $PO_4^{3-}$ of hydroxyapatites.[56] Compared to cHAp/p, the line width of both cHAp/s and HAp/tsp samples are narrower, which is consistent with the increment of $\chi_c$ mentioned above. The broad signals at approximately [−1,0] ppm and a shoulder at [0,1] ppm, present in cHAp/p and cHAp/s, were usually assigned to the lone protonated surfaces phosphate groups arising from the disordered near surface layer.[57] Indeed, hydroxyapatite particles are typically described as an ordered hydroxyapatite core surrounded by a disordered non-apatitic surface layer.[47] The shoulder at 4-6 ppm, which is present in cHAp/s, is also due to the surface $HPO_4^{2-}$ ions, when its amount in the surface layer is greater that a certain threshold.[59] This increase in surface $HPO_4^{2-}$ ions in cHAp/s is caused by the more disordered surface layer due to the thermal process applied in cHAp/s particle treatment. The more unusual part is the only peak of typical bulk phosphate groups $PO_4^{3-}$ of hydroxyapatites present in cHAp/tsp. Thus, such particles undergo a treatment consisting in a constant DC electric field of 500 V, heating simultaneously at 1000° C. for 2 h. This thermal and electrical stimulation process (TSP) process was found to exert different effects on the hydroxyapatite surface properties.[60] Like the hydroxyapatite surface undergoes variations due to changes in the position of OH⁻ ions.[61] Accordingly, the fingerprint of the surface OH⁻ ions leaving from the columns due to the thermally and electrical stimulated polarization process in p-cHAp is the disappearance of the surface $HPO_4^{2-}$ ions and formation of holes in the valence band for the corresponding charge neutralization.

The present invention further relates to a composition or material comprising the permanently polarized hydroxyapatite as defined herein.

In a further embodiment, said composition or material is a medical, in particular pharmaceutical, composition or material.

In another further embodiment, said composition or material further comprises at least one of the followings: silicates; biocompatible polymers, including but not limited thereto, polylactic acid (PLA), poly lactic-co-glycolic acid (PGLA), polyglycolide (PGA), polydioxanone (PDO), polyhydroxybutyrate (PHB), polysaccharides and proteins such as collagen; organometallic compounds and metal ions, preferably selected from Mg, Sr, Fe, Mn, Zr, Au, and Ti, more preferably Zr.

In a second aspect, the present invention relates to a process for obtaining a permanently polarized hydroxyapatite, preferably as defined in any of the embodiments of the first aspect, comprising the steps of:
(a) obtaining sintered samples of hydroxyapatite and/or amorphous calcium phosphate at a temperature between 700° C. and 1200° C.;
(b) applying a constant or variable DC voltage between 250 V and 2500 V for at least 1 minute at a temperature between 900° C. and 1200° C. or
applying an equivalent electric field between 1.49 kV/cm and 15 kV/cm for at least 1 minute at a temperature between 900° C. and 1200° C. or
applying an electrostatic discharge between 2500 V and 1500000 V for less than 10 minutes at a temperature between 900° C. and 1200° C. or
applying an equivalent electric field between 148.9 kV/cm and 8928 kV/cm for less than 10 minutes at a temperature between 900° C. and 1200° C.;
(c) cooling the samples while applying the constant or variable DC voltage or the equivalent electric field, preferably to room temperature or
cooling the samples while applying the electrostatic discharge or the equivalent electric field, preferably to room temperature.

The process and the permanently polarized hydroxyapatite obtained or obtainable by that process has in particular the following advantages:

The sintering temperature as defined in step (a) is lower than that of Yamashita and co-workers[14] and advantageously avoids some undesirable phase transitions.

The current density of the obtained permanently polarized hydroxyapatite using a temperature as defined in step (b), which is the so-called polarization temperature, is several orders of magnitude higher than that achieved by Yamashita and co-workers[14] using a polarization temperature of 350° C. to 400° C. (~$10^{-5}$ A/cm² and ~$10^{-9}$ A/cm², respectively), proving the success of the inventors' treatment. It is worth noting that this was an unexpected result since Yamashita and coworkers[14] found that the current density decreases in the interval between 450 and 700° C. The success of the inventors' treatment has been attributed to the combination of the sintering temperature and a very high polarization temperature (between 900° C. and 1200° C.).

In a preferred embodiment, the sintered samples of hydroxyapatite obtained in step a) are selected from the group consisting of sintered samples of crystalline hydroxyapatite, sintered samples of amorphous hydroxyapatite and a mixture of said sintered samples. More preferably, the sintered samples of hydroxyapatite obtained in step a) are sintered samples of crystalline hydroxyapatite.

In a further embodiment, the sintered samples obtained in step a) are sintered samples of hydroxyapatite. The sintered samples of hydroxyapatite are preferably selected from the group consisting of sintered samples of crystalline hydroxyapatite, sintered samples of amorphous hydroxyapatite and a mixture of said sintered samples. More preferably, the sintered samples obtained in step a) are sintered samples of crystalline hydroxyapatite.

In another further embodiment, the sintered samples obtained in step a) are sintered samples of hydroxyapatite and amorphous calcium phosphate. The sintered samples of hydroxyapatite are preferably selected from the group consisting of sintered samples of crystalline hydroxyapatite, sintered samples of amorphous hydroxyapatite and a mixture of said sintered samples. More preferably, the sintered samples obtained in step a) are sintered samples of crystalline hydroxyapatite and amorphous calcium phosphate.

In a yet another embodiment, the sintered samples obtained in step a) are sintered samples of amorphous calcium phosphate.

The sintering step (a) is a thermal treatment of a ceramic at a temperature lower than its melting point. In the instant case, the sintering step is carried out at a temperature between 700° C. and 1200° C., preferably between 700° C. and 1150° C., more preferably between 800° C. and 1100° C., and most preferably about 1000° C.

Also, importantly, the process according to the second aspect of the present invention applies a constant DC voltage (see step (b)) and/or constant electric field as disclosed in the state of the art. When a constant DC voltage is applied the corresponding electric field is zero.

In a further embodiment, the constant or variable DC voltage or the equivalent electric field is applied in step (b) for 0.5 hours to 1.5 hours. In another embodiment, the constant or variable DC voltage or the equivalent electric field is applied in step (b) for about 1 hour.

In another further embodiment, the DC voltage applied in step (b) is about 500 V. Such a DC voltage would be equivalent to a constant electric field of 3.0 kV/cm.

In a yet another embodiment, the temperature in step (b) is at least 1000° C.

In a third aspect, the present invention relates to a process for obtaining a permanently polarized hydroxyapatite, preferably as defined in any of the embodiments of the first aspect, comprising the steps of:
(a) obtaining sintered samples of hydroxyapatite and/or amorphous calcium phosphate;
(b) heating the samples obtained in (a) at between 900° C. and 1200° C.;
(c) applying a constant or variable DC voltage between 250 V and 2500 V for at least 1 minute or
applying an equivalent electric field between 1.49 kV/cm and 15 kV/cm for at least 1 minute or
applying an electrostatic discharge between 2500 V and 1500000 V for less than 10 minutes or
applying an equivalent electric field between 148.9 kV/cm and 8928 kV/cm for less than 10 minutes;
(d) cooling the samples maintaining the DC voltage or the equivalent electric field, preferably to room temperature, or cooling the samples maintaining the electrostatic discharge or the equivalent electric field, preferably to room temperature In a preferred embodiment, the sintered samples of hydroxyapatite obtained in step a) are selected from the group consisting of sintered samples of crystalline hydroxyapatite, sintered samples of amorphous hydroxyapatite and a mixture of said sintered samples. More preferably, the sintered samples of hydroxyapatite obtained in step a) are sintered samples of crystalline hydroxyapatite.

In a further embodiment, the sintered samples obtained in step a) are sintered samples of hydroxyapatite. The sintered samples of hydroxyapatite are preferably selected from the group consisting of sintered samples of crystalline hydroxyapatite, sintered samples of amorphous hydroxyapatite and a mixture of said sintered samples. More preferably, the sintered samples obtained in step a) are sintered samples of crystalline hydroxyapatite.

In another further embodiment, the sintered samples obtained in step a) are sintered samples of hydroxyapatite and amorphous calcium phosphate. The sintered samples of hydroxyapatite are preferably selected from the group consisting of sintered samples of crystalline hydroxyapatite, sintered samples of amorphous hydroxyapatite and a mixture of said sintered samples. More preferably, the sintered samples obtained in step a) are sintered samples of crystalline hydroxyapatite and amorphous calcium phosphate.

In a yet another embodiment, the sintered samples obtained in step a) are sintered samples of amorphous calcium phosphate.

The sintering step (a) is a thermal treatment of a ceramic at a temperature lower than its melting point. In the instant case, the sintering step is preferably carried out at a temperature between 700° C. and 1200° C., more preferably 700° C. and 1150° C., even more preferably 800° C. and 1100° C., and most preferably about 1000° C.

Also, importantly, the process according to the third aspect of the present invention applies a constant DC voltage (see step (c)) and/or a constant electric field as disclosed in the state of the art. When a constant DC voltage is applied the corresponding electric field is zero.

In a further embodiment, the constant or variable DC voltage or the equivalent electric field is applied in step (c) for 0.5 hours to 1.5 hours. In another embodiment, the constant or variable DC voltage or the equivalent electric field is applied in step (c) for about 1 hour.

In another further embodiment, the DC voltage applied in step (c) is about 500 V.

In a yet another embodiment, the temperature in step (b) is at least 1000° C.

The advantages mentioned in the context of the process according to the second aspect of the present invention do analogously apply with respect to the process according to the third aspect of the present invention.

In a fourth aspect, the present invention relates to a permanently polarized hydroxyapatite obtained or obtainable by a process according to the second aspect or third aspect of the present invention. With regard to further features and advantages of the permanent polarized hydroxyapatite and process, reference is made to the embodiments described in the first and second aspect of the present invention.

In a fifth aspect, the present invention relates to the following uses of the permanently polarized hydroxyapatite.

The present invention further relates to the use of the permanently polarized hydroxyapatite as defined herein or the composition or material comprising said permanently polarized hydroxyapatite as defined herein in biomedical applications. Preferably, said biomedical application is selected from cementum for teeth, bone, prosthesis, medical devices, drug-delivery, gene therapy and tissue regeneration.

The present invention further relates to the use of the permanently polarized hydroxyapatite as defined herein or the composition or material comprising said permanently polarized hydroxyapatite as defined herein as electrodes.

The present invention further relates to the use of the permanently polarized hydroxyapatite as defined herein or the composition or material comprising said permanently polarized hydroxyapatite as defined herein for doping polymers.

The present invention further relates to the use of the permanently polarized hydroxyapatite as defined herein or the composition or material comprising said permanently polarized hydroxyapatite as defined herein as a catalyst, preferably as a photoelectrocatalyst or an electrocatalyst. Preferably, the use as a catalyst is in a reaction for the synthesis of organic molecules, in particular amino acids, preferably natural amino acids. Advantageously, the permanently polarized hydroxyapatite may exhibit superior catalytic performance and high adsorption capacity as further illustrated in the following.

The present inventors have found that the permanently polarized hydroxyapatite as defined herein or the composition or material comprising said permanently polarized hydroxyapatite as defined herein, can be used as a component in a layered, in particular trilayered, catalyst system based on (zirconium) amino tris(methylene phosphonic acid) which allows to catalyze the synthesis of natural amino acids, such as glycine and alanine. This synthesis takes place in the solid state with a significant yield and without rendering noticeable by-products as demonstrated by NMR spectroscopy. The reaction can be performed at a relatively low temperature (75-105° C.), short time (e.g. less than 24 h) and low pressure (e.g. less than 50 bar) but exposition to UV radiation is indispensable. The catalyst is able to fix molecular nitrogen which acts as the nitrogen source and adsorb $CO_2$. Carbon dioxide and methane are involved in the production of carboxylic groups and both methylene and methyl groups, respectively. Water also affects the catalyst modifying its dielectric behavior and contributing to ionic mobility. These results are very interesting since it is provided a new and clean synthesis process of organic molecules, such as amino acids that could proceed in the solid state, avoiding the dissolution of reactants in great water volumes as proposed in former prebiotic synthesis. The capacity of fixing molecular nitrogen and using a mildly reducing atmosphere ($N_2$, $CO_2$, $H_2O$ and $CH_4$) are also noticeable points of the new catalyst system. This surprising use opens the possibility of employing this catalyst family to get amino acids from a mildly reducing atmosphere (i.e. containing $H_2O$, $CH_4$, $N_2$ and $CO_2$,) instead of the less probable reducing atmosphere ($H_2O$, $CH_4$, $NH_3$ and $H_2$). Furthermore, the use of this catalyst by adsorbing $CO_2$ allows to obtain organic compounds (such as the production of amino acids as shown in the example section), while reducing the amount of $CO_2$ in the atmosphere which represents a clear contribution to the existing environmental problems due to high $CO_2$ volume concentrations in the atmosphere (green house effect).

This catalyst is based on the efficient zirconium oxychloride and amino tris(methylene phosphonic acid) trilayered system, abbreviated hereinafter as Phos-Zr-Phos. Nevertheless, the compound supporting the trilayered system should play a determinant rule to anchor properly the first phosphonate layer. This feature will be also evaluated comparing the results from a layered silicate (e.g. sodium montmorillonite), a layered aluminosilicate (e.g. mica) and a calcium phosphate compound (HAp, $Ca_{10}(PO_4)_6(OH)_2$)) able to establish strong ionic interactions between its calcium ions and the deposited phosphonate layer. The application of a thermally stimulated polarization to HAp enhanced the electrochemical activity and stability and the electrical conductivity, while increased significantly the adsorption of phosphates and phosphonates (particularly the amino tris (methylene phosphonic acid, ATMP) with respect to non-treated (as synthesized) HAp particles. (See example section for further details about this process)

The present invention further relates to the use of the permanently polarized hydroxyapatite as defined herein or the composition or material comprising said permanently polarized hydroxyapatite as defined herein for supporting, preferably adsorbing, organic molecules. Preferably, said molecules are selected from carbohydrates, amino acids, lipids, DNA, RNA, biopolymers and ATP. More preferably, said biopolymers are selected from polylactic acid (PLA), poly lactic-co-glycolic acid (PGLA), polyhydroxybutyrate (PHB), polydioxanone (PDO), polysaccharides and proteins and organo-metallic compounds.

The present invention further relates to the use of the permanently polarized hydroxyapatite as defined herein or the composition or material comprising said permanently polarized hydroxyapatite as defined herein for supporting, preferably adsorbing, phosphorous containing compounds such as pyrophosphate, triphosphate, triphosphonate and/or polyphosphates. The polyphosphates are preferably selected from any of the polyphosphates having from 1 to 50,000 monomer units or any combination thereof.

The present invention further relates to the use of the permanently polarized hydroxyapatite as defined herein or the composition or material comprising said permanently polarized hydroxyapatite as defined herein for supporting, preferably adsorbing, organometallic compounds, preferably metal phosphonates. The organo-metallic compounds are preferably compounds containing metal ions wherein the metal ions are selected from the group consisting of transition metals, lanthanides and combinations thereof. More preferably, the organometallic compounds are compounds containing metal ions wherein the metal ions are selected from the group consisting of Sr, Mg, Fe, Mn, Zr, Au, Ti and mixtures of at least two of said compounds.

The present invention further relates to the use of the permanently polarized hydroxyapatite as defined herein or the composition or material comprising said permanently polarized hydroxyapatite as defined herein for molecular recognition, preferably racemic resolution. The present invention further relates to the permanently polarized hydroxyapatite as defined herein or the composition or material comprising said permanently polarized hydroxyapatite as defined herein for use in the treatment of bone degradation and/or bone malignancies, such as osteoporosis. The present invention also relates to a method of treating bone degradation and/or bone malignancies, such as osteoporosis, in a subject, preferably a human subject, comprising administering to said subject a therapeutically effective amount of permanently polarized hydroxyapatite as defined herein or the composition or material comprising said permanently polarized hydroxyapatite as defined herein. The phrase "therapeutically effective amount" means the amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present disclosure may be administered in a sufficient amount to produce a reasonable benefit/risk ratio applicable to such treatment.

The present invention further relates to DNA/RNA for use in the treatment of diseases, wherein the DNA/RNA is administered by means of the permanently polarized hydroxyapatite as defined herein or the composition or material comprising said permanently polarized hydroxyapatite as defined herein. The present invention also relates to a method of treating diseases in a subject, preferably a human subject, comprising administering to said subject a therapeutically effective amount of DNA/RNA, wherein the DNA/RNA is administered by means of the permanently polarized hydroxyapatite as defined herein or the composition or material comprising said permanently polarized hydroxyapatite as defined herein. The DNA/RNA is preferably selected from the group consisting of double-stranded or single-stranded DNA or RNA cointaining sequences related to diseases (i.e. cancer, neuronal diseases or diseases related to tissue calcifications) and mixtures of at least two of said DNA/RNA. The diseases are preferably selected from the group consisting of genetic disorders including, but not limited thereto, Achondroplasia, Alpha-1 Antitrypsin Deficiency, Antiphospholipid Syndrome, Autism, Autosomal Dominant Polycystic Kidney Disease, Breast cancer, Charcot-Marie-Tooth, Colon cancer, Cri du chat, Crohn's Disease, Cystic fibrosis, Dercum Disease, Down Syndrome, Duane Syndrome, Duchenne Muscular Dystrophy, Factor V Leiden Thrombophilia, Familial Hypercholesterolemia, Familial Mediterranean Fever, Fragile X Syndrome, Gaucher Disease, Hemochromatosis, Hemophilia, Holoprosencephaly, Huntington's disease, Klinefelter syndrome, Marfan syndrome, Myotonic Dystrophy, Neurofibromatosis, Noonan Syndrome, Osteogenesis Imperfecta, Parkinson's disease, Phenylketonuria, Poland Anomaly, *Porphyria*, Progeria, Prostate Cancer, Retinitis Pigmentosa, Severe Combined Immunodeficiency (SCID), Sickle cell disease, Skin Cancer, Spinal Muscular Atrophy, Tay-Sachs, Thalassemia, Trimethylaminuria, Turner Syndrome, Velocardiofacial Syndrome, WAGR Syndrome, Wilson Disease) and diseases related to tissue calcifications including, but not limited thereto, diseases related to small and large arteries, heart valves, brain (where it is known as cranial calcification), joints and tendons, such as knee joints and rotator cuff tendons, soft tissues like breasts, muscles, and fat, kidney, bladder, and gallbladder.

The present invention further relates to the use of the permanently polarized hydroxyapatite as defined herein or the composition or material comprising said permanently polarized hydroxyapatite as defined herein as a component in a solid-state battery. As used herein, a solid-state battery is a battery that has both solid electrodes and solid electrolytes. As a group, these materials are very good conductors of ions, which is necessary for good electrolyte and electrode performance, and are essentially insulating toward electrons, which is desirable in electrolytes but undesirable in electrodes. The high ionic conductivity minimizes the internal resistance of the battery, thus permitting high power densities, while the high electronic resistance minimizes its self-discharge rate, thus enhancing its charge retention.

The present invention further relates to the use of the permanently polarized hydroxyapatite as defined herein or the composition or material comprising said permanently polarized hydroxyapatite as defined herein as a component in an energy harvesting chip which is a chip that can generate their own energy. Energy harvesting is defined as the conversion of ambient energy into usable electrical energy. When compared with the energy stored in common storage elements, like batteries and the like, the environment represents a relatively inexhaustible source of energy. Consequently, energy harvesting (i.e. scavenging) methods must be characterized by their power density, rather than energy density.

The present invention is now further illustrated by reference to the following examples which do not intend to limit the scope of the invention.

EXAMPLES

Process for Obtaining Permanently Polarized HAp and ACP

Materials.

Ammonium phosphate dibasic [$(NH_4)_2HPO_4$; purity 99.0%], ammonium hydroxide solution 30% ($NH_4OH$; purity: 28-30%), tetrasodium pyrophosphate ($Na_4P_2O_7$)), sodium triphosphate (polyP) and ATMP were purchased from Sigma-Aldrich. Calcium nitrate [$Ca(NO_3)_2$; purity ≥99.0%] was purchased from Panreac (Barcelona, Spain). Ethanol ($C_2H_5OH$; purity ≥99.5%) was obtained from Scharlab (Barcelona, Spain). Fetal bovine serum (FBS), for contact angle measurements, was purchased from Gibco.

Synthesis of HAp and ACP.

A simple procedure was used to prepare ACP and cHAp samples, the only difference being the thermal post-treatment applied to the reaction mixture.[35] Reagent conditions were adjusted to get a Ca/P ratio of 1.67. For both ACP and cHAp, 15 mL of 0.5 M $(NH_4)_2HPO_4$ in de-ionized water (pH adjusted to 11 with an ammonia 30% w/w solution) were added drop-wise (rate of 2 mL·$min^{-1}$) and under agitation (400 rpm) to 25 mL of 0.5 M $Ca(NO_3)_2$ in ethanol. After that, the reaction mixture was stirred 1 h by agitation (400 rpm) at room temperature. In the case of ACP the resulting suspension was aged for 24 h at 37° C., whereas hydrothermal conditions were applied during 24 h for cHAp. In the hydrothermal synthesis the crystal growth is performed in an apparatus consisting of a steel pressure vessel called an "autoclave", in which a nutrient is supplied along with water. In the instant case, the temperature was 150° C. and the pressure was 200 bar.

In both cases, the precipitate was separated by centrifugation and washed sequentially with de-ionized water and a 60/40 v/v mixture of ethanol-water (twice). A white powder was recovered after freeze-drying. ACP and cHAp obtained using this procedure have been denoted "as prepared" samples, hereafter abbreviated ACP/p and cHAp/p, respectively.

Sintering and thermally stimulated polarization process.

Sintered cHAp and ACP samples, hereafter denoted cHAp/s and ACP/s, respectively, were prepared by heating the previously synthesized powders at 1000° C. for 2 h in air. This temperature is lower than that used by Yamashita and co-workers.[14,15] After this, powders were uniaxially pressed at 620 MPa for 10 min to obtain dense discs suitable for characterization. The dimensions of these specimens were 10 mm of diameter×1.68 mm of thickness.

In order to get thermally stimulated polarized ACP and cHAp (ACP/tsp and cHAp/tsp, respectively), discs of sintered samples were sandwiched between stainless steel (AISI 304) plates, heated to 1000° C. in air and, simultaneously, polarized for 1 h under application of a constant DC voltage (V). This polarization temperature as disclosed herein is out of the temperature values (i.e. <700° C.) employed by Yamashita and co-workers,[14,15] who indicated that temperatures higher 450° C. have a negative impact in the polarization process, leading to a reduction in the current intensity of the polarized samples. Subsequently, samples were cooled to room temperature, maintaining the DC voltage. Preliminary assays were performed using V values that ranged from 250 to 2000 V (i.e. a constant electric field from 1.49 to 11.9 kV/cm), the best results being obtained for 500 V (i.e. 2.98 kV/cm). Accordingly, all experiments described in this work correspond to ACP/tsp and cHAP/tsp samples polarized using V=500 V.

Characterization of the Permanently Polarized HAp and ACP

X-Ray Diffraction.

The crystallinity and structure was studied by wide angle X-ray diffraction (WAXD). Patterns were acquired using a Bruker D8 Advance model with Cu $K_\alpha$ radiation ($\lambda$, =0.1542 nm) and geometry of Bragg-Brentano, theta-2 theta. A one-dimensional Lynx Eye detector was employed. Samples were run at 40 kV and 40 mA, with a 2-theta range of 10-60, measurement steps of 0.02°, and time/step of 2-8 s. Diffraction profiles were processed using PeakFit v4 software (Jandel Scientific Software) and the graphical representation performed with OriginPro v8 software (OriginLab Corporation, USA).

The crystallite size (L) in the direction perpendicular to the (211) planes was derived from X-ray diffraction profiles considering the (211) peak width and line broadening measurement using the Scherrer equation:[36]

$$L = \frac{0.9\lambda}{\beta \cos\theta} \quad (1)$$

where $\lambda$ is the wavelength ($CuK_\alpha$), $\beta$ is the full width at half maximum height of the (211) peak, $\theta$ is the diffraction angle and 0.9 is a shape factor.

The crystallinity ($\chi_c$) was obtained using the following expression:[37]

$$\chi_c = 1 - \frac{V_{112/300}}{I_{300}} \quad (2)$$

where $I_{300}$ is the intensity of the (300) reflection and $V_{112/300}$ is the intensity of the hollow between the (112) and (300) reflections, which disappears in non-crystalline samples.

X-ray photoelectron spectroscopy (XPS).

XPS analyses were performed in a SPECS system equipped with a high-intensity twin-anode X-ray source XR50 of Mg/Al (1253 eV/1487 eV) operating at 150 W, placed perpendicular to the analyzer axis, and using a Phoibos 150 MCD-9 XP detector. The X-ray spot size was 650 µm. The pass energy was set to 25 and 0.1 eV for the survey and the narrow scans, respectively. Charge compensation was achieved with a combination of electron and argon ion flood guns. The energy and emission current of the electrons were 4 eV and 0.35 mA, respectively. For the argon gun, the energy and the emission current were 0 eV and 0.1 mA, respectively. The spectra were recorded with pass energy of 25 eV in 0.1 eV steps at a pressure below $6\times10^{-9}$ mbar. These standard conditions of charge compensation resulted in a negative but perfectly uniform static charge. The C1s peak was used as an internal reference with a binding energy of 284.8 eV. High-resolution XPS spectra were acquired by Gaussian-Lorentzian curve fitting after s-shape background subtraction. The surface composition was determined using the manufacturer's sensitivity factors.

FTIR spectroscopy.

Infrared absorption spectra were recorded with a Fourier Transform FTIR 4100 Jasco spectrometer in the 1800-700 $cm^{-1}$ range. A Specac model MKII Golden Gate attenuated total reflection (ATR) equipment with a heating Diamond ATR Top-Plate was used.

Morphology.

Scanning electron microscopy (SEM) studies were carried out using a Focused Ion Beam Zeiss Neon40 microscope operating at 5 kV, equipped with an energy dispersive X-ray (EDX) spectroscopy system. Samples were deposited on a silicon disc mounted with silver paint on pin stubs of aluminum, and sputter-coated with a thin layer of carbon to prevent sample charging problems.

Contact profilometry.

The surface roughness (Rq) of the prepared HAp discs was determined using a stylus profilometer (Veeco, Plainview, NY, USA).

Contact angle.

Measurements were carried out using the sessile drop method at room temperature on an OCA 15EC with SCA20 software (Data-Physics Instruments GmbH, Filderstadt, Germany). The solvents used for these experiments were deionized water and FBS, contact angles being determined for both the first and second drop (θ and θ', respectively). For θ measurements, the sessile drop was gently put on the surface of sample discs using a micrometric syringe with a proper metallic needle (Hamilton 500 μL). The ellipse method was used to fit a mathematical function to the measured drop contour. This procedure consists on approximate the drop contour to the line of an ellipse, deviations from the true drop shape being in the range of a few percent. The ellipse method provides accurate measure of the contact angle and holds the advantage that it is extremely fast. For each solvent, no less than ten drops were examined. Measures of θ' were performed using the same procedure, even though an equilibration time of 1 min. was applied after depositing the second drop onto the first one.

Determination of water content.

HAp discs were dried in an oven (100° C.) for 15 h. After this, samples reached the room temperature in a desiccator, being immediately weighted. Next, samples were immersed in deionized water for 1 hour. Samples were removed, patted dry with a lint free cloth, and weighted. The water content, expressed as increment in weight percent, was calculated as follows:

$$M_W(\%) = \frac{(W_W - W_D)}{W_D} \times 100 \quad (1)$$

where $M_W$ is the water content of the sample, $W_W$ is the weight of the wet sample, and WD the weight of the dried sample. $W_W$ and $W_D$ were determined using a Sartorius CPA26P analytical micro-balance.

Cyclic voltammetry (CV).

The electrochemical behavior was determined by CV using an Autolab PGSTAT302N equipped with the ECD module (Ecochimie, The Netherlands) with a three-electrode cell under a nitrogen atmosphere (99.995% in purity) at room temperature. A 0.1 M phosphate buffer saline solution (PBS; pH=7.2 adjusted with NaOH) was used as the electrolyte in the three-electrode cell. The working compartment was filled with 30 mL of the electrolyte solution. Steel AISI 316 sheets of 1×1.5 $cm^2$ (thickness 0.1 cm) were used as both the working and the counter electrodes, and an AgIAgCl electrode was used as the reference electrode which contained a KCl saturated aqueous solution (offset potential versus the standard hydrogen electrode, $E°=0.222$ V at 25° C.). All potentials given in this report are referenced to this electrode. HAp discs prepared as described above were fixed on the working electrode using a two-side adhesive carbon layer. The initial and final potentials were −0.40 V, whereas a reversal potential of 0.80 V was considered. The scan rate was 50 mV/s.

The electroactivity, which indicates the ability to exchange charge reversibly, was evaluated by examining the similarity between the anodic and cathodic areas of the control voltammogram. The electrochemical stability (i.e. loss of electroactivity, LEA), which decreases with the oxidation and reduction areas of consecutive control voltammograms, was determined using the following expression:

$$LEA = \frac{\Delta Q}{Q_{II}} 100^{SC} = \frac{i\Delta t}{\Delta V} \quad (2)$$

where ΔQ is the difference of voltammetric charge between the second cycle and the last cycle and $Q_{II}$ is the voltammetric charge corresponding to the second cycle. In this work all values of LEA were referred to 1000 consecutive oxidation-reduction cycles.

The specific capacitance (SC; in F/g) of HAp in the electrode was calculated as:

$$SC = \frac{Q}{\Delta Vm} \quad (3)$$

where Q is voltammetric charge, which is determined by integrating either the oxidative or the reductive parts of the cyclic voltammogram curve, ΔV is the potential window and m is the mass of polymer on the surface of the working electrode. The latter is derived from the productivity current and polymerization charge.[38]

Electrochemical Impedance Spectroscopy (EIS).

EIS measurements were performed using an AUTOLAB PGSTAT302N in the 10 kHz to the 10 mHz frequency range and the amplitude of the sinusoidal voltage was 10 mV. All experiments were carried at room temperature. Appropriated sized films were pressed in a disc format and were sandwiched between two stainless steel electrodes (diameter=1.5 cm) assembled into an isolating resin holder.[39] The cell was tightened with screws to ensure constant pressure fastening. Films thickness was between 1.68 and 2.00 mm determined by a micrometer and the area was about 1.766 $cm^2$. Prior analyses, samples were previously dried by heating at 100° C. in an oven overnight. After data collection, EIS results were then processed and fitted to an electrical equivalent circuit (EEC).

Adsorption onto treated cHAP.

The concentration of the adsorbate in the working solutions was 100 mM for $P_2O_7^{4-}$ and 200 mM for both polyP and ATMP, while the pH considered in this study was 7 in all cases. The concentration of $P_2O_7^{4-}$ was a half of that used for the other two adsorbates because of limitations in the solubility of the former specie. For the incubation, 500 μL of the working solution with the adsorbate were deposited onto 50 mg of cHAp. After overnight agitation at 25° C., adducts were separated by centrifugation at 6500 rpm during 5 minutes at 4° C. Sediments were re-suspended in distilled water. After this process, which was repeated two times, the obtained pellets were frozen at −80° C. for 3 h and, subsequently, the humidity was removed using a lyophilizer.

Figure 1:
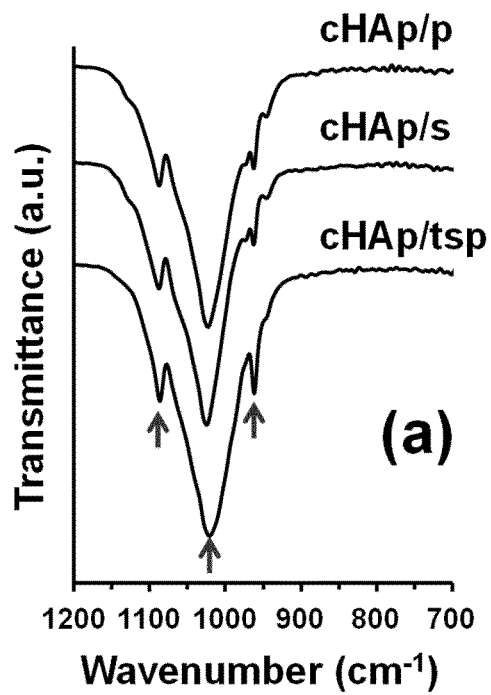
FIG. 1. FTIR spectra of (a) cHAp and (b) ACP.
Figure 1:
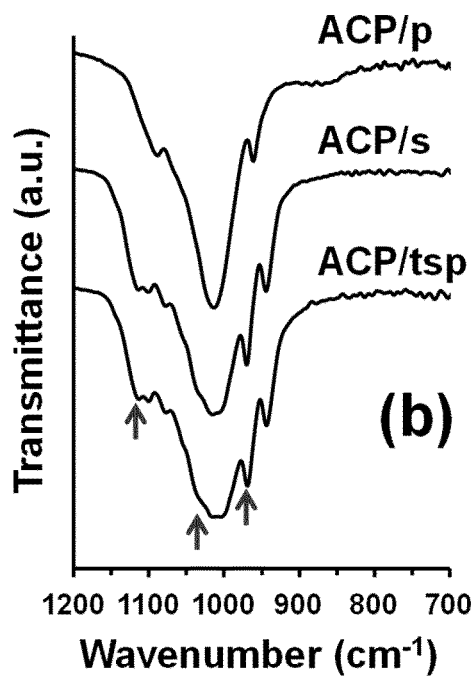

Chemical Characterization and Choice of Samples for Electrochemical and Adsorption Assays The FTIR spectra of the studied cHAp and ACP samples, which show typical $PO_4^{3-}$ bands at the region comprised between 950 and 1200 $cm^{-1}$, are compared in FIG. 1. The spectra of cHAp/p, cHAp/s and cHAp/tsp show characteristic vibrational modes of $PO_4^{3-}$ at $v_1$=962 $cm^{-1}$ and $v_3$=1016, 1087 $cm^{-1}$, the resemblance between the three spectra indicating that cHAp/p does not undergo significant structural changes when sintered and polarized. In contrast, the apparition of new bands and shoulders (i.e. at 970 and 1037 $cm^{-1}$), as well as the shifts in the existing bands (i.e. from 963 and 1090 $cm^{-1}$ to 947 and 1098 $cm^{-1}$, respectively), in the spectra of ACP/s and ACP/tsp evidence important structural re-organizations in ACP/p after thermal and polarization treatment. Powder ACP samples heated at temperatures ranging between 600 and 1000° C. were characterized by Raynaud et al.[40] The apparition of new FTIR bands were attributed to the formation of a structure formed by cHAp and tricalcium phosphate (TCP) phases.

Figure 10:
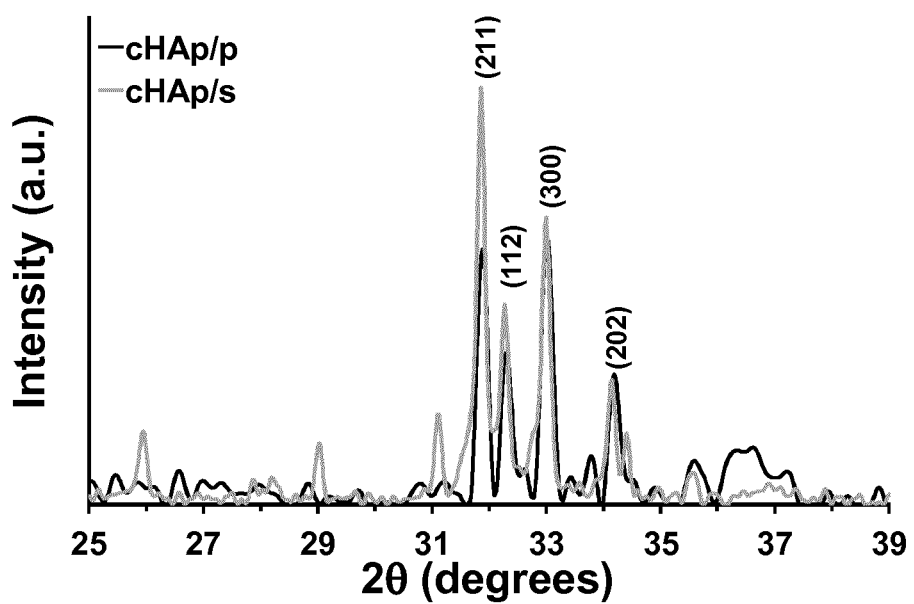
FIG. 10. X-ray diffraction patterns of the cHAp/p and cHAp/s samples, which were identified by the peaks at 2θ=32°-34°.
Figure 11:
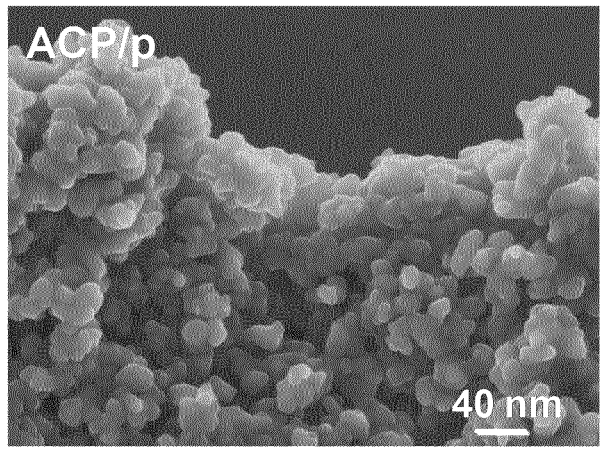
FIG. 11. SEM micrographs of ACP/p, ACP/s and ACP/tsp particles. The nanospherical morphologies found in ACP/p transforms into fusiform nanorods in ACP/tsp, whereas the two morphologies seem to coexist in ACP/s.
Figure 11:
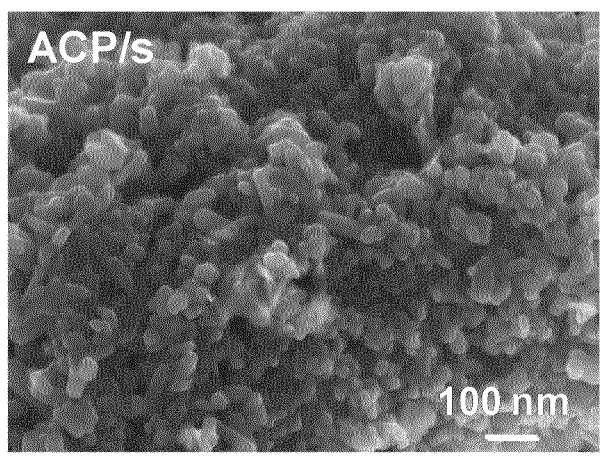
Figure 11:
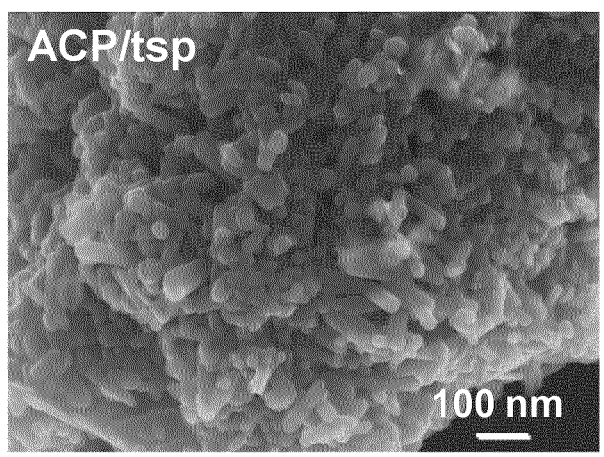

Structural analyses of cHAp and ACP particles by WAXD were focused on peaks at 2θ=32°-34°, which are characteristic of the (211), (112), and (300) HAp reflections. Although the comparison between the diffraction patterns recorded for cHAp/p and cHAp/tsp reveal small structural changes (FIG. 2a), the thermally stimulated polarization process provokes important increments in both the crystallinity ($\chi_c$) and the crystallite size (L). Thus, the $\chi_c$ of cHAp/p and cHAp/tsp samples was 0.42±0.01 and 0.75±0.02, respectively, while the crystallite size of cHAp/tsp, L=86±2 nm, was around 40% larger than that of cHAp/p (L=61±2 nm). The variation of $\chi_c$ and L has been attributed to the formation of OH⁻ defects. Fujimori et al.[41] reported that OH⁻ ions scape from the HAp matrix above 800° C., this dehydration process giving place to the formation of vacancies and $O^{2-}$ ions. In addition to the induction of a small amount of OH⁻ defects, a monoclinic-to-hexagonal thermal phase transition occurs upon the application of such treatment.[42-44] The hexagonal phase becomes most stable at room temperature because of the order-disorder phase transition, which is accounted for by the change in the position of the OH⁻ ions.[42-44] Although the structural differences between monoclinic and hexagonal HAP are small (FIG. 2a) they are sufficient to exert a strong impact on some of its properties (see next subsections). The diffraction pattern recorded in this work for cHAp/s ($\chi_c$=0.65±0.02 and L=86±3 nm) is compared in FIG. 10 with that of cHAp/p.

Figure 3:
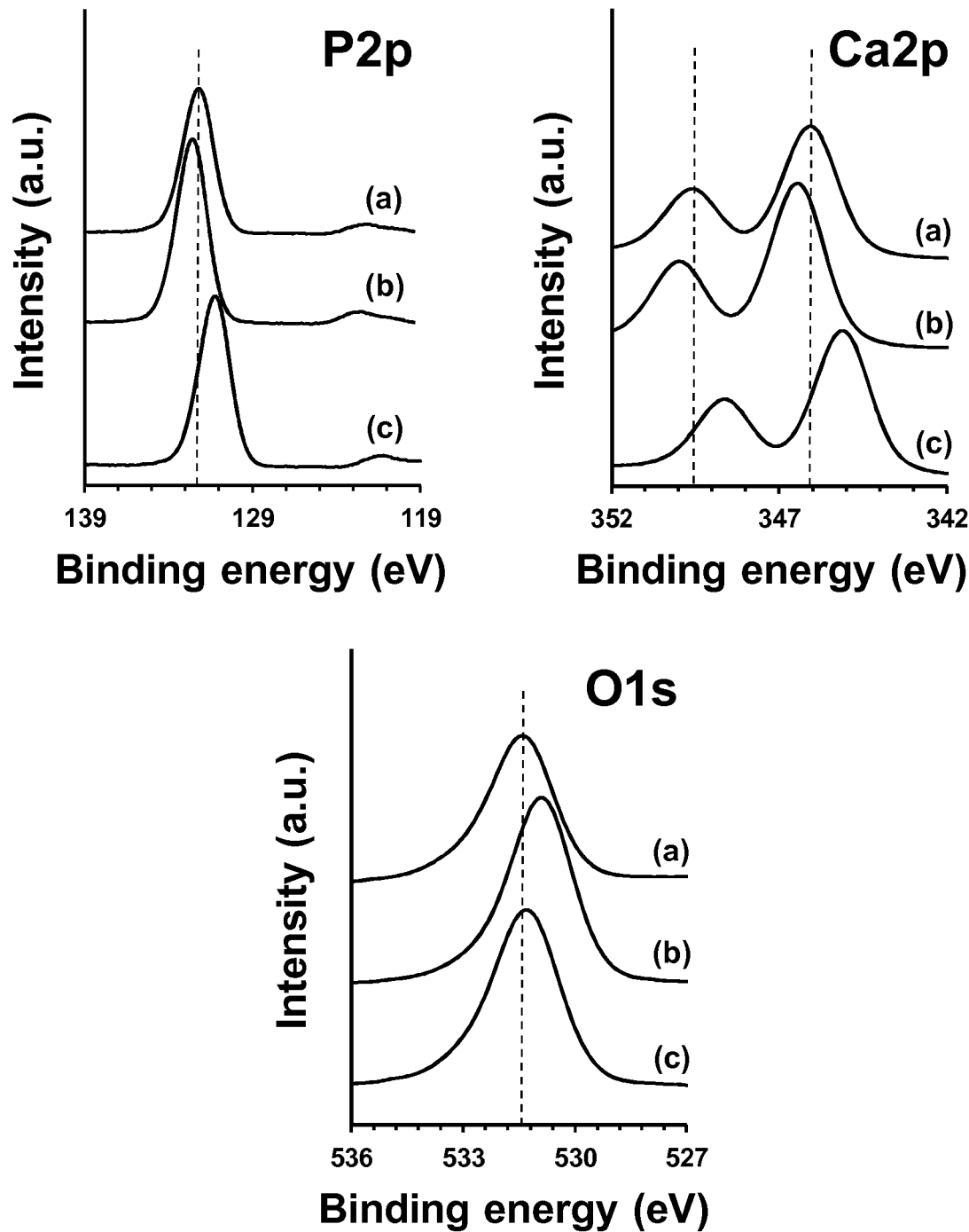
FIG. 3. High-resolution XPS spectra for (a) cHAp/p, (b) cHAp/s and (c) cHAp/tsp samples: P2p, Ca2p, and O1s regions.

FIG. 3 compares the characteristic XPS spectra in the P 2p, Ca 2p and O 1s regions for cHAp/p, cHAp/s and cHAp/tsp. For cHAp/p the single P2p peak centered at 132.2 eV, which originates from the $PO_4^{3-}$ anions,[45,46] undergoes a slight shift towards higher and lower energies ($\Delta_{BE}$=+0.4 and −1.0 eV) upon the application of sintering and thermally stimulated polarization treatment, respectively. The binding energies of the Ca $2p_{3/2}$ and Ca $2p_{1/2}$ peaks, which are detected at 346.1 and 349.6 eV, respectively, for cHAp/p,[45,47] experience shifts to 346.5 and 350.0 eV for cHAp/s and to 345.1 and 348.6 eV for cHAp/tsp. These variations are fully consistent with the existence of structural changes associated to phase transitions. Moreover, inspection of the chemical composition as determined by XPS, which is displayed in Table 1, is consistent with the formation of thermally-induced OH⁻ vacancies. Thus, the content of oxygen is around 2 wt. % lower for cHAp/s and cHAp/tsp than for cHAp/p. Interestingly, the Ca/P molar ratio of the cHAp/p samples is very close to the stoichiometric value of 1.67. However, cHAp/s and cHAp/tsp experience a small reduction with respect to such ideal value, supporting the apparition of vacancies. On the other hand, the nitrogen found in cHAp/p, cHAp/s and cHAp/tsp, which ranges from 0.28 to 0.40 wt. %, has been attributed to the adsorption of $N_2$ from the atmosphere.

TABLE 1

Ca, P, O, Na and N concentration (wt %) and Ca/P molar ratios determined by XPS of cHAP/p, cHAp/s and cHAp/tsp samples before and after incubation in presence of $P_2O_7^{4-}$, polyP and ATMP.

| | Ca (wt. %) | P (wt. %) | O (wt. %) | Na (wt. %) | N (wt. %) | Ca/P (molar) |
|---|---|---|---|---|---|---|
| cHAp/p | 38.76 | 18.09 | 42.86 | 0.00 | 0.29 | 1.66 |
| cHAp/s | 39.76 | 19.01 | 40.95 | 0.00 | 0.28 | 1.62 |
| cHAp/tps | 40.12 | 18.95 | 40.53 | 0.00 | 0.40 | 1.64 |
| cHAp/s + $P_2O_7^{4-}$ | 39.67 | 22.76 | 31.67 | 5.58 | 0.32 | 1.59 |
| cHAp/s + polyP | 38.76 | 18.95 | 35.62 | 6.38 | 0.29 | 1.32 |
| cHAp/s + ATMP | 39.23 | 19.27 | 38.32 | 0.00 | 3.18 | 1.48 |
| cHAp/tsp + $P_2O_7^{4-}$ | 39.54 | 22.56 | 25.64 | 11.91 | 0.35 | 1.35 |
| cHAp/tsp + polyP | 40.03 | 27.34 | 22.58 | 9.84 | 0.21 | 1.13 |
| cHAp/tsp + ATMP | 39.12 | 24.08 | 32.72 | 0.00 | 4.08 | 1.26 |

Figure 2:
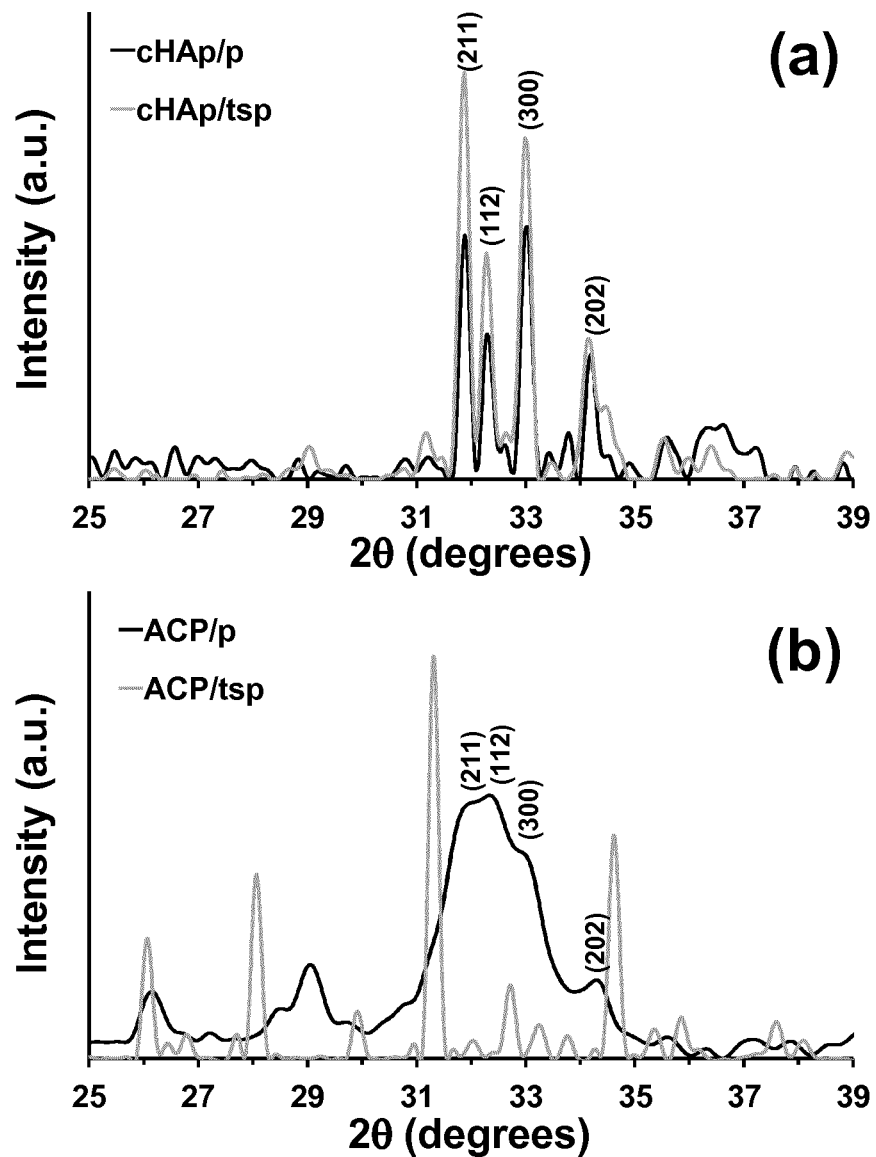
FIG. 2. X-ray diffraction patterns of the cHAp and ACP particles studied in this work: (a) cHAp/p and cHAp/tsp; and (b) ACP/p and ACP/tsp. cHAp and ACP samples were identified by the peaks at 2θ=32°-34°.

Comparison of the diffraction patterns recorded for ACP samples as prepared and after conducting the thermally stimulated polarization process (ACP/p and ACP/tsp, respectively) is provided in FIG. 2b. In this case, changes are very drastic, as is also reflected by the growth of $\chi_c$ and L from 0.05±0.02 and 5±1 nm for ACP/p to 0.74±0.03 and 52±3 nm for ACP/tsp. The structure exhibited by the crystalline fraction of ACP/p is identical to that observed for cHAp/p. However, the sintering process provokes the apparition of β-tricalcium phosphate (β-TCP: β-$Ca_3(PO_4)_2$) as the predominant phase. Although the high peaks at 2θ=31.3° and 34.6° match well with those of the β-TCP card (#09-0169) in the Joint Committee on Powder Diffraction Standards (JCPDS), the coexistence cHAp as a minor phase of ACP/tsp is probed by the persistent peak positions at 2θ=31.9°, 32.3°, 33.0° and 34.3°. These results suggest that the thermally stimulated polarization process induces partial decomposition of ACP/p, leading to the formation of β-TCP. A similar behavior was reported by different authors for sintered ACP (ACP/s) at 1100° C. (i.e. without applying any electric field),[5,47,48] and corroborated by our observation in the diffraction obtained for the samples prepared in this work by heating ACP/p to 1000° C. for 2 h in air (not shown). SEM micrographs displayed in FIG. 10 reflect the drastic structural changes undergone by ACP/p samples when treated thermally and electrically.

Because of the predominance of the β-TCP phase in ACP/tsp transition, the rest of the present work (i.e. surface and electrochemical properties, as well as adsorption ability) has been focused on the comparison between cHAp/p and cHAp/tsp. For the sake of completeness, such comparison has been extended to sintered cHAp samples (named cHAp/s).

Surface Characterization

Figure 4:
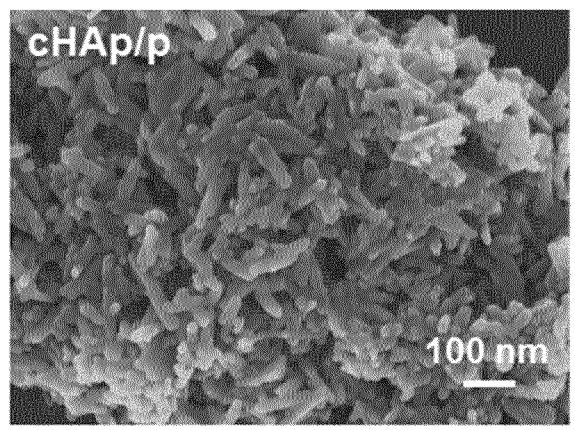
FIG. 4. SEM micrographs of cHAp/p, c/HAp/s and cHAp/tsp particles.
Figure 4:
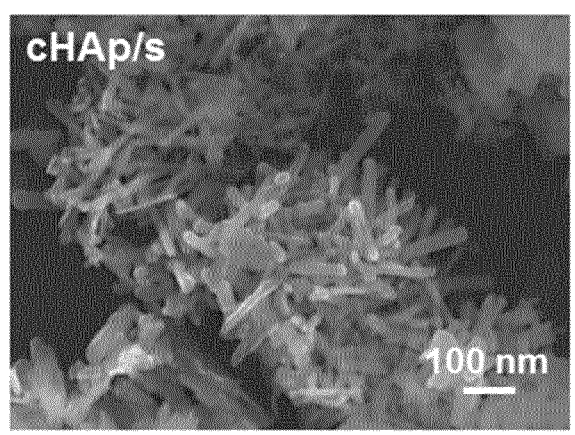
Figure 4:
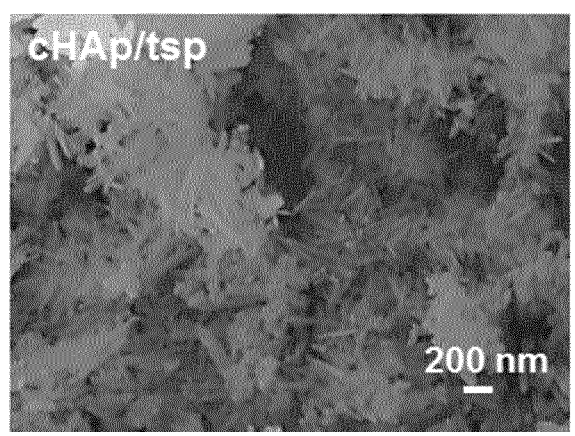

The surface morphologies of cHAp/p, cHAp/s and cHAp/tsp samples are compared in FIG. 4. As it can be seen, SEM micrographs corroborate previously discussed WAXD results. cHAp/p samples are constituted by laminar crystals and fusiform rods, the same elements being also identified in cHAp/s and cHAp/tsp. However, the amount of such elements increases upon the application of external treatments, especially the thermal stimulation polarization. Thus, crystals are bigger in HAp/tsp than in cHAp/p and c/HAp/s, which is consistent with the $\chi_c$ variation discussed above. On the other hand, micrographs clearly reflect that the crystallite size increases with the increasing amount of crystals (i.e. WAXD results showed that L varies as follow: cHAp/tsp>cHAp/s>cHAp/p).

Table 2 indicates that, although the surface roughness (Rq) of cHAp/p samples remained practically unaltered upon the application of the polarization and/or thermal treatments, the surface energy changed considerably. The contact angle of water ($\theta_{water}$) was ~4° for cHAp/p, cHAp/s and cHAp/tsp, indicating that the three are very hydrophilic materials, as it was expected because of their surface charge. In contrast, the contact angle in FBS ($\theta_{FBS}$) was significantly lower for cHAp/s and cHAp/tsp than for cHAp/p (Table 2). This variation in the wetting suggests that the re-organization of the ions induced by the thermal and, especially, the polarization treatments increases the contribution of the polar component to the surface energy. In order to support the relative increase of the dispersive contribution with respect to the polar one, the contact angle of the second water and FBS drops ($\theta'_{water}$ and $\theta'_{FBS}$, respectively) were determined for the three surfaces (see Methods section). Although the surfaces were less wetted than with the first drop, the behavior was practically identical to that described above (Table 2). Thus, the three hydrophilic materials led to very similar $\theta'_{water}$ values while the differences among $\theta'_{FBS}$ values were similar to those obtained for $\theta_{FBS}$.

TABLE 2

Roughness (Rq), contact angle of the first and second water drops ($\theta_{water}$ and $\theta'_{water}$), contact angle of the first and second FBS drops ($\theta_{FBS}$ and $\theta'_{FBS}$), and water content after immersion in deionized water ($M_w$) determined for cHAP/p, cHAp/s and cHAp/tsp samples.

| Sample | Rq (nm) | $\theta_{water}$ (°)/$\theta'_{water}$ (°) | $\theta_{FBS}$(°)/$\theta'_{FBS}$ (°) | $M_w$ (%) |
|---|---|---|---|---|
| cHAp/p | 851 ± 194 | 3 ± 1/6 ± 1 | 81 ± 2/96 ± 2 | — |
| cHAp/s | 863 ± 158 | 4 ± 1/4 ± 1 | 61 ± 2/71 ± 2 | 7 ± 1 |
| cHAp/tsp | 882 ± 92 | 4 ± 1/4 ± 1 | 51 ± 2/62 ± 2 | 13 ± 1 |

In order to complement this information, water absorption assays were performed using the procedure described in the Methods section (Eqn 1). Unfortunately, cHAp/p discs broke immediately after water immersion, no measurement being possible in that case. However, the water content determined for cHAp/s and cHAp/tsp samples after immersion in deionized water, which is displayed in Table 2, were fully consistent with the $\theta_{FBS}$ and $\theta'_{FBS}$ values. Accordingly, water adsorption was 5% higher for HAp/tsp than for HAp/s.

Electrochemical and Electrical Properties

Figure 5:
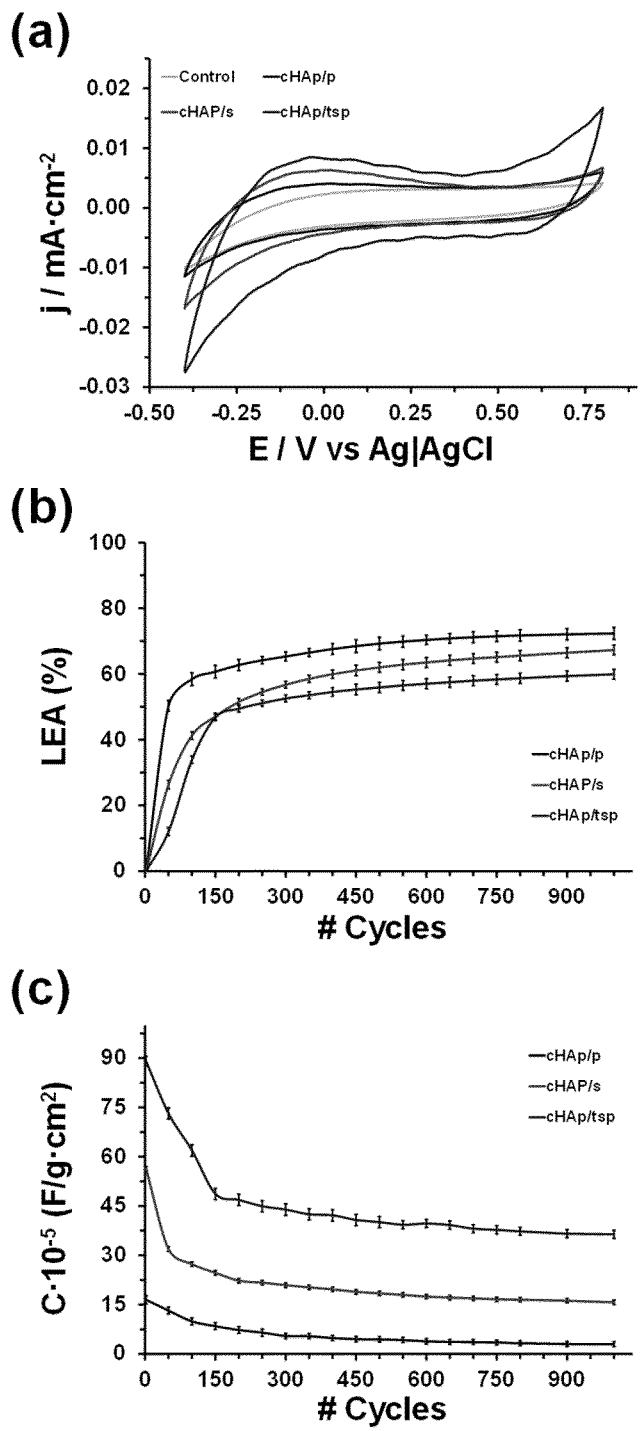
FIG. 5. For cHAp/p, c/HAp/s and cHAp/tsp: (a) control voltammograms and variation of both (b) the loss of electroactivity (LEA in Eqn 2) and (c) the specific capacitance (C in Eqn 3) with the number of consecutive oxidation-reduction cycles in PBS.

Cyclic voltammograms recorded in PBS for cHAp/p, cHAp/s and cHAp/tsp fixed on steel are compared in FIG. 5a. As it can be seen, the electrochemical activity of cHAp/p is higher than that of steel, which was used as a control. However, the electroactivity increases considerably with thermal and electrical treatments (i.e. 46% and 150%, respectively). In the case of cHAp/tsp, such evident effect is accompanied of a significant enhancement of the anodic current intensity at the reversal potential. This behavior suggests that the structural changes provoked by the thermally stimulated polarization treatment facilitate the diffusion of ions through the inorganic matrix and, therefore, the electrochemical response upon oxidation-reduction processes. On the other hand, the current density cHAp/tsp obtained using a polarization temperature range as disclosed herein is several orders of magnitude higher than that achieved by Yamashita and co-workers[14] using a polarization temperature of 350-400° C. (~$10^{-5}$ A/cm² and ~$10^{-9}$ A/cm², respectively), proving the success of our treatment. It is worth noting that this was an unexpected result since Yamashita and coworkers[14] found that the current density decreases in the interval between 450 and 700° C. The success of the inventors' treatment has been attributed to the combination of the sintering temperature, which is lower than that of Yamashita and co-workers[14] and avoids some undesirable phase transitions, and a very high polarization temperature (between 700° C. and 1200° C.).

Treatments also affect the electrostability, as is reflected by the variation of the LEA (Eqn 2) with the number of consecutive oxidation-reduction cycles (FIG. 5b). As it can be seen, in all cases the electrochemical stability decreases rapidly during the first 100-150 redox cycles, the reduction of the LEA being considerably slower along the next cycles. After 1000 cycles, the electroactivity decreased 72%, 67% and 60% for cHAp/p, cHAp/s and cHAp/tsp, respectively, evidencing that structural changes caused by thermally stimulated polarization process also enhances the stability of the electrochemical properties. The behavior followed by the specific capacitance (C in Eqn 3) is fully consistent with that of the electroactivity. Thus, although C is very small in all cases, the ability to store charge of cHAp/p (C=16·$10^{-5}$ F/g·cm²) is 71% and 82% smaller than those of cHAp/s and cHAp/tsp (C=56·$10^{-5}$ and 89·$10^{-5}$ F/g·cm², respectively). The variation of the specific capacitance with the number of redox cycles (FIG. 5c) was similar to that described above for LEA.

Figure 6:
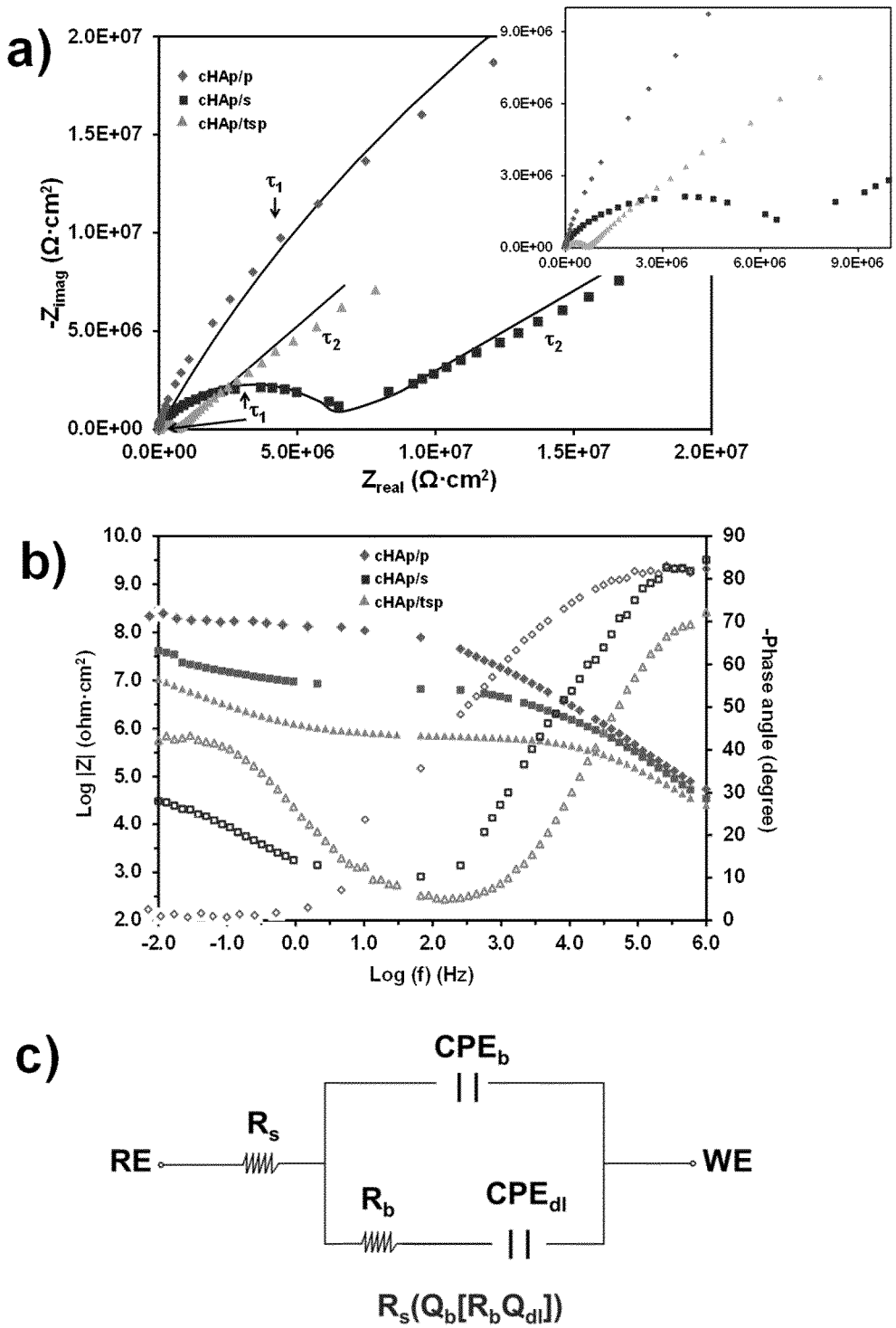
FIG. 6. (a) Nyquist and (b) Bode plots for cHAp/p, cHAp/s and cHAp/tsp. (c) Electrical equivalent circuit (EEC) used to fit the experimental data recorded for cHAp/s and cHAp/tsp: $R_s$ is the electrolyte resistance, $CPE_b$ and $R_b$ are the bulk constant phase element and resistance, respectively, $CPE_{dl}$ is the contribution of the double layer capacitance. Open symbols correspond to phase angle values whereas solid symbols correspond to Log|Z|, and black lines correspond to the fitted profile. Inset in figure a) represents the Nyquist behavior at high frequency.

EIS measurements were carried out to evaluate the ionic conductivity inside the prepared HAp samples. Thus, this technique will provide information about the influence in the electrical properties of the inner interfaces created inside the material by the thermally stimulated polarization process. FIG. 6 compares representative Nyquist plots obtained for cHAp/p, cHAp/s and cHAp/tsp. In a Nyquist plot, the first semi-circular response corresponds to the electron transfer resistance at the higher frequency range, which controls the electron transfer kinetics of the redox probe on the electrode-solid disk interface. The diameter of the semi-circle defines the resistance of electron transfer, usually called bulk resistance ($R_b$). The Nyquist plot recorded for cHAp/p (FIG.

6a) exhibits only one dielectric relaxation time (τ), which corresponds to a single charge transfer across the solid disk, indicating that the material has a high bulk resistance (i.e. low ionic conductivity) in the dry state. Bode plots (FIG. 6b) show phase angles close to 80°, which correspond to resistive materials in the dry state. The semi-circle diameter in Nyquist plots (FIG. 6a) is considerably smaller for cHAp/s and, especially, for cHAp/tsp, even though a second time constant appears. This feature has been attributed to a significant structural modification inside the HAp crystals that allows fast transport of charge across the disk. According to WAXD and SEM observations, cHAp/s and cHAp/tsp samples present higher more concentration of crystals as well as bigger crystals than cHAp/p. Therefore, the thermal treatment step promotes the growing of the crystal, while the thermally stimulated polarization treatment is that responsible is responsible of the definition of good pathways for charge transportation. This is reflected in the numerical evaluation of the EIS results (Table 3).

creation of charge pathways inside the solid, which is reflected by the $CPE_b$. The last observation is in perfect agreement with both SEM micrographs and the electrochemical response determined by CV. According to Chaudhuri and co-workers,[49] the conductive sites in dry HAp should be considered as the channels along which ions are able to move by thermally activated hopping (such as the columnar $OH^-$ ions or protons) while the capacitive sites are immobile ions. In contrast, Lukic et al.,[50] who found that the conductivity of HAp increases with temperature, attributed this behavior to geometric factors as growing of grain size. Liu and Shen[51] showed extensive dehydroxylation during the sintering of cHAp above 900° C., $OH^-$ ions being responsible of the conductivity at high temperatures (i.e. in the range of 700-1000° C.).

Adsorption of Pyrophosphate, Triphosphate and Trisphosphonate

In a very recent study we examined the adsorption of $P_2O_7^{4-}$, polyP and amino-ATMP onto cHAp/p.[12] In order to

TABLE 3

Data of EIS results obtained from the electrical equivalent circuit (EEC) showed in the FIG. 6c for cHAp/s and cHAp/tsp dry discs[a] after exposure to several treatment processes and after the phosphates inorganic molecules adsorption.

| Samples | $R_b$ ($\Omega\ cm^2$) | $Q_{dl}$ (F $cm^{-2}\ s^{n-1}$) | n | $Q_b$ (F $cm^{-2}\ sn^{-1}$) | n |
|---|---|---|---|---|---|
| cHAp/p [a] | $134.6 \times 10^{-6}$ | — | — | $8.180 \times 10^{-10}$ | 0.76 |
| cHAp/s | $6.43 \times 10^{-6}$ | $1.248 \times 10^{-8}$ | 0.77 | $1.215 \times 10^{-5}$ | 0.44 |
| cHAp/tsp | $0.67 \times 10^{-6}$ | $4.558 \times 10^{-7}$ | 0.71 | $4.863 \times 10^{-5}$ | 0.55 |
| cHAp/s + polyp | $0.42 \times 10^{-6}$ | $5.076 \times 10^{-8}$ | 0.81 | $1.573 \times 10^{-5}$ | 0.43 |
| cHAp/s + $P_2O_7^{4-}$ | $1.00 \times 10^{-6}$ | $3.647 \times 10^{-8}$ | 0.73 | $1.309 \times 10^{-5}$ | 0.50 |
| cHAp/s + ATMP | $0.95 \times 10^{-6}$ | $2.159 \times 10^{-8}$ | 0.76 | $1.009 \times 10^{-5}$ | 0.42 |
| cHAp/tsp + polyp | $66.7 \times 10^{-3}$ | $5.550 \times 10^{-8}$ | 0.81 | $7.792 \times 10^{-4}$ | 0.63 |
| cHAp/tsp + $P_2O_7^{4-}$ | $0.35 \times 10^{-6}$ | $1.373 \times 10^{-8}$ | 0.79 | $3.812 \times 10^{-5}$ | 0.49 |
| cHAp/tsp + ATMP | $69.9 \times 10^{-3}$ | $5.699 \times 10^{-8}$ | 0.73 | $5.204 \times 10^{-5}$ | 0.48 |

[a] The EEC for cHAp/p is $R_s(R_bQ_b)$.

The electrical equivalent circuit (EEC) used to fit the experimental data is shown in FIG. 6c. The EEC contains three important elements: $R_b$ that represents the bulk resistance; and $Q_b$ and $Q_{dl}$ that describes the ideal capacitances from both the cHAp thick film and double layer between the metal-disk surfaces, respectively. $R_s$ corresponds to the electrolyte solution resistance, even though it was considered ~0 $\Omega\cdot cm^2$ due to the absence of liquid electrolyte. The $CPE_b$ real capacitance accounts for the non-uniform diffusion among the films adhered to the electrode surface. The $CPE_{dl}$ real capacitance is typically associated to the surface reactivity, surface heterogeneity and roughness, which in turn are related to the electrode geometry and porosity. Also, the CPE impedance, which has been expressed as $Z_{CPE}=[Q(j\omega)^n]^{-1}$, represents an ideal capacitor and a pure resistor for n=1 and n=0, respectively, while it is associated with a diffusion process when n~0.5. All impedance data displayed in FIG. 6a were fitted with the EEC showed in the FIG. 6c, with exception of those obtained for cHAp/p. For EEC used the latter samples does not have the capacitance response from the double layer film and corresponds to $[R_s(R_bQ_b)]$.

According to Table 3, the $R_b$ is very low ($6.7 \times 10^5\ \Omega\cdot cm^2$) for the cHAp/tsp sample compared to the cHAp/s one ($6.4 \times 10^6\ \Omega\cdot cm^2$), which indicates that the ionic conductivity increased by one order of magnitude when the thermal treatment is combined with the polarization one. Another relevant change is the appearance of a second time constant (τ) when larger crystals were obtained and these crystals were polarized at 500 V (FIG. 6a). This feature indicates the examine how both thermal and electric treatments affect the adsorption of the same inorganic compounds, a complete study has been carried using cHAp/s and cHAp/tsp samples as substrates. According to our previous work, the concentration of adsorbate in the working solutions was 100 mM for $P_2O_7^{4-}$ and 200 mM for both polyP and ATMP, which provided clear adsorption signals for cHAp/p at pH 7.

Figure 7:
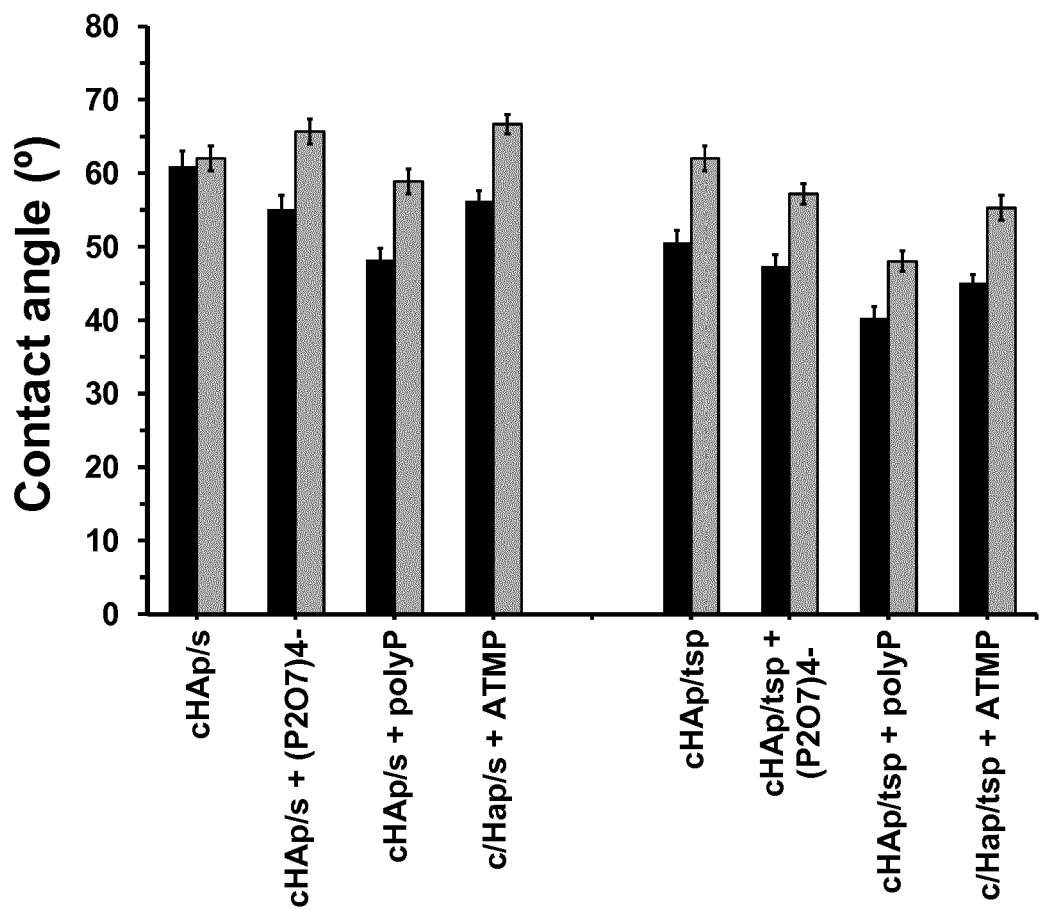
FIG. 7. Contact angle of the first and second FBS drops ($\theta_{FBS}$ and $\theta'_{FBS}$ in black and grey, respectively) for cHAp/s and cHAp/tsp samples before and after incubation in presence of $P_2O_7^{4-}$, polyP and ATMP.

FIG. 7a compares the contact angles for both the first and second FBS drop ($\theta_{FBS}$ and $\theta'_{FBS}$, respectively) determined for cHAp/s and cHAp/tsp before and after incubation in presence of the inorganic adsorbates. As it can be seen, the FBS-wettability of the two substrates increased upon incubation, suggesting that the three inorganic adsorbates were successfully adsorbed. Moreover, the reduction of the contact angle with the adsorbate followed the same variation for the two cHAp substrates: polyP<$P_2O_7^{4-}$≈ATMP.

Accordingly, the surface energy becomes higher upon the adsorption of polyP than upon the adsorption of $P_2O_7^{4-}$ and ATMP, independently of the treatment applied to the cHAp particles.

Figure 12:
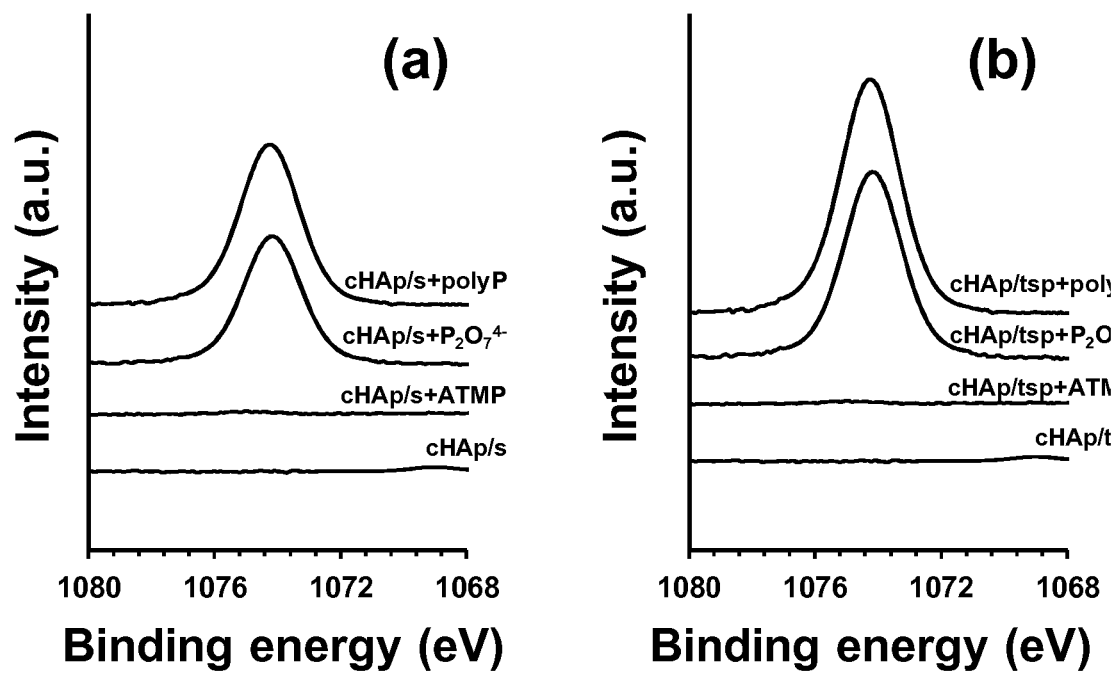
FIG. 12. High-resolution XPS spectrum in the Na1s region for (a) cHAp/s and (b) cHAp/tsp samples before and after incubation in presence of ATMP, $P_2O_7^{4-}$ and polyP.
Figure 13:
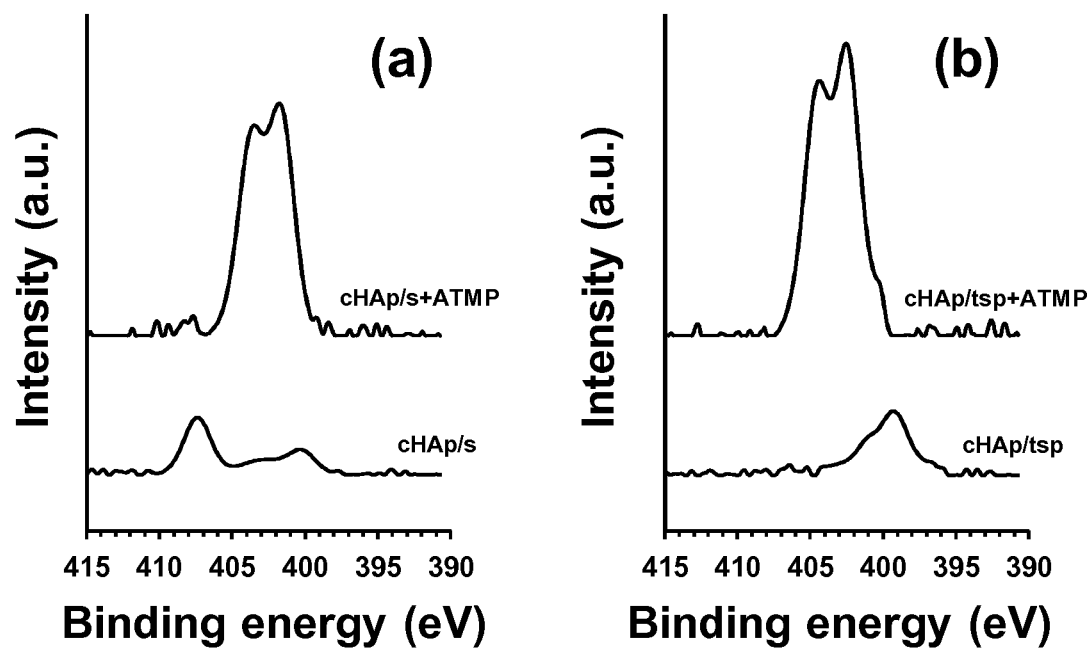
FIG. 13. High-resolution XPS spectrum in the N1s region for (a) cHAp/s and (b) cHAp/tsp samples before and after incubation in presence of ATMP.

Adsorption of $P_2O_7^{4-}$, polyP and ATMP was also examined by using XPS. Comparison of the characteristic XPS spectrum in the Na1s region for cHAp/s and cHAp/tsp before and after incubation in presence of inorganic adsorbates reveals a peak centered at 1074.2 eV for samples treated with $P_2O_7^{4-}$ and polyP (FIG. 12). This signal, which is identical to those reported by Gaskell et al.[52,53] for $Na_4P_2O_7\cdot 10H_2O$ and $Na_5P_3O_{10}$, corroborates the incorporation of these compounds onto the surface of the two treated cHAp. In contrast the content of Na in non-incubated samples and samples incubated in presence of ATMP is null (Table 1). The ratios obtained using the Na1s atomic percent compositions indicate that the adsorption of $P_2O_7^{4-}$ and polyP is, respectively, ~2 and ~1.5 times higher for cHAp/tsp than for cHAp/s. A similar strategy was followed to identify the adsorption of ATMP, which is clearly detected through the peaks at the $N_1s$ region (Figure S4). Thus, the content of N in non-incubated samples and samples incubated in presence of $P_2O_7^{4-}$ and polyP is 0.40 wt. %, increasing to 3.18 and 4.08 wt. % for cHAp/s and cHAp/tsp samples incubated in presence of ATMP (Table 1). Assuming that the amount of $N_2$ adsorbed from the atmosphere is the same for incubated and non-incubated samples, the adsorption of ATMP is ~1.4 times higher for cHAp/tsp than for cHAp/s. The two peaks detected at 404.3 and 402.5 eV (FIG. 13) for the latter samples have been attributed to nitrogen atoms of ATMP with different chemical environments (i.e. free and hydrogen bonded).[54]

Figure 8:
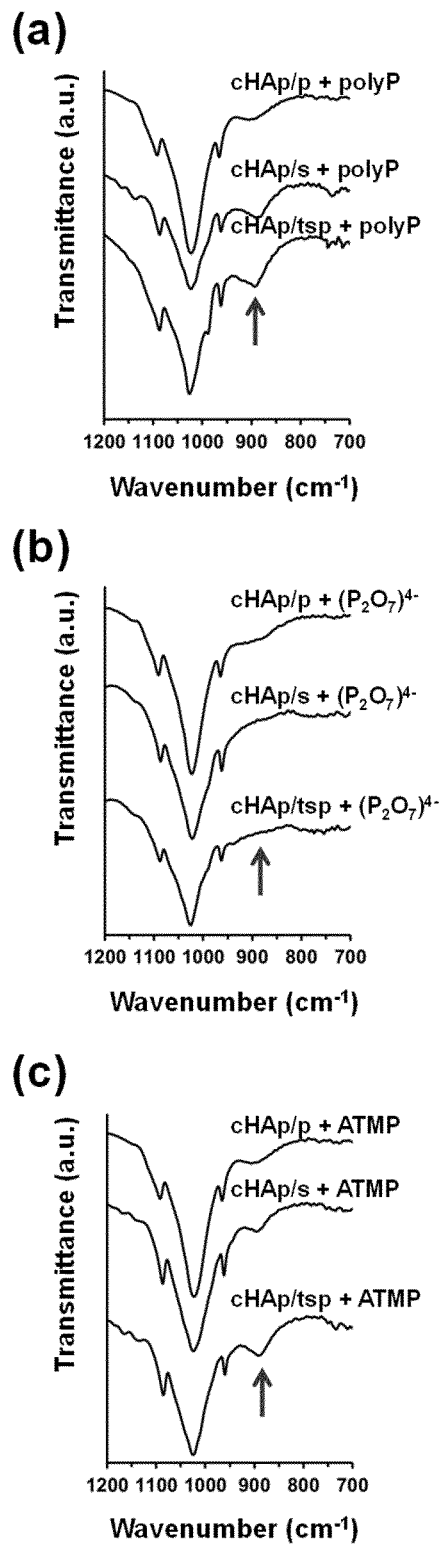
FIG. 8. FTIR spectra of cHAp/p, cHAp/s and cHAp/tsp incubated in presence of (a) polyP (200 mM), (b) $P_2O_7^{4-}$ (100 mM) and (c) ATMP (200 mM) at pH 7. Arrows indicate the position of the bands and shoulder used to identify the adsorption of the different adsorbates.

FIG. 8 compares the FTIR spectra of cHAp/p, cHAp/s and cHAp/tsp after incubation in solution with $P_2O_7^{4-}$, polyP and ATMP at neutral pH. FTIR spectra of $P_2O_7^{4-}$, polyP and ATMP were reported in our previous work.[12] For polyP, the weak shoulder identified at around 890 cm$^{-1}$ for cHAp/p (FIG. 8*a*), which corresponds to the P—O—P asymmetric stretching, transforms into a well-defined adsorptions band for cHAp/s and, especially, cHAp/tsp. This feature is fully consistent with XPS observation, corroborating that the application of thermal and thermally stimulated polarization processes enhance significantly the ability of cHAp to adsorb polyP. Based on the FTIR spectra presented in FIGS. 1 and 8, the ability of cHAp samples to adsorb polyP was estimated using the ratio of integrated area of the peak at 1016 cm$^{-1}$ (belonging to the mineral) and the integrated area of the peak at 890 cm$^{-1}$ (belonging to polyP). Results indicated that the adsorption of polyP onto cHAp/p was 2.0 and 2.6 times lower than onto cHAp/s and cHAp/tsp, respectively, which is in good agreement with XPS results.

Unfortunately, this feature was much less clear for $P_2O_7^{4-}$. Thus, the band at 890 cm$^{-1}$ remained undetectable in the spectra displayed in FIG. 8*b*, where the only evidence of adsorption is the very weak shoulder at 740-750 cm$^{-1}$ for cHAp/s and cHAp/tsp that has been attributed to the P—O—P symmetric stretching. It should be noted that the atomic percent content of Na1s detected by XPS in cHAp samples incubated with polyP is considerably higher than in those incubated with $P_2O_7^{4-}$ (Table 1), which is consistent with FTIR observations. Also, previous quantum mechanical calculations considering the (100) and (001) surfaces of cHAp evidenced that the adsorption of polyP is favored with respect to that of $P_2O_7^{4-}$.[18] Thus, the ability of the adsorbate to adapt its geometry to the crystallographic positions of the ions at the cHAp surfaces increases with the size of phosphate chain. Therefore, adsorbed $P_2O_7^{4-}$ was found to be significantly strained in comparison to adsorbed polyP.

FTIR results for the different cHAp samples incubated with ATMP (FIG. 8*c*) reveals similar trends to those observed for polyP. Thus, the shoulder identified for cHAp/p at 900 cm$^{-1}$, which corresponds to asymmetric vibrations of alkylphosphonic,[55] transforms into a relatively intense and well defined peak for cHAp/s and, especially, cHAp/tsp. This variation is in agreement with XPS results, indicating that the ability of the different cHAp samples to adsorb ATMP increase in the following way: cHAp/p<cHAp/s<cHAp/tsp. The adsorption of ATMP onto of cHAp/s and cHAp/tsp was estimated to be, respectively, 2.2 and 3.0 times higher than onto cHAp/p, supporting XPS data.

Figure 9:
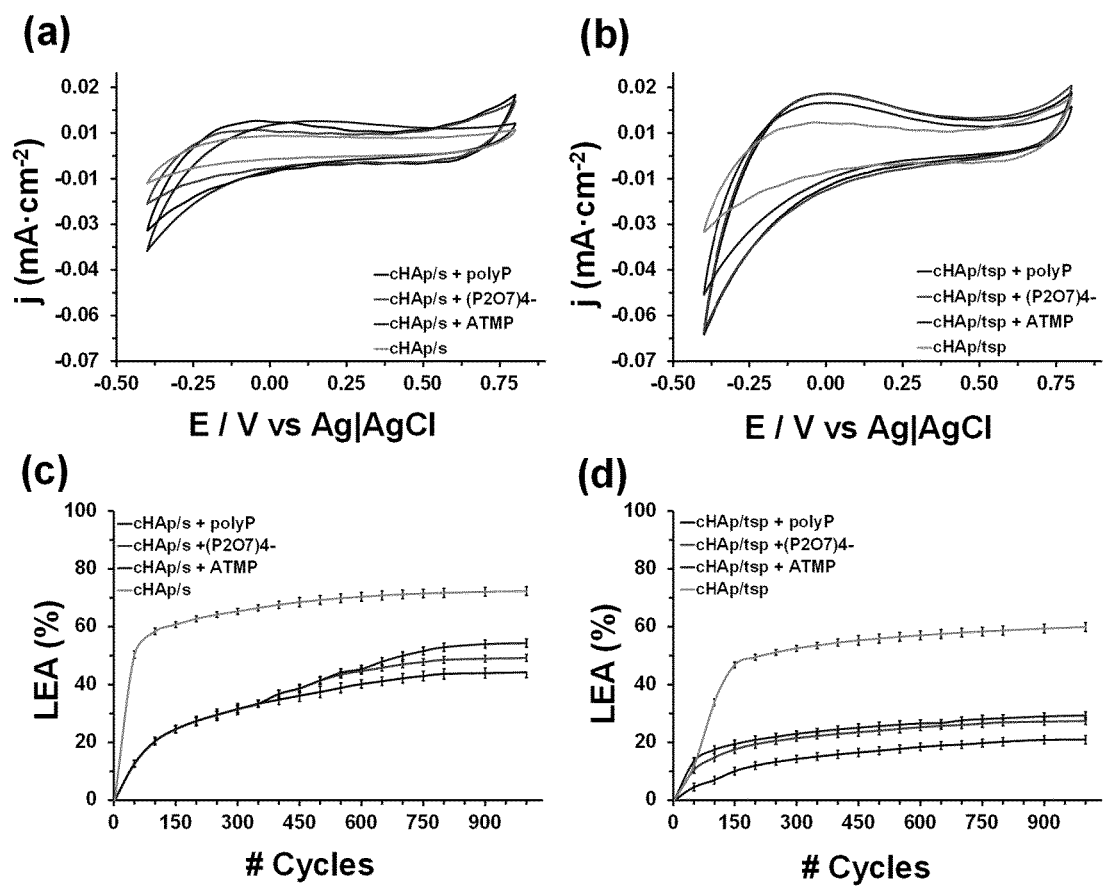
FIG. 9. For (a and c) cHAp/s and (b and d) cHAp/tsp: (a and b) control voltammograms and (c and d) variation of the loss of electroactivity (LEA in Eqn 2) with the number of consecutive oxidation-reduction cycles in PBS for samples non-incubated and incubated in presence of $P_2O_7^{4-}$, polyP and ATMP.
Figure 14:
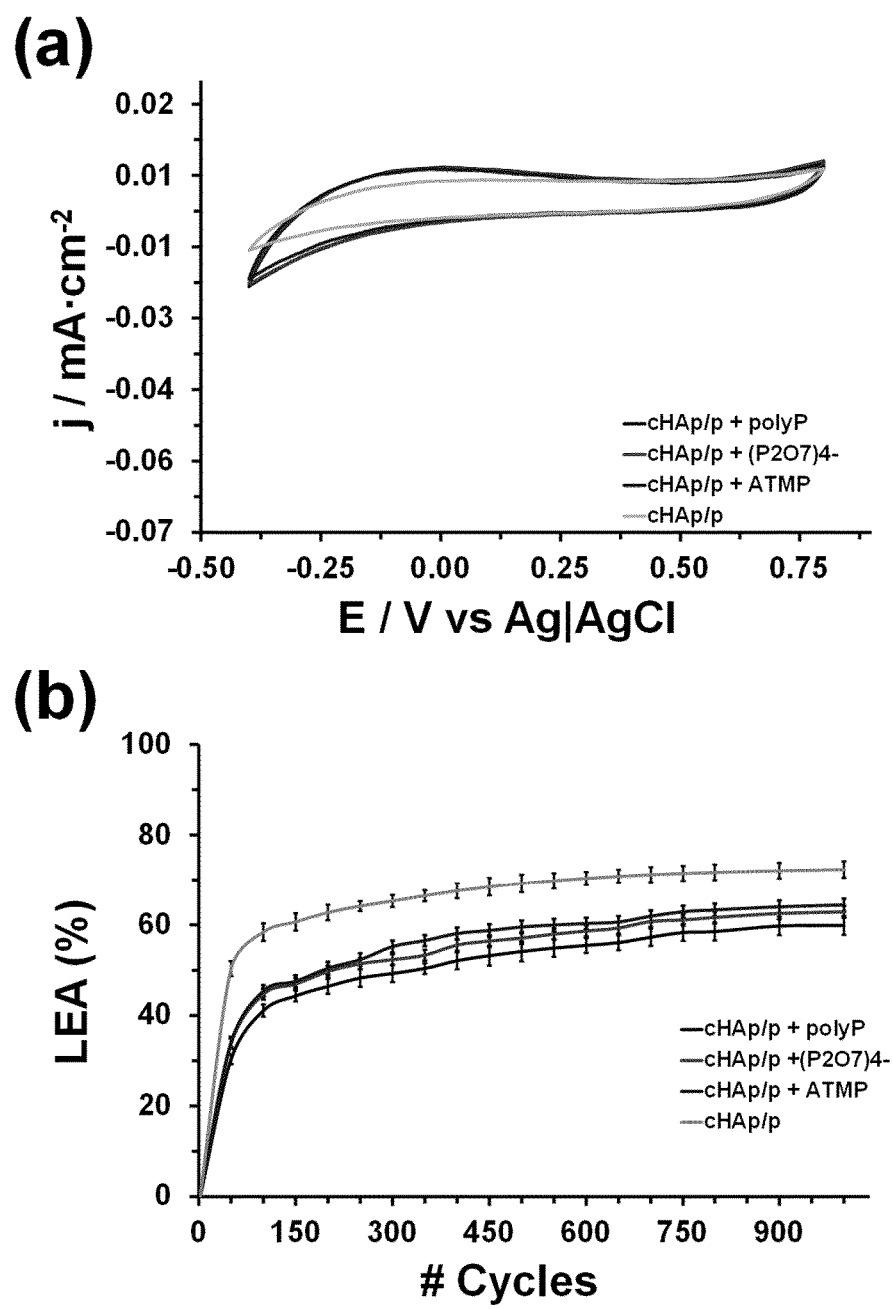
FIG. 14. For cHAp/p: (a) control voltammogram and (b) variation of the loss of electroactivity (LEA in Eqn 2) with the number of consecutive oxidation-reduction cycles in PBS for samples non-incubated and incubated in presence of $P_2O^{4-}$, polyP and ATMP.

Adsorption-Induced Electrochemical Protection and Enhanced Electrical Conductivity Cyclic voltammograms recorded for cHAp/p incubated in presence of polyP, $P_2O_7^{4-}$ and ATMP (FIG. 14*a*) are very similar to those displayed in FIG. 5*a*, suggesting that the amount of adsorbate at the mineral surface is not enough to alter the redox behavior. In contrast, cyclic voltammograms of incubated cHAp/s and, especially, cHAp/tsp are considerably different from those of non-incubated samples. This is clearly reflected in FIGS. 9*a* and 9*b*, which compares the voltammograms recorded for incubated and non-incubated samples. Thus, the electroactivity of incubated cHAp/s and cHAp/tsp samples is higher than that of non-incubated samples by ~60% and ~40%, respectively, suggesting that adsorbed molecules facilitates the exchange of ions between the mineral matrix and the PBS electrolyte solution during the oxidation and reduction processes.

However, the most striking feature refers to the variation of the electroactivity against the number of redox cycles. Thus, comparison of the LEA (Eqn 2) measured for incubated and non-incubated cHAp/p (FIG. 14*b*) indicates that the electrochemical stability of the latter is lower (~10%) than that of samples with adsorbed polyP, $P_2O_7^{4-}$ or ATMP. This feature, which suggests that adsorbate molecules provide electrochemical protection to the mineral, is significantly enhanced for cHAp/s and cHAp/tsp, as is evidenced in FIGS. 9*c* and 9*d*, respectively. Thus, after 1000 redox cycles the loss of electroactivity of non-incubated cHAp/s and cHAp/tsp is higher than those of incubated samples by ~20% and ~25%, respectively. The LEA values of incubated cHAp/tsp are particularly striking (i.e. 21%, 27% and 29% for polyP, $P_2O_7^{4-}$ and ATMP, respectively). These low values evidence that the application of the thermally stimulated polarization treatment enhances not only the adsorption capacity but also improves the electrochemical activity and stability.

Figure 15:
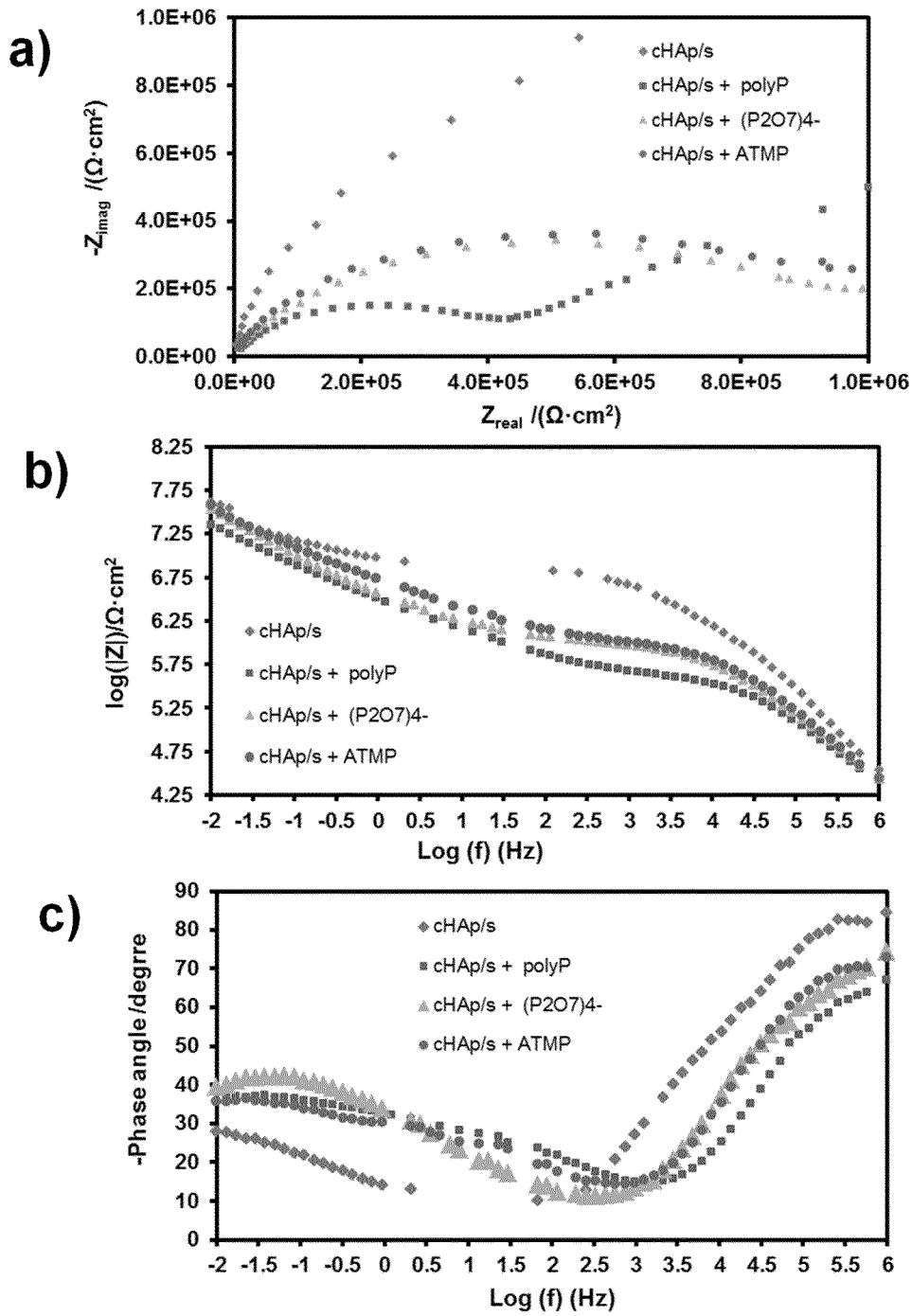
FIG. 15. a) Nyquist, (b) log |Z| and (c) phase angle plots for cHAp/s alone and incubated in presence of polyP (200 mM), $P_2O_7^{4-}$ (100 mM) and (c) ATMP (200 mM) at pH 7.
Figure 16:
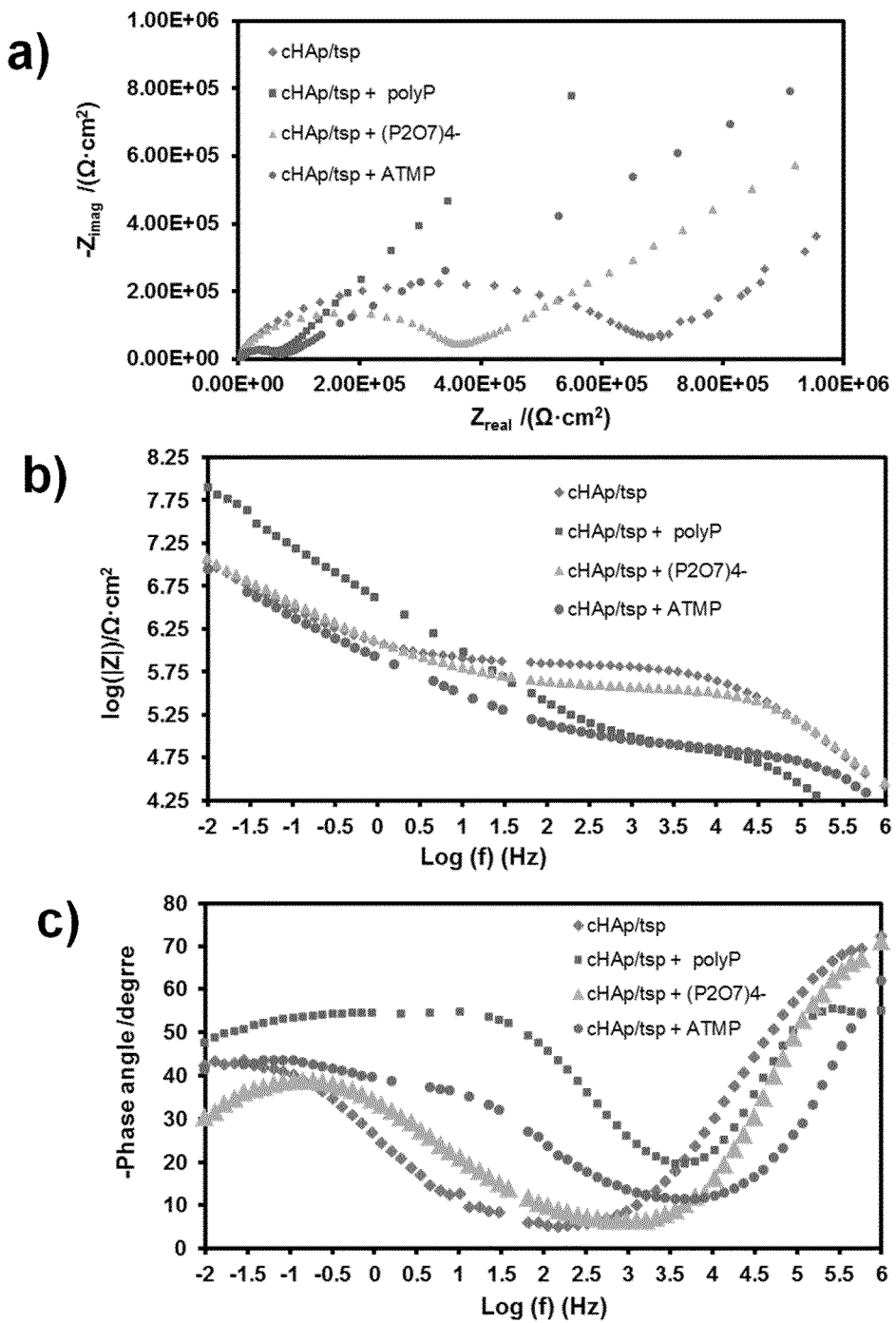
FIG. 16. a) Nyquist, (b) log |Z| and (c) phase angle plots for cHAp/tsp alone and incubated in presence of polyP (200 mM), $P_2O_7^{4-}$ (100 mM) and (c) ATMP (200 mM) at pH 7.
Figure 17:
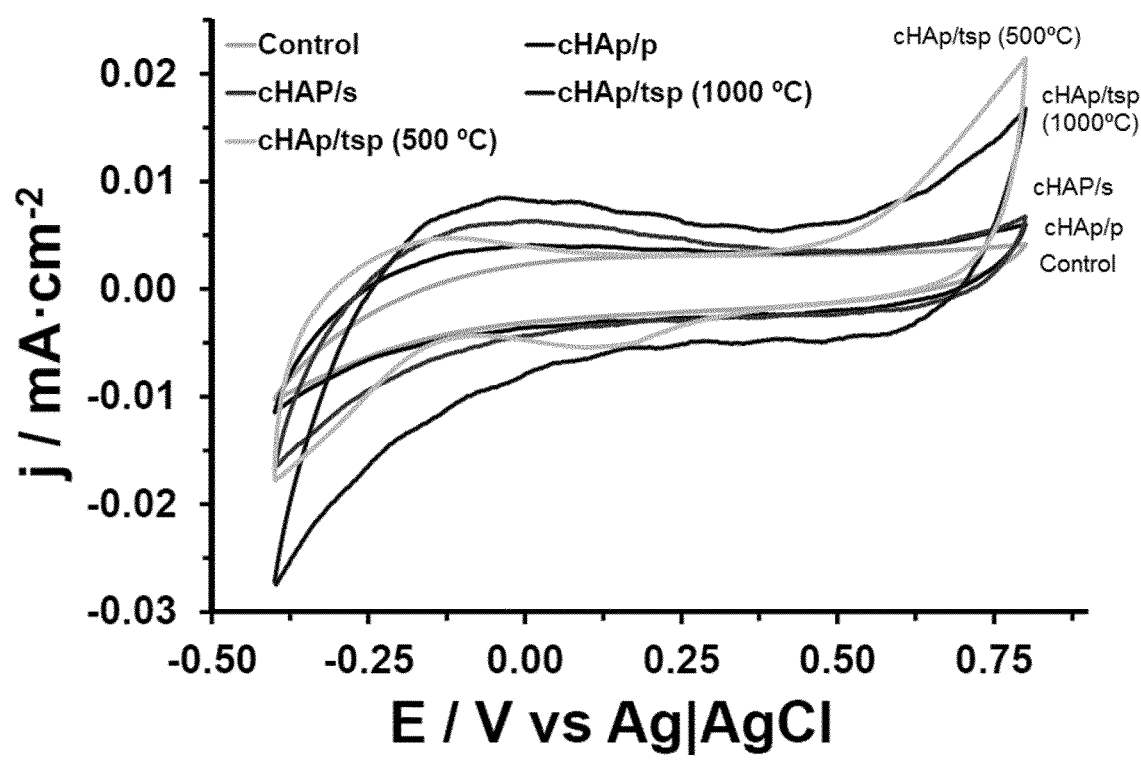
FIG. 17 FIG. 17 shows the control voltammograms for cHAp/p, c/HAp/s and cHAp/tsp in PBS. The electrochemical activity, which is defined by the anodic and cathodic areas of the voltammogram, is noticeably higher for HAp/tsp than for HAp/s and HAp/p and the control (stainless steel, AISI 304, electrode).

EIS results (Table 3) reflect the positive effects of adsorbed PolyP and ATMP in the ionic conductivity of treated cHAp samples in comparison to adsorbed $P_2O_7^{4-}$. This phenomenon is particularly remarkable for cHAp/tsp, which display the lowest bulk resistance (66.7 and 69.9 kΩ·cm$^2$ for samples with adsorbed PolyP and ATMP, respectively), evidencing that PolyP and ATMP promote the electron charge mobility inside the dry film. Thus, structural changes produced by the thermally stimulated polarization treatment favors the interaction of the mineral with both PolyP and ATMP, forming better charge transfer channels. The alignment of the OH$^-$ ions along the c-axis in cHAp/tsp samples seems to play a crucial role in the formation of such interaction. FIGS. 15 and 16 compare the Nyquist and Bode plots recorded for cHAp/s and cHAp/tsp, respectively, with the three examined adsorbates.

Particular Use of Permanently Polarized Hydroxyapatite as a Catalyst Component in the Synthesis of Amino Acids Synthesis of Amorphous (aHAp) and Crystalline Hydroxyapatite (cHAp)

15 mL of 0.5 M $(NH_4)_2HPO_4$ in de-ionized water (pH adjusted to 11 with an ammonia 30 w/w-% solution) were added drop-wise (rate of 2 mL·min$^{-1}$) and under agitation (400 rpm) to 25 mL of 0.5 M $Ca(NO_3)_2$ in ethanol. After that, the reaction mixture was stirred 1 h by agitation (400 rpm) at room temperature. The suspension was aged for 24 h at 37° C. to get aHAP, whereas a hydrothermal treatment (200 bar at 150° C. for 24 h) was subsequently applied to get cHAp. The precipitate was separated by centrifugation and washed sequentially with de-ionized water and a 60/40 v/v mixture of ethanol-water (twice). A white powder with the theoretical Ca/P ratio of 1.67 was recovered after freeze-drying.

Sintering Process aHAp, cHPAp and montmorillonite powders were subsequently sintered by firstly heating them in a laboratory furnace (Carbolite ELF11/6B/301) at 1000° C. during 2 h at an air atmosphere and finally uniaxially pressed at 620 MPa for 10 min. Discs of 100 mm of diameter and 1.7 mm of thickness were finally obtained.

Thermally Stimulated Polarization Process

In order to get thermally stimulated polarized HAp, Nanofil 757 and LM systems, the corresponding discs samples were sandwiched between stainless steel (AISI 304) plates, heated in the furnace to 1000° C. in air and, simultaneously, polarized for 1 h under application of a constant DC voltage of 500 V, which was previously reported as the optimal one for adsorption assays performed with polarized HAp.[2] Polarized samples will be named as p-cHAp, p-aHAp, p-$N_{757}$ and p-LM. It should be pointed out that HAp could not be polarized if the sample was not previously sintered since the disk had not the sufficiently consistence and broke during the polarization process.

Deposition of Phosphonate and Zirconium Oxychloride ($ZrOCl_2$) Layers

A trilayered system consisting in the successive deposition of ATMP, Zirconium oxychloride and ATMP layers onto the appropriate substrate (i.e. mica, sintered aHAp and cHAp or silicate before and after being submitted to the polarization process) was obtained by immersion in the corresponding aqueous solutions at room temperature for 5 h. Concentrations of ATMP solutions to get the first and second AMTP layers were 5 mM and 1.25 mM, respectively, whereas the concentration of *Zirconium oxychloride* was varied in the different experiments (i.e. from 1 mM to 10 mM, respectively). After each immersion the samples were dried at 37° C. for 3 h. Fort the sake of completeness bilayered and monolayered systems (i.e. Phos-ZC, Phos, ZC) were also considered.

Synthesis of Amino Acids

A high pressure stainless steel reactor was employed to perform the synthesis of amino acids (AAs). The designed reactor was dotted with a manometer, an electric heater with a thermocouple and an external temperature controller. The reactor was also characterized by an inert reaction chamber of teflon (120 mL) where catalyst and water were incorporated, three independent inlet valves for $N_2$, $CH_4$, $CO_2$ and an outlet valve to recover the gaseous reaction products. An UV lamp (GPH265T5L/4, 253.7 nm) was also placed in the middle of the reactor to irradiate directly the solid sample, being the lamp protected by a UV transparent quartz tube. This was coated with a thin film of teflon in order to avoid any contact between the reaction medium and the silicate and therefore to discard other catalyst effects.

Reactions were performed in the 75-105° C. temperature range for reaction times between 2 and 96 h. Solid samples weighted approximately 150 mg and 0.5 mL of de-ionized liquid water were initially incorporated in the reaction chamber if it was considered necessary. The chamber was extensively purged with the first selected gas in order to eliminate the initial air content (i.e. $N_2$ or $CO_2$). Each selected gas was introduced to increase the reaction chamber pressure (measured at room temperature) in two or three atmospheres (i.e. the final pressure at room temperature was always 6 bar).

Measurements

Synthesis of amino acids was routinely verified by the ninhydrin (2,2-dihydroxyindane-1,3-dione) detection test for primary amines. To this end 0.5 mg of the solid recovered after reaction was immersed in a tube containing 0.2 w/v-% solution of ninhydrin in acetone and subsequently heated to 75° C. in an oven. The development of purple coloured solutions indicated the formation of the 2-(1,3-dioxoindan-2-yl)iminoindane-1,3-dione chromophore. Yellow-orange coloured solutions were on the contrary characteristic of the Schiff base generated by reaction with secondary amines, while uncoloured solutions derived from tertiary amines such as ATMP.

NMR spectra were acquired with a Bruker Avance III-400 spectrometer operating at frequencies of 400.1 MHz, 100.6, and 161.9 for $^1H$, $^{13}C$ and $^{31}P$, respectively. Chemical shifts for $^1H$ and $^{13}C$ were calibrated using tetramethylsilane as an internal standard. Samples were dissolved in deuterated water containing 100 mM of HCl and 50 mM of NaCl.

X-ray photoelectron spectroscopy (XPS) analyses were performed in a SPECS system equipped with a high-intensity twin-anode X-ray source XR50 of Mg/Al (1253 eV/1487 eV) operating at 150 W, placed perpendicular to the analyzer axis, and using a Phoibos 150 MCD-9 XP detector. The X-ray spot size was 650 μm. The pass energy was set to 25 and 0.1 eV for the survey and the narrow scans, respectively. Charge compensation was achieved with a combination of electron and argon ion flood guns. The energy and emission current of the electrons were 4 eV and 0.35 mA, respectively. For the argon gun, the energy and the emission current were 0 eV and 0.1 mA, respectively. The spectra were recorded with pass energy of 25 eV in 0.1 eV steps at a pressure below $6 \times 10^{-9}$ mbar. These standard conditions of charge compensation resulted in a negative but perfectly uniform static charge. The C1s peak was used as an internal reference with a binding energy of 284.8 eV. High-resolution XPS spectra were acquired by Gaussian-Lorentzian curve fitting after s-shape background subtraction. The surface composition was determined using the manufacturer's sensitivity factors.

Scanning electron microscopy (SEM) studies were carried out using a Focused Ion Beam Zeiss Neon40 microscope operating at 5 kV, equipped with an energy dispersive X-ray (EDX) spectroscopy system. Samples were deposited on a silicon disc mounted with silver paint on pin stubs of aluminum, and sputter-coated with a thin layer of carbon to prevent sample charging problems.

Infrared absorption spectra were recorded with a Fourier Transform FTIR 4100 Jasco spectrometer in the 1800-700 cm' range. A Specac model MKII Golden Gate attenuated total reflection (ATR) equipment with a heating Diamond ATR Top-Plate was used. X-ray powder diffraction patterns were obtained in the beamline BL11-NCD at ALBA synchrotron (Cerdanyola del Valles, Barcelona, Spain), by using a wavelength of 0.100 nm and an WAXS LX255-HS detector from Rayonix which was calibrated with diffractions of standard of a $Cr_2O_3$ sample.

Results Samples coming from reactions using the Phos-ZC-Phos trilayered catalyst supported onto polarized cHAp and a reducing atmosphere constituted by $N_2$, $CO_2$, $CH_4$ and $H_2O$ (set 1 in Table 4) gave rise to positive ninhydrin tests, suggesting therefore the formation of primary amines. In fact, purple spots were developed inside the recovered solids after reaction, indicating that amine compounds were mainly absorbed into the solid substrate. These compounds were well dissolved in the acetone solution after vigorous stirring, contrasting with the uncolored solid/solutions observed for other assayed reaction conditions (e.g. set 2 and sets 4 to 13 in Table 4).

Results plotted in FIG. 20a allow deducing that glycine is firstly produced and alanine is subsequently derived from this simple amino acid. Thus, the Gly/Ala ratio decreases

TABLE 4

Summary of experiments and results attained for the synthesis of amino acids (AAs).[a]

| Set | Conditions[a] | Ninhidrine test | Observations |
|---|---|---|---|
| 1 | p-cHAp/Phos-ZC-Phos $N_2$, $CH_4$, $CO_2$, $H_2O$/UV | + | Gly and Ala signals in NMR spectra. Increasing AAs/Phos ratio with reaction time. Increasing AAs/Phos ratio with reaction T. Increasing AA/Phos ratio with Zr content. |
| 2 | p-cHAp/Phos-ZC-Phos $N_2$, $CH_4$, $CO_2$, $H_2O$ | − | UV radiation is fundamental. |
| 3 | p-aHAp/Phos-ZC-Phos $N_2$, $CH_4$, $CO_2$, $H_2O$/UV | + | The crystalline structure of HAp is not fundamental for reaction. |
| 4 | cHAp/Phos-ZC-Phos $N_2$, $CH_4$, $CO_2$, $H_2O$/UV | − | Polarization of HAp is fundamental. |
| 5 | p-N757/Phos-ZC-Phos $N_2$, $CH_4$, $CO_2$, $H_2O$/UV | − | The type of polarized support is important. |
| 6 | p-LM/Phos-ZC-Phos $N_2$, $CH_4$, $CO_2$, $H_2O$/UV | − | The type of polarized support is important. |
| 7 | p-cHAp/Phos-ZC $N_2$, $CH_4$, $CO_2$, $H_2O$/UV | − | The trilayered system is fundamental. |
| 8 | p-cHAp/ZC-Phos $N_2$, $CH_4$, $CO_2$, $H_2O$/UV | − | The trilayered system is fundamental. |
| 9 | p-cHAp/Phos $N_2$, $CH_4$, $CO_2$, $H_2O$/UV | − | The trilayered system is fundamental. |
| 10 | p-cHAp/ZC $N_2$, $CH_4$, $CO_2$, $H_2O$/UV | − | The trilayered system is fundamental. |
| 11 | Phos | − | AAs cannot be derived from a simple decom-position of Phos using ZC as catalyst. |
| 12 | Phos-Zr $N_2$, $CH_4$, $CO_2$, $H_2O$/UV | − | AAs cannot be derived from a simple decomposition of Phos. |
| 13 | p-cHAp/Phos-ZC-Phos $CH_4$, $CO_2$, $H_2O$/UV | − | Substrate is able to fix molecular nitrogen. Molecular nitrogen is essential. |
| 14 | p-aHAp/Phos-ZC-Phos $N_2$, $CO_2$, $H_2O$/UV | − | $CH_4$ appears as the carbon source for $CH_2$ and $CH_3$ groups. |
| 15 | p-cHAp/Phos-ZC-Phos $N_2$, $CH_4$, $H_2O$/UV | − | $CO_2$ appears as the source for carboxylic groups. |
| 16 | p-cHAp/Phos-ZC-Phos $N_2$, $CH_4$, $CO_2$/UV | − | $H_2O$ plays an important role in the . . . mechanism. |

[a]Abbreviations denote the support (p-aHAp, aHAp, p-N757, p-LM) and the order of the different layers deposited onto its surface (Phos and ZC for phosphonate and Zirconium oxychloride, respectively). UV indicates that experiments were performed under UV radiation.

Figure 19A:
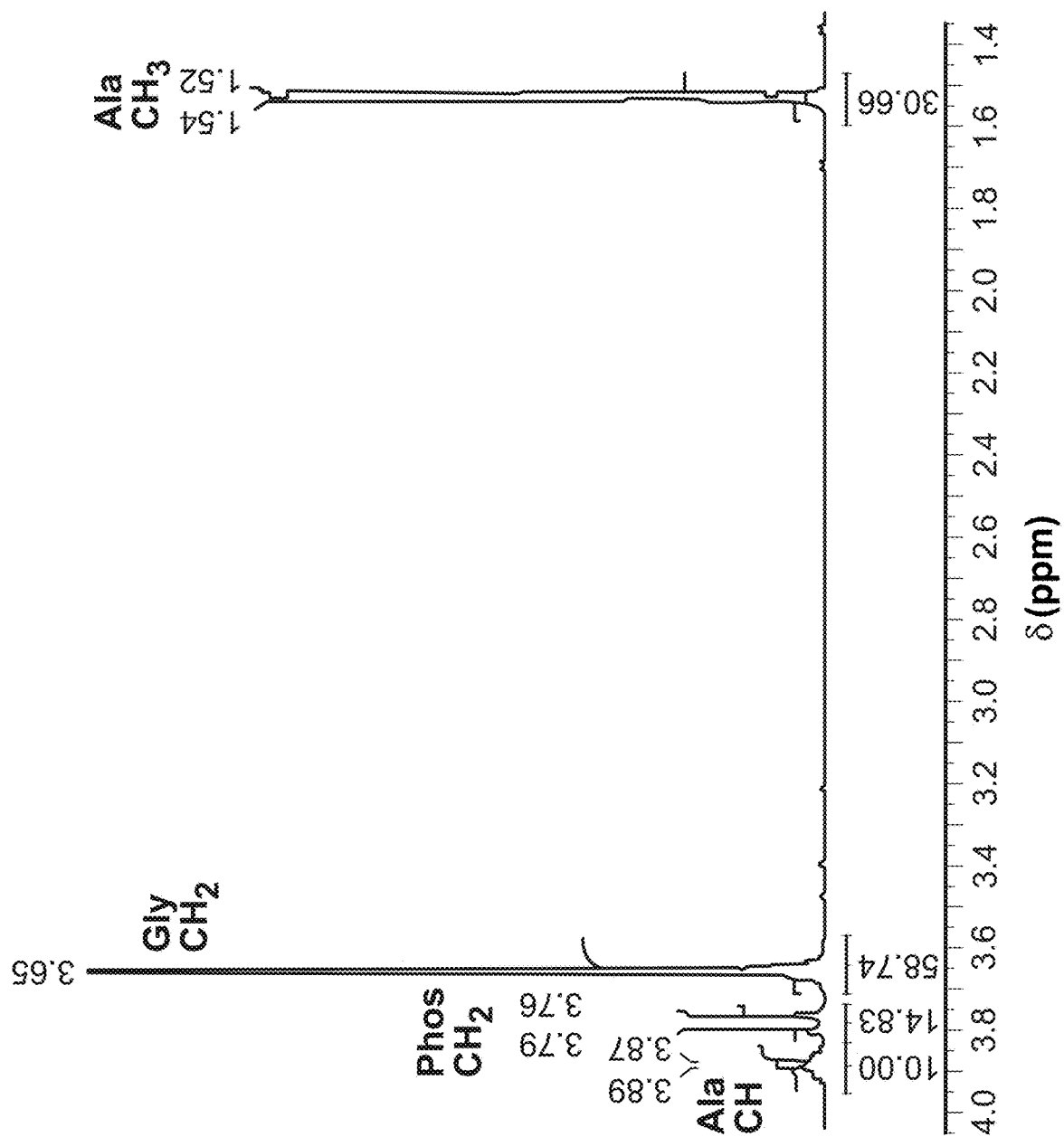
FIG. 19. $^1H$ (a), $^{13}C$ (b) and $^{31}P$ NMR (c) spectra of a set 1 sample (Table 4) obtained after reaction for 24 h at 95° C. and using a 5 mM $ZrOCl_2$ solution for preparing the layered system.
Figure 19B:
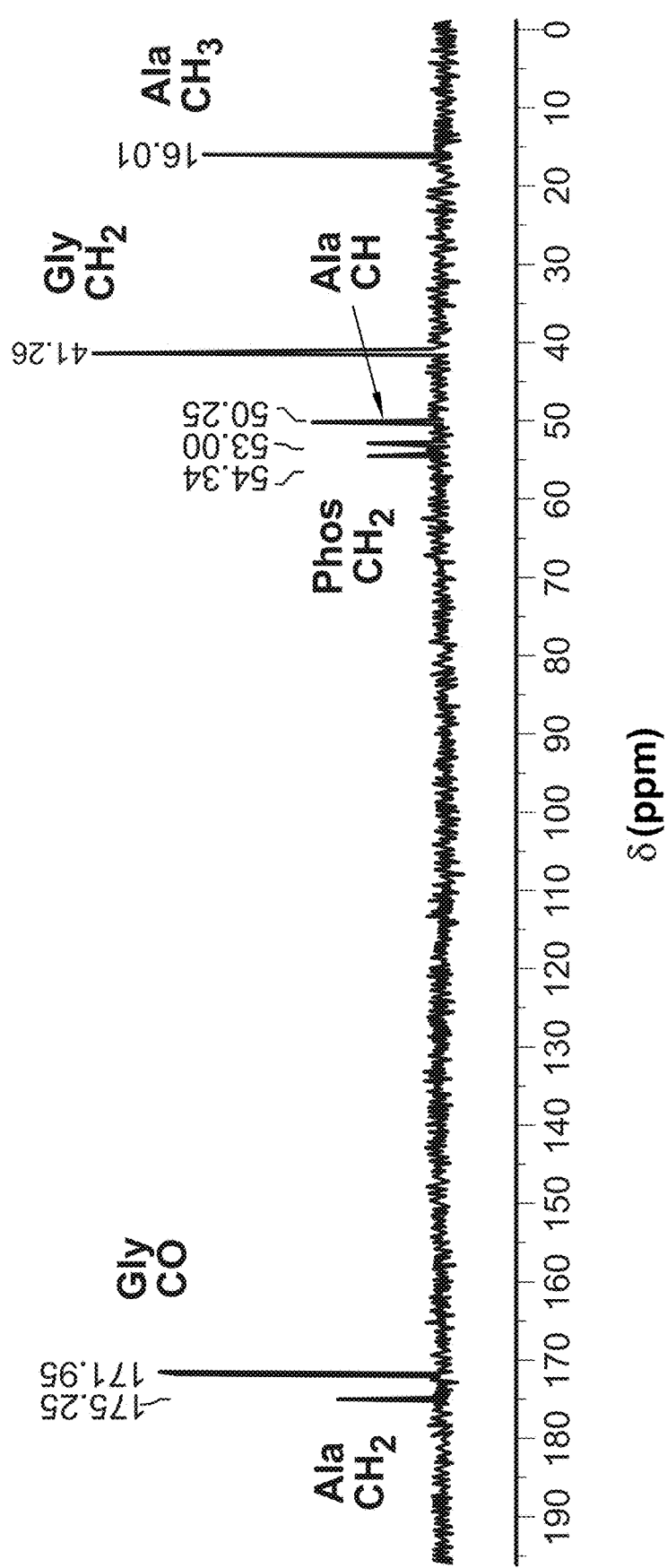
Figure 19C:
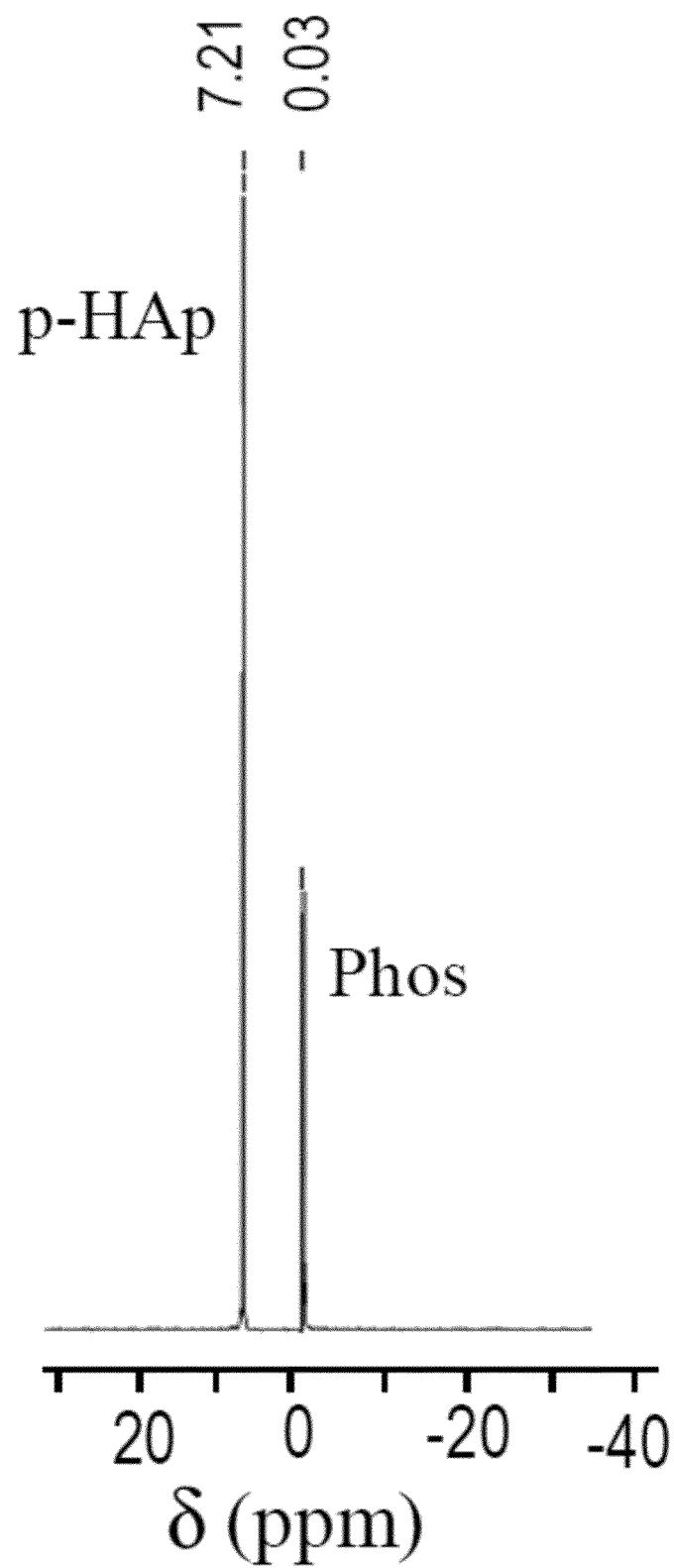

$^1$H NMR spectra (FIG. 19a) showed only the presence after reaction of the phosphonate methylene group (i.e. doublet at 3.79-3.76 ppm) and signals corresponding to methylene protons of glycine (singlet at 3.65 ppm) and both methine (quadruplet at 3.91-3.85 ppm) and methane (doublet at 1.54-1.52 ppm) groups of alanine. The same compounds were also evidenced in the $^{13}$C NMR spectrum (FIG. 19b) where only peaks assigned to the phosphonate (54.34 and 53.00 ppm), glycine (171.95 and 41.26 ppm) and alanine (175.25, 50.25 and 16.01 ppm) units could be detected. It is noteworthy that no by-products were observed and consequently a very clean process for production of glycine and alanine was developed.

$^1$H NMR spectra were analyzed for samples recovered after different reaction times (i.e. from 2 to 96 h), being possible to detect the ratios between glycine and phosphonate units (Gly/Phos), alanine and phosphonate units (Ala/Phos) and obviously between glycine and alanine unis (Gly/Ala). Specifically, the areas of signals corresponding to $CH_2$ protons at 3.65 and 3.79-3.76 ppm and the $CH_3$ protons at 1.54-1.52 ppm were considered:

$$\text{Gly/Phos} = (3 \times A_{3.65})/A_{3.79-3.76} \quad (1)$$

$$\text{Ala/Phos} = (2 \times A_{1.54-1.52})/A_{3.79-3.76} \quad (2)$$

$$\text{Gly/Ala} = (1.5 \times A_{3.65})/A_{1.54-1.52} \quad (3)$$

from 5.4 to 2.2, being nevertheless observed a continuous increase of the Gly/Phos ratio with the reaction time (i.e. from 0.8 to 4.5).

Figure 20:
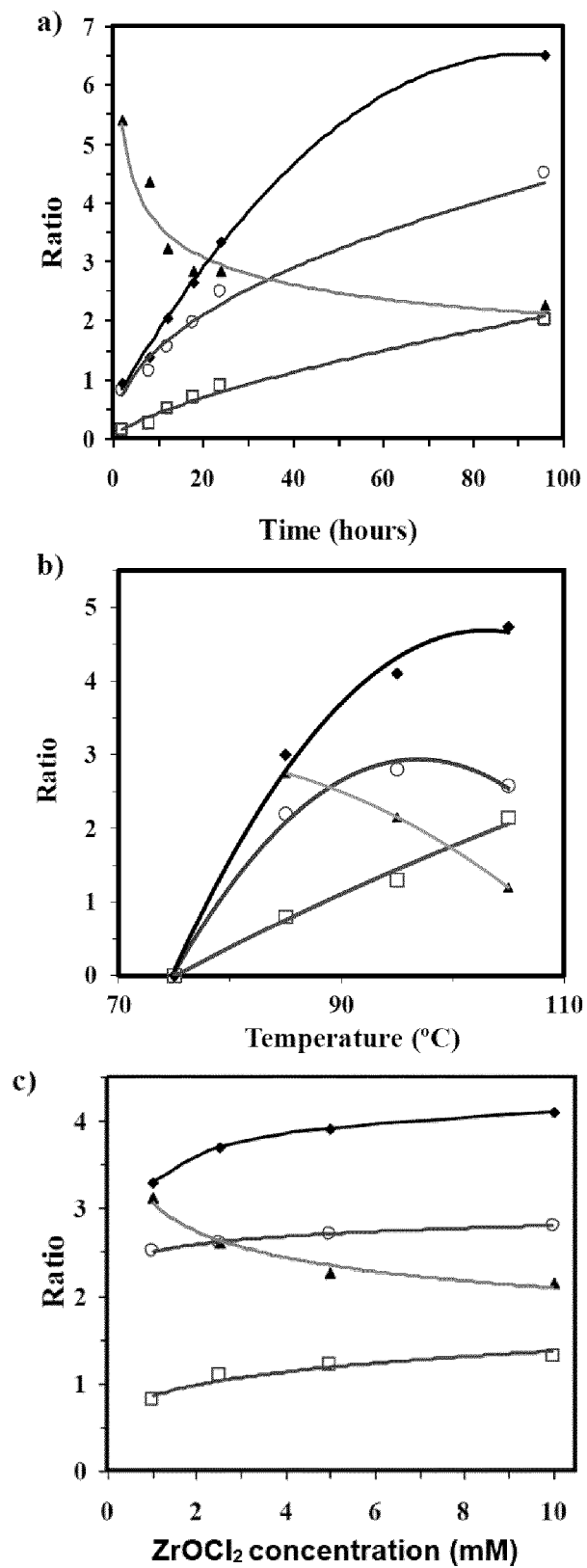
FIG. 20. Variation of Gly/Phos (○), Ala/Phos (□) (Gly+Ala)/Phos (◆) and Gly/Ala (▲) ratios versus time for reactions performed at 95° C. using set 1 samples (Table 4) prepared from a 5 mM $ZrOCl_2$ solution (a), versus temperature for reactions performed during 24 h using the same sample (b) and versus concentration of zirconium oxychloride solutions (c) for reactions performed at 95° C., 24 h and using set 1 samples.

FIG. 20b allows estimating the effect of reaction temperature and specifically that a minimum value (i.e. 75° C.) is required to get a detectable amount of amino acids after 24 h of reaction. The Ala/Phos ratio continuously increased with reaction temperature while the Gly/Phos ratio started to decrease at the maximum assayed temperature (105° C.) as a result of conversion of glycine into alanine. Nevertheless, the ratio between the total amino acid content and the phosphonate content still increased at this temperature.

FIG. 20c shows as the content of the Zirconium oxychloride has a practically negligible influence on the Gly/Phos and Ala/Phos ratios, as presumable for a catalyst. Nevertheless, samples prepared from solutions with a very low concentration of $ZrOCl_2$ (1 mM) led to significantly lower ratios as a consequence of the defective trilayered system. Logically, alanine was in this case the amino acid more disfavoured (i.e. the Gly/Ala ratio was maximum).

Experiments have also been assayed without exposure to the UV radiation (set 2), being in this case unsuccessful the formation of amino acids. Thus, the sustained exposure to UV logically appears as a fundamental issue to get radicals (e.g. $CH_3$-) for further reaction towards formation of alanine and even glycine.

Figure 21:
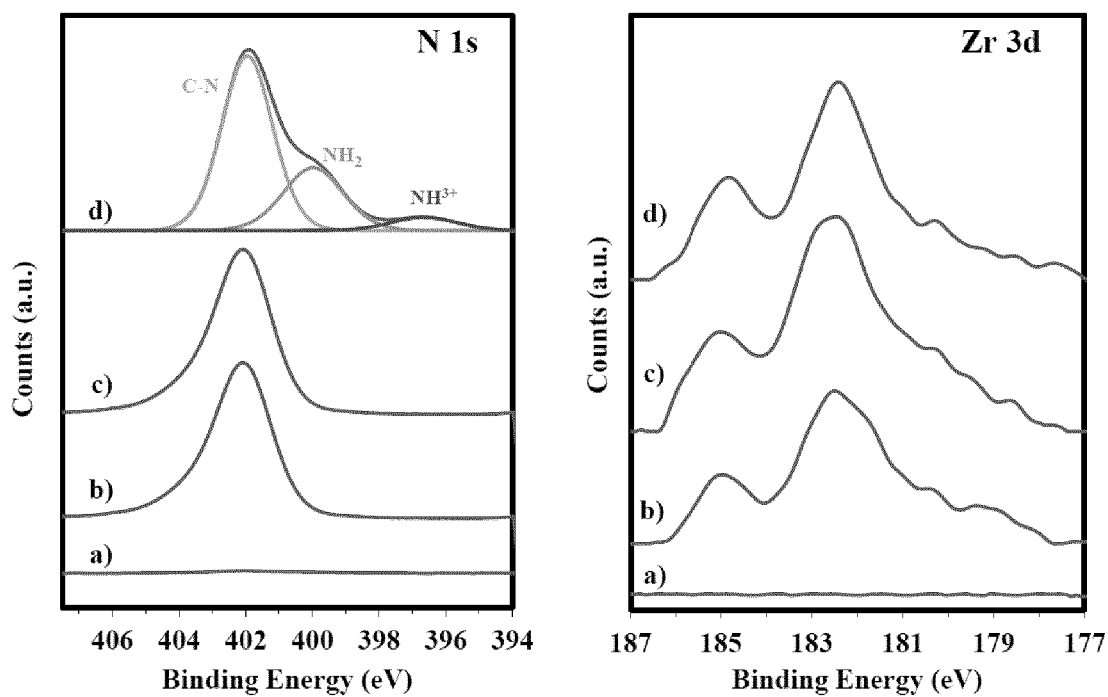
FIG. 21. High resolution XPS spectra for (a) p-cHAP, (b) p-cHAP+Phos-Zr-Phos, c) p-cHAP+Phos-Zr-Phos after negative reaction (e.g. without exposure to UV radiation) and d) p-CHAP+Phos-Zr-Phos after positive reaction (24 h at 95° C.): Nis, and Zr3d regions.

XPS analysis was fundamental to corroborate that amino acids were derived from the molecular nitrogen and not from a hypothetical decomposition of the phosphonate compound. Note that this point cannot be inferred from the NMR spectra since the increase of Gly/Phos could also be related to a decomposition process. FIG. 21a shows the XPS spectra in the $N_1s$ region for different representative samples and specifically as a peak around 399 eV appears when phosphonate is incorporated onto the surface of p-cHAp. This peak is associated to the nitrogen in the C—N bond and is observed with practically the same intensity when both negative and positive reactions took place. Only in the last case additional peaks corresponding to the deprotonated ($NH_2$) and protonated ($NH_3^+$) amino groups were observed at 400.3 eV and 403.8.4 eV, respectively.[32] The amount of nitrogen increased from 0% to 2.75-2.97% when the Phos-Zr-Phos trilayer was deposited onto the p-cHAP substrate and to 6.2% after positive reaction (i.e. set 1 for 24 h at 95° C.). XPS spectra allowed determining the decrease of Ca/P ratio from a typical value of 1.64 for HAp to 1.26-1.29 when the trilayer was deposited onto the HAp surface. XPS spectra showed also Zr signals (FIG. 21b) which appeared as a resolved spin doublet at binding energies of 182.6 (3d5/2) and 185 eV (3d3/2). The measured Zr content was in the 1.26-1.29% range for all samples having the Phos-Zr-Phos trilayer prepared from a 5 mM Zirconium oxychloride solution, being this percentage independently of the progress of the reaction.

Figure 22:
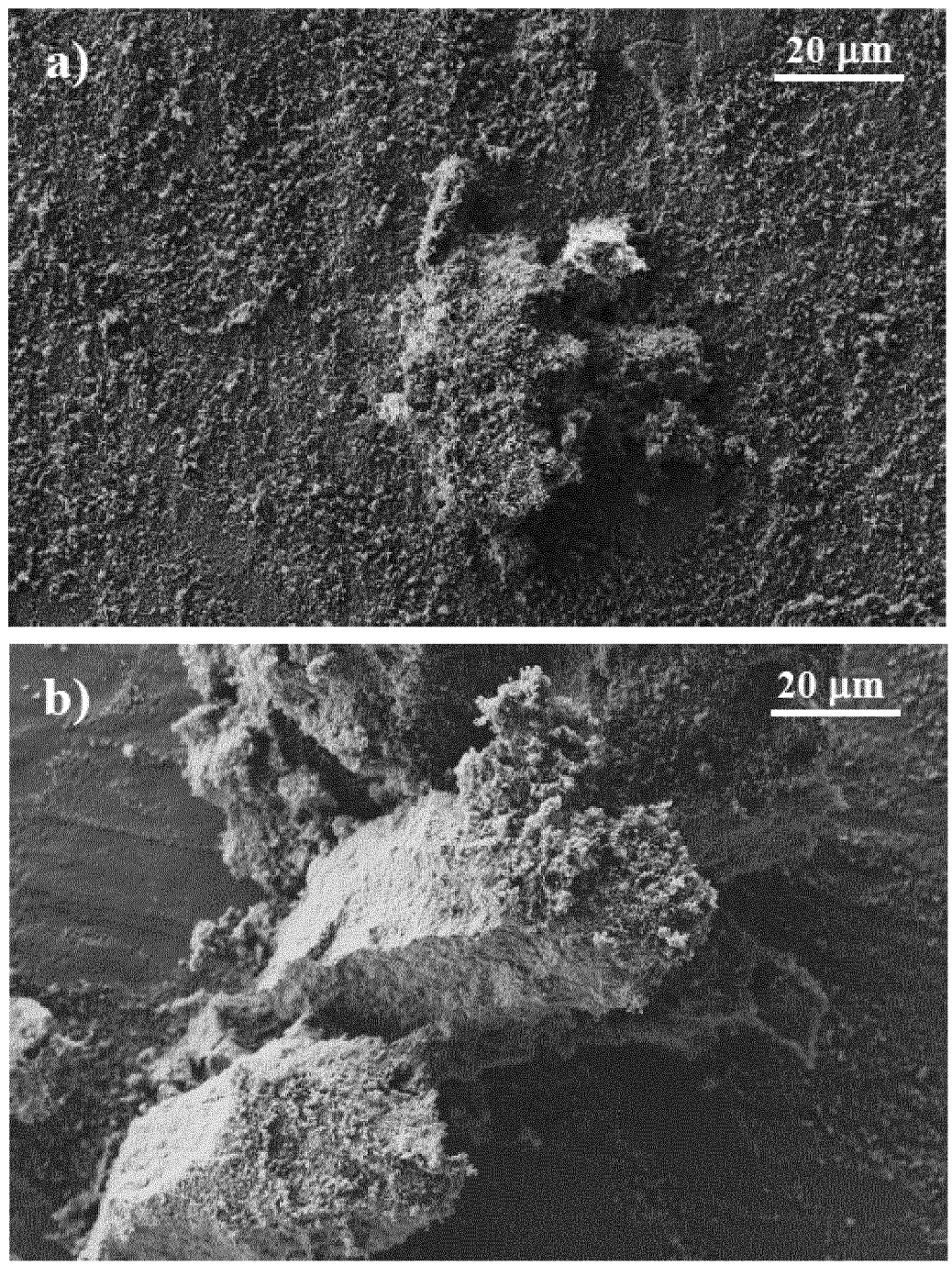
FIG. 22. SEM micrograps of a set 1 sample before (a) and after (b) reaction for 24 h at 95° C. and using a 5 mM $ZrOCl_2$ solution for preparing the layered system.

Deposition of the trilayered system on HAp gave rise to a rough and relative irregular disk surface as shown in the SEM micrograph corresponding to a polarized sample (FIG. 22a). This surface slightly changed after reaction since a sporadic formation of regular crystals was detected. FIG. 22b shows the growth of micrometric prismatic structures where the hexagonal basal plane tended to be parallel to the disk surface. In fact, it has been reported the capacity of organophosphonate films for inducing crystallization and grown of oriented molecular sieves. In this way, stable, vertically oriented and one dimensional aluminium phosphate crystals were able to grow over the hybrid layers. Cannel systems that could be applied as new catalytic membranes with true molecular selectivity and even for controlling the access of determined size to a sensor surface were formed. In any case, the present results demonstrate that amino acid crystals can also grow onto the surface of the trilayered catalyst but it should also be taken into account that the nynhydrin test revealed the presence of absorbed amino acids inside the disk sample.

Figure 23:
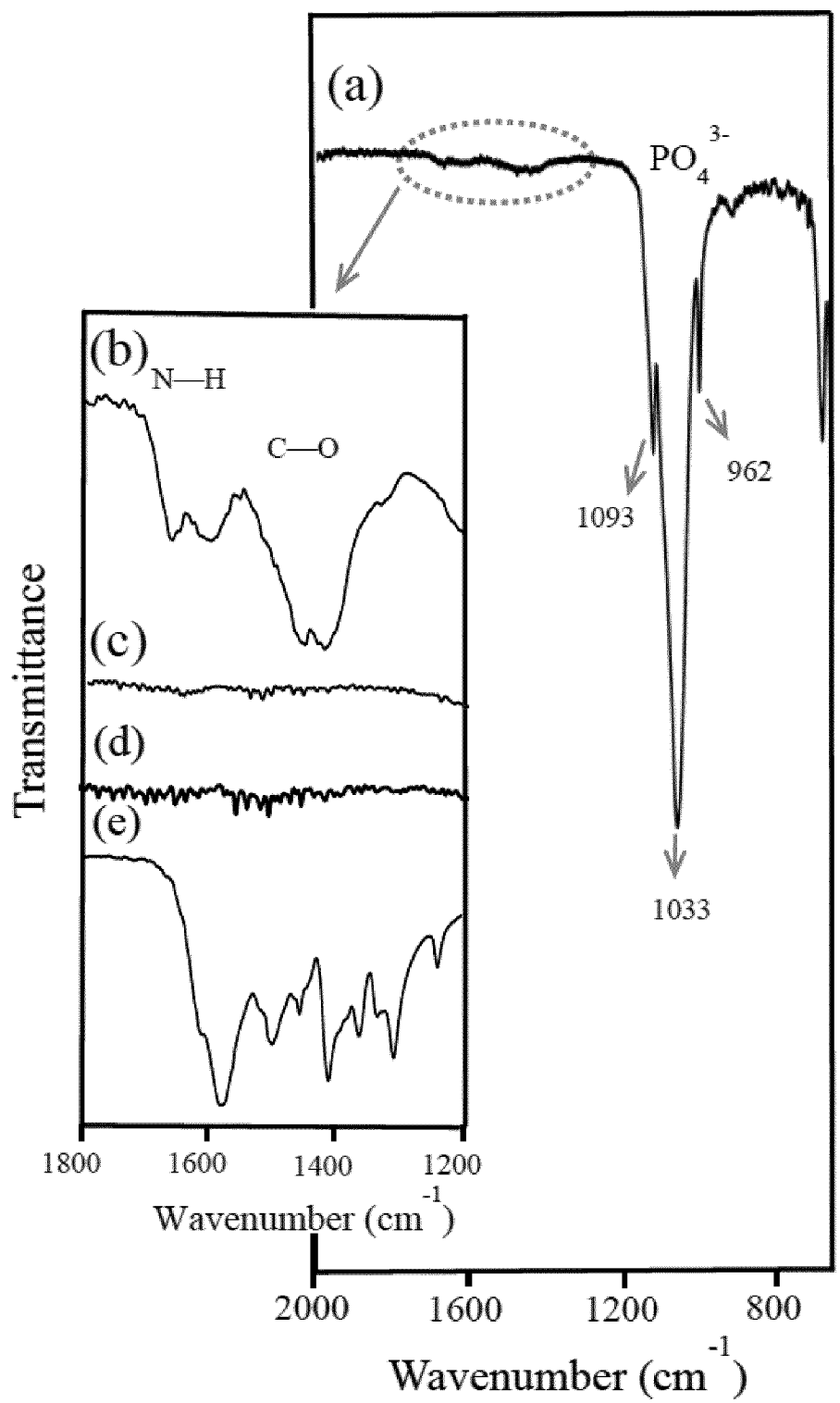
FIG. 23. a) FTIR spectra of a set 1 sample after reaction for 24 h at 95° C. and using a 5 mM $ZrOCl_2$ solution for preparing the layered system. Insets compare the 1700-1500 $cm^{-1}$ region for the above sample after (b) and before reaction (d), a set 2 sample after reaction (c) and a mixture of glycine and alanine (2:1 weight ratio) (e).

Significant differences between set 1 samples before and after reaction can be observed in the FTIR spectra despite the low sensitivity of the technique. Thus, broad and low-intensity bands in the 1600-1400 $cm^{-1}$ region could only be observed in the second case (FIG. 23). It is worth noting that this region is completely flat in the spectra of samples before reaction and also for samples coming from a negative ninhydrin test (e.g. set 2 samples). On the contrary, amino acids such as glycine and alanine have the most intense absorptions in this region (see inset of FIG. 23). Logically, FTIR spectra showed the characteristic peaks of HAp and specifically the three intense bands at 1093, 1033 and 962 $cm^{-1}$ associated to the characteristic vibrational modes of $PO_4^{3-}$ were always observed.

Figure 24:
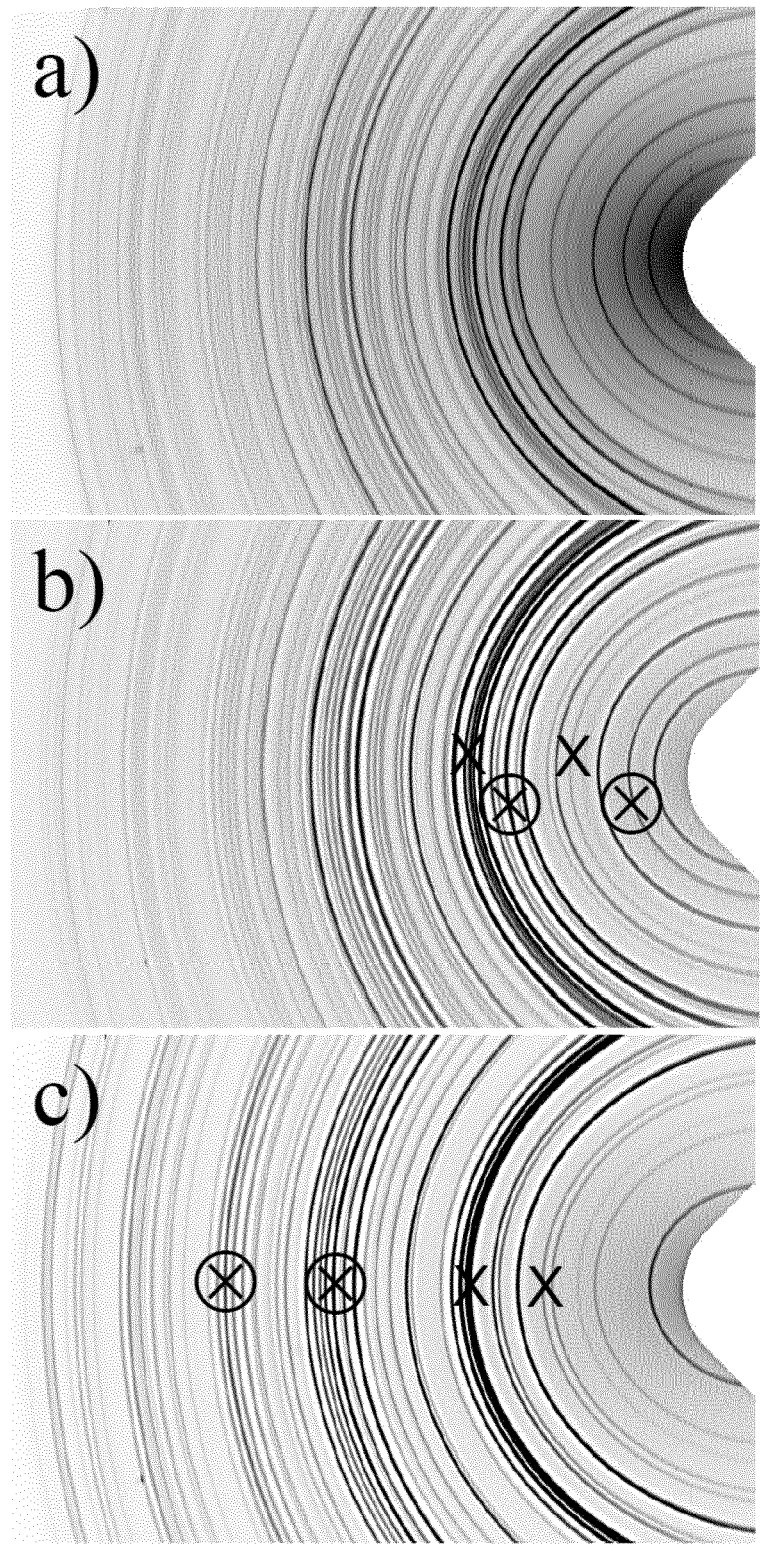
FIG. 24. X-ray diffraction patterns corresponding to polarized c-HAp (a) and the set 1 sample before (b) and after (c) reaction for 24 h at 95° C. and using a 5 mM $ZrOCl_2$ solution for preparing the layered system. Gray crosses point out characteristic X-ray diffraction reflections of the catalyst that disappear after reaction whereas red crosses point out new reflections that can be observed after reaction. Circled symbols indicate the reflections that changed more drastically during reaction.

Deposition of the trilayered systems over the polarized c-HAp did not cause a significant change on the X-ray diffraction pattern (FIGS. 24a and 24b) whereas remarkable changes can be observed after chemical reaction (FIGS. 24b and 24c).

Influence of Changes on the Catalyst System and the Polarized Support on the Synthesis of Amino Acids Amino acids were also detected when p-aHAp was employed instead of p-cHAp and the experimental conditions of set 1 were maintained. Nevertheless, we preferred to insist on p-cHAp since the amorphous sample suffered a partial decomposition during the sintering process, which led to the formation of β-tricalcium phosphate (β-TOP: β-$Ca_3(PO_4)_2$) as the predominant phase.

Different assays have been performed in order to evaluate the importance of the type of substrate of the catalytic system. Amino acids were only detected when polarized HAp was employed (e.g. sets 1 and 3 in Table 4), being highly significant the negative results obtained when sintered HAp (set 4) was used as a substrate and also when other systems such as silicates (e.g. Nanofil 757, set 5) and aluminosilicates (e.g. layered mica, set 5) were tested even after being polarized under similar conditions to those applied for p-cHAp.

The suitability of the HAp contribution is interesting since it plays a fundamental role in living systems and specifically constitutes their most abundant inorganic component. The relationship between HAp and biological molecules (e.g. proteins like collagen and even DNA constituted by a phosphate skeleton) has nowadays enhanced an intensive research on its use for different biomedical applications (e.g. drug and gene delivery, bone repair and tissue engineering among others).

In this sense, it is also remarkable that the metal/phosphonate layered system is also able to molecular recognition and consequently a selective binding of an enantiomeric compound from a racemic solution can be achieved. Furthermore, the high insolubility and stability towards thermal treatments and chemical reactants of zirconium phosphonates have opened other potential applications such as viral vectors in gene delivery. The positive charge of amino-functionalized phosphonates (e. g. the aminoethoxy derivative) allows the direct intercalation of negatively charged DNA molecules. Moreover, binding is pH sensitive being found that the conformation of DNA could be almost retained during intercalation and release processes.

For the sake of completeness we have also assayed the effectiveness of the two possible bilayered (deposition of a first layer of Phos or Zr and subsequent deposition of the second complementary layer, sets 7 and 8, respectively) and monolayer (sets 9 and 10) systems. In all cases, negative results were attained demonstrating that a stable Phos-Zr complex with a nucleation activity was only attained using the trilayered architecture. Probably dissolution of components in the water reaction medium should also be taken into account when bilayered and monolayer arrangements are considered.

Table 4 reports also the results attained when only phosphonate (set 11) and even a mixture of phosphonate and Zirconium oxychloride (set 12) were introduced into the reactor instead of the coated polarized support. These assays are also relevant since help discarding a process based on the decomposition of AMTP. Note that in this case the amount of AMTP submitted to UV irradiation and able to react with the selected reducing atmosphere was much higher than required in the trilayered system.

Comparative Figures with Respect of Prior Art

Figure 25:
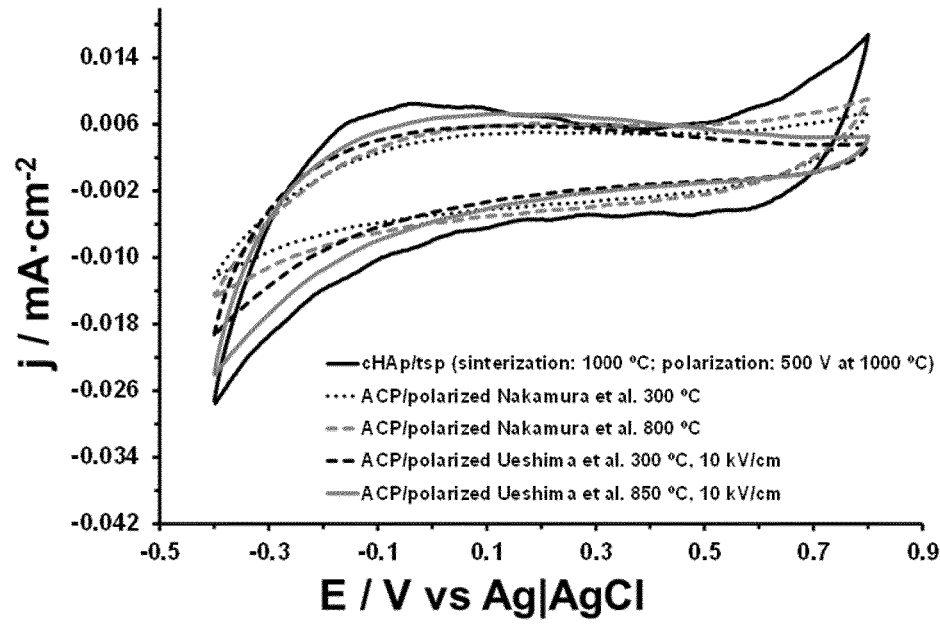
FIG. 25. Voltammogram after 20 consecutive oxidation and reduction cycles For cHAp/tsp (prepared according to our conditions) and the polarized mineral prepared according to the conditions of Nakamura et al. and Ueshima et al. with samples as prepared. Conditions of Nakamura et al. (J. Biomed. Mater. Res. 2006, 79A, 627-634):
i) Synthesis by precipitation at room temperature;
ii) Drying at 850° C. for 2 h
iii) Calcination at 1250° C. in saturated water atmosphere for 2 h
iv) Polarization at 1 kV/cm for 1 h at 300 or 800° C.
Conditions of Ueshima et al. (Solid State Ionics 2002, 151, 29-34):
i) Synthesis by precipitation at room temperature;
ii) Drying at 850° C. for 2 h
iii) Calcination at 1250° C. in saturated water atmosphere for 2 h
iv) Polarization at 10 kV/cm for 1 h at 300 or 850° C.

The voltammograms recorded after 20 consecutive oxidation-reduction cycles are displayed in FIG. 25. The similarity between the areas of the anodic and cathodic scans, which correspond to the associated to the oxidation and reduction processes, respectively, have been used to determine the electrochemical activity. As it can be seen, the area of the cHAp/tsp voltammogram is at least 20% higher than the areas of those recorded for the different ACP/polarized samples, indicating that the former material presents higher ability to store charge reversibly than the latter samples. Moreover, a significant difference is also detected in the anodic and cathodic current densities at the final and reversal potentials, respectively. The current densities are significantly higher, in absolute values, for cHAp/tsp than for the other samples, reflecting a higher movement of charge during the oxidation and reduction processes. This feature is particularly noticeable for the anodic current density. Thus, anodic current density determined for cHAp/tsp is 16.8 µA/cm$^2$ while that of the other samples ranges between 4 and 9 µA/cm$^2$.

Figure 26:
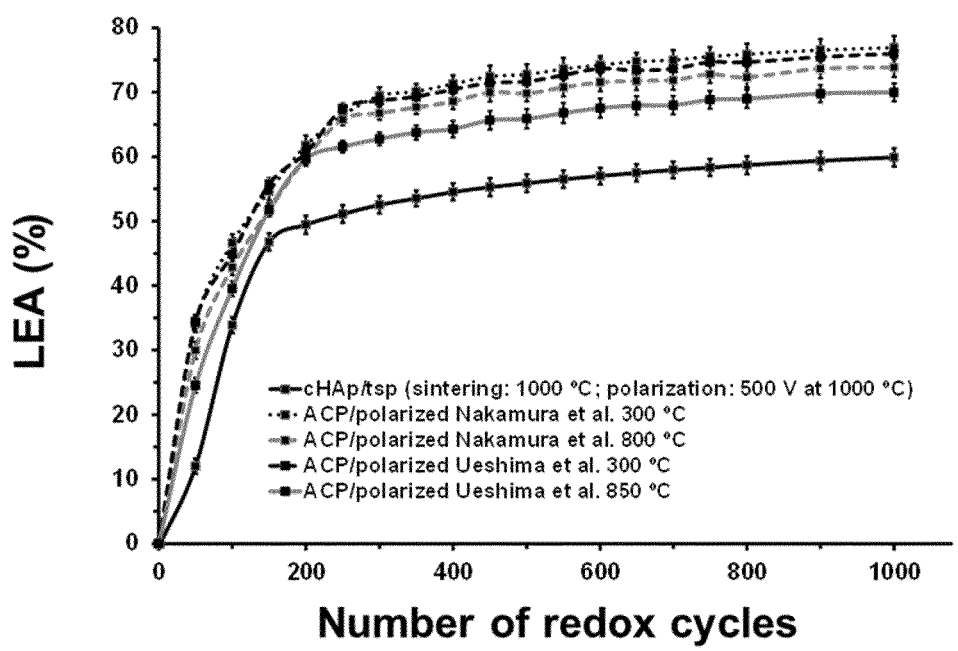
FIG. 26. Loss of electrochemical activity against the number of oxidation-reduction cycles for cHAp/tsp (prepared according our conditions) and the polarized mineral prepared according to the conditions of Nakamura et al. and Ueshima et al. with samples as prepared.
Conditions of Nakamura et al. (J. Biomed. Mater. Res. 2006, 79A, 627-634):
i) Synthesis by precipitation at room temperature;
ii) Drying at 850° C. for 2 h
iii) Calcination at 1250° C. in saturated water atmosphere for 2 h
iv) Polarization at 1 kV/cm for 1 h at 300 or 800° C.
Conditions of Ueshima et al. (Solid State Ionics 2002, 151, 29-34):
i) Synthesis by precipitation at room temperature;
ii) Drying at 850° C. for 2 h
iii) Calcination at 1250° C. in saturated water atmosphere for 2 h
iv) Polarization at 10 kV/cm for 1 h at 300 or 850° C.

FIG. 26 displays the variation of electrochemical activity with the number of redox cycles (electrostability) with respect to the first cycle. Results prove that the excellent results of cHAp/tsp in comparison with all the ACP/polarized samples. After 1000 consecutive oxidation-reduction cycles, the loss of electrochemical activity (LEA) is at least 10% lower for cHAp/tsp than for the other samples. Moreover, the cHAp/tsp preserves the highest electrostability in all cases, independently of the number of cycles, evidencing that this property is inherent to its structure.

Results represented in FIGS. 25 and 26 are fully consistent with a highly organized and regular structure of cHAp/tsp, which is in agreement with NMR observations. Thus, the latter technique allowed us not only to identify the highly crystalline organization of cHAp/tsp but also to evidence the lack of protonated surfaces phosphate groups arising from the disordered near surface layer, as is typically observed in the rest of samples, as for example prepared and sintered HAp).

Finally, the comparative table of FIG. 27 shows that the electrical resistivity of cHAp/tsp is one order of magnitude smaller than those of ACP/polarized samples, which in turn are practically identical to that of cHAp/s (0.67×10$^7$ Ω·cm$^2$, as mentioned above). This feature points out the importance of the temperature in the electrical polarization step. Accordingly, temperatures higher than 900° C. are necessary to eliminate completely the protons near surface layers, facilitating the creation of both an ordered organization and charge defects able to move with the electric field. In contrast, the similarity between cHAp/s and ACP/polarized in terms of electrical resistivity reflects that these feature are not achieved when polarization is carried out at temperatures lower than 900° C.

Figure 28:
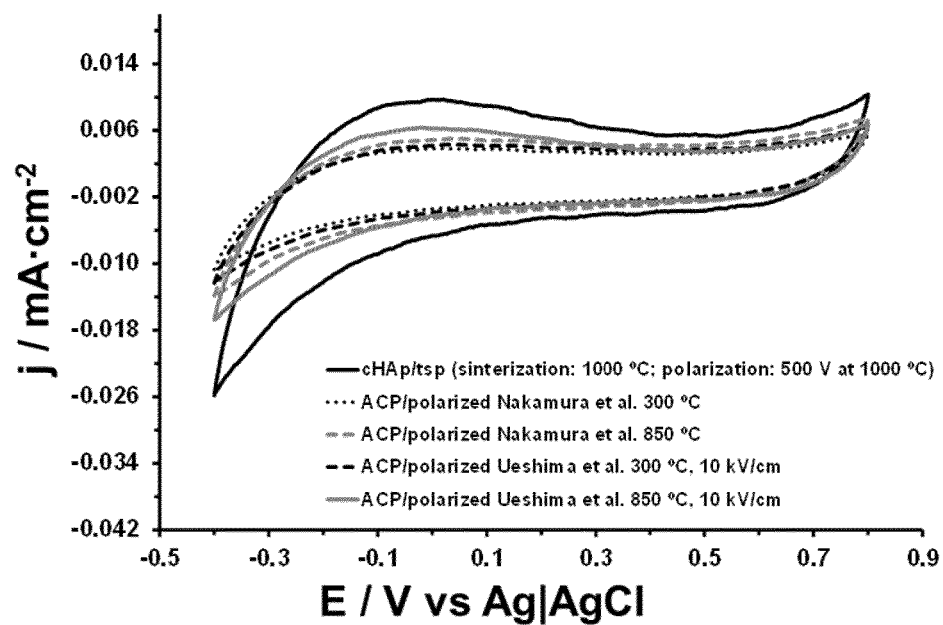
FIG. 28. Re-evaluation of the samples as in FIG. 25 after 3 months.

The samples tested in FIGS. 25 and 27 were re-evaluated after three months as shown in FIGS. 28 and 29, respectively.

In particular, the electrochemical behavior of all samples was re-evaluated (storage was done at ambient conditions, without any special care) by cyclic voltammetry (see FIG. 28). Results indicate that cHAp/tsp (according to the present invention) remains practically unaltered, as is evidenced by comparison with the voltammogram displayed in FIG. 25. In contrast, all other ACP/polarized samples (according to Nakamura et al. and Ueshima et al.) converge to the same behavior, which is similar to that displayed by cHAp/s. Thus, the electroactivity of cHAp/tsp is significantly higher than that of ACP/polarized samples. This feature supports the importance of the polarization temperature as well as the permanent polarized character of cHAp/tsp. In opposition, the changes observed in ACP/polarized samples after three months indicate that the polarization imparted at temperatures <850° C. is not permanent but only temporal.

As shown in FIG. 29, the specific capacitance (capacitance per unit of mass, abbreviated SC) of cHAp/tsp decreases 8% after three months (storage was done at ambient conditions, without any special care). In contrast ACP/polarized samples prepared according to Yamashita and co-workers (Nakamura et al. and Ueshima et al.) present a drastic reduction of the SC, which ranges from 50% to 64%. As it can be seen in the previous Table (FIG. 27), the SC of cHAp/tsp is higher than those of ACP/polarized by one order of magnitude. A similar effect is observed in the electrical resistance. The value of cHAp/tsp increases 9% after 3 months, while the resistances of ACP/polarized prepared using the procedures of Yamashita and co-workers increase around 60-70%.

In view of the above results, it is concluded that the hydroxyapatite, as obtained by the present invention, is different from those disclosed in the prior art. It is apparent from the experimental data that the hydroxyapatite of the present invention shows a significant different behavior and it is effectively a permanently polarized hydroxyapatite, whereas those disclosed in the prior art are only temporal polarized hydroxyapatites.

REFERENCES

1. S. V. Dorozhkin and M. Epple, Angew. Chem., Int. Ed., 2002, 41, 3130.
2. L. C. Palmer, C. J. Newcomb, S. R. Kaltz, E. D. Spoerke and S. I. Stupp, Chem. Rev., 2008, 108, 4754.
3. M. Y. Ma, Y. J. Zhu, L. Li and S. W. Cao, J. Mater. Chem., 2008, 18, 2722.
4. K. W. Wang, L. Z. Zhou, Y. Sun, G. J. Wu, H. C. Gu, Y. R. Duan, F. Chen and Y. J. Zhu, J. Mater. Chem., 2010, 20, 1161.
5. Q. L. Tang, Y. J. Zhu, J. Wu, F. Chen and S. W. Cao, Nanomed.: Nanotechnol., Biol. Med., 2011, 7, 428.
6. H.-W. Kim, J. C. Knowles, and H.-E. Kim, Biomaterials 25, 1279 (2004).
7. W. Suchanek and M. Yoshimura, J. Mater. Res., 1998, 13, 94.
8. H. Zhou and J. Lee, Acta Biomater., 2011, 7, 2769.
9. J. C. Elliott, P. E. Mackie, and R. A. Young, Science 180, 1055 (1973).
10. G. Ma and X. Y. Liu, Cryst. Growth Des. 9, 2991 (2009).
11. N. Hitmi, C. LaCabanne, and R. A. Young, J. Phys. Chem. Solids 49, 541 (1988).
12. T. Ikoma, A. Yamazaki, S. Nakamura, and M. Akao, J. Mater. Sci. Lett. 18, 1225 (1999).
13. I. M. Kalogeras, A. Vassilikou-Dova, and A. Katerinopoulou, J. Appl. Phys. 92, 406 (2002).
14. N. Horiuchi, M. Nakamura, A. Nagai, K. Katayama and K. Yamashita, *J. Appl. Phys.*, 2012, 112, 074901.
15. N. Horiuchi, S. Nakaguki, N. Wada, M. Nakamura, A. Nagai, K. Katayama and K. Yamashita, *J. Appl. Phys.*, 2014, 116, 014902.
16. Nakamura, M.; Hori, N.; Namba, S.; Toyama, T.; Nishimiya, N.; Yamashita, K. *Biomed. Mater.* 2015, 10, 011001.
17. M. Nakamura, A. Nagai, T. Hentunen, J. Salonen, Y. Sekilima, T. Okura, K. Hashimoto, Y. Toda, H. Monma, K. Yamashita, *ACS Appl. Mater. Interfaces*, 2009, 1, 2182.
18. M. Rivas, J. Casanovas, L. J. del Valle, O. Bertran, G. Revilla-López, P. Turón, J. Puiggalí, C. Alemán *Dalton Trans.*, 2015, 44, 9980-9991.

19. K. D. Kumble and A. Kornberg, *J. Biol. Chem.*, 1996, 270, 5818-5822.
20. K. Doi, T. Kubi, R. Takeshita, S. Kajihara, S. Kato, Y. Kawazoe, T. Shiba and Y. Akagawa, *Dent. Mat. J.,* 2014, 33, 179-186.
21. P. A. Comeau, H. Frei, C. Yang, G. Fernlund and F. M. Rossi, *J. Biomat. Appl.,* 2012, 27, 267-275.
22. K. Siggers, H. Frei, G. Fernlund, and F. Rossi, *J. Biomed. Mat. Res. Part A,* 2010, 94, 877-885.
23. K. Morita, K. Doi, T. Kubo, R. Takeshita, S. Kato and Y. Akagawa, *Acta Biomat.,* 2010, 6, 2808-2815.
24. Q. Yuan, T. Kubo, K. Doi, K. Morita, R. Takeshita, S. Kato, T. Shiba and Y. Akagawa, *Acta Biomat.,* 2009, 5, 1716-1724.
25. T. Shiba, D. Nishimura, Y. Kawazoe, Y. Onodera, K. Tsutsumi, R. Nakamura and M. Ohshiro, *J. Biol. Chem.,* 2003, 278, 26788-26792.
26. Y. Kawazoe, T. Shiba, R. Nakamura, A. Mizuno, K. Tsutsumi, T. Uematsu, M. Yamaoka, M. Shindoh and T. Kohgo, *J. Dent. Res.,* 2004, 83, 613-618.
27. Y. Hacchou, T. Uematsu, O. Ueda, Y. Usui, S. Uematsu, M. Takahashi, Y. Kawazoe, T. Shiba, S. Kurihara, M. Yamaoka and K. Furusawa, *J. Dent. Res.,* 2007, 86, 893-897.
28. H. Fleisch and S. Bisaz, Nature, 1962, 195, 911-911.
29. H. Fleish, R. Russel and F. Straumann, Nature, 1966, 212, 901-903.
30. S. Omelon, J. Georgiou, Z. J. Henneman, L. M. Wise, B. Sukhu, T. Hunt, C. Wynnyckyj, D. Holmyard, R. Bielecki, and M. D. Grynpas, *PLos One,* 2009, 4, e5634.
31. S. S. Kamat and F. M. Raushel, *Curr. Opin. Chem. Bio.,* 2013, 17, 589-596.
32. F. H. Ebetino and R. G. G. Russell, *J. Bone Miner Res.,* 2005, 20, 259.
33. R. G. G. Russell and F. H. Ebetino, *Osteoporos. Int.,* 2008, 19, 733-759.
34. N. Gronich and G. Rennet, *Nat. Rev. Clin. Oncol.,* 2013, 10, 625-642.
35. L. J. del Valle, O. Bertran, G. Chaves, G. Revilla-López, M. Rivas, M. T. Casas, J. Casanovas, P. Turon, J. Puiggalí, C. Alemán *J. Mater. Chem. B,* 2014, 2, 6953-6966.
36. H. Klug and L. Alexander in *X-Ray Diffraction Procedure for Polycrystallite and Amorphous Materials,* $2^{nd}$. Edition, John Wiley and Sons, New York, 1974).
37. E. Landi, A. Tampieri, G. Celotti and S. Sprio, *J. Eur. Ceram. Soc.,* 2000, 20, 2377-2387.
38. F. Estrany, D. Aradilla, R. Oliver and C. Aleman, Eur. Polym. J., 2007, 43, 1876.
39. F. Müller, C. A. Ferreira, D. S. Azambuja, C. Aleman, E. Armelin, Measuring the Proton Conductivity of Ion-Exchange Membranes Using Electrochemical Impedance Spectroscopy and Through-Plane Cell, *J. Phys. Chem. B* 2014, 118, 1102-1112.
40. S. Raynaud, E. Champion, Bernache-Assollant, P. Thomas. *Calcium phosphate apatites with variable Ca/P atomic ratio I: synthesis, characterization and thermal stability of powders.* Biomaterials, 23, 1065-1072 (2002).
41. H. Fujimori, H. Toya, K. loku, S. Goto, and M. Yoshimura, Chem. Phys. Lett. 325, 383 (2000).
42. J. C. Elliott, P. E. Mackie, and R. A. Young, Science 180, 1055 (1973).
43. N. Hitmi, C. LaCabanne, and R. A. Young, J. Phys. Chem. Solids 49, 541 (1988).
44. G. Ma and X. Y. Liu, Cryst. Growth Des. 9, 2991 (2009).
45. Handbook of X-ray Photoelectron Spectroscopy (Eds.: J. F. Moulder, J. Chastain), Physical Electronics Division, PerkinElmer Corporation, 1995.
46. M. C. Chang, J. Tanaka, Biomaterials 2002, 23, 3879-3885.
47. Bertran, O.; del Valle, L. J.; Revilla-López, G.; Rivas, M.; Chaves, G.; Casas, M. T.; Casanovas, J.; Turon, P.; Puiggalí, J. *Chem. Eur. J.* 2015, 21,2537-2546.
48. I. Ming-Hung, W.-J. Shih, M.-H. Hon, M.-C. Wang, *Int. J. Mol. Sci.* 2012, 13, 13569-13586.
49. J. P. Gittings, C. R. Bowen, A. C. E. Dent, I. G. Turner, F. R. Baxter, J. B. Chaudhuri, Electrical characterization of hydroxyapatite-based bioceramics. Acta Biomaterialia 5 (2009) 743-754.
50. M. J. Lukic, C. Jovalekic, S. Markovic, D. Uskolovic. Enhanced high-temperature electrical response of hydroxyapatite upon grain size refinement. Materials Research Bulletin 61 534-538 (2014).
51. Y. Liu, Z. Shen. Dehydroxylation of hydroxyapatite in dense bulk ceramics sintered by spark plasma sintering. J. Eur. Ceram. Soc. 32 (11), 2691-2696 (2012).
52. S. Tarafder, S. Banerjee, A. Bandyopadhyay, S. Bose. Langmuir 2010, 26, 16625-16629.
53. K. J. Gaskell, A. L. Asunkis, P. M. A. Sherwood. *Sodium Pyrophosphate Decahydrate ($Na_4P_2O_7.10H_2O$) by XPS.* Surface Science Spectra, vol 9, 135-142(2004)
54. K. J. Gaskell, A. L. Asunkis, P. M. A. Sherwood. *Sodium Tripolyphosphate ($Na_5P_3O_{10}$) by XPS.* Surface Science Spectra, vol 9, 166-173 (2004).
55. V. Dalmoro, J. H. Z. dos Santos, E. Armelin, C. Alemán and D. Azambuja, Appl. Surf. Sci., 2013, 273, 758-768.
56. M. Jarlbring and D. E. Sandström, *Langmuir,* 2006, 22, 4787.
57. Y. Wang, *Nat. Mater.,* 2013, 12, 1144.
58. C. Jäger, *Magn. Reson. Chem.,* 2006, 44, 573.
59. M. B. Osman, S. Diallo-Garcia, V. Herledan, D. Brouri, T. Toshioka, J. Kubo, Y. Millot and G. Costentin, *J. Phys. Chem. C,* 2015, 119, 23008.
60. M. Nakamura, N. Hori, S. Namba, T. Toyama, N. Nishimiya and K. Yamashita, *Biomed. Mater.,* 2015, 10, 011001.
61. T. Ikoma, A. Yamazaki, S. Nakamura and M. Akao, *J. Mater. Sci. Lett.,* 1999, 18, 1225.
62. M. Nakamura, Y. Sekijima, S. Nakamura, T. Kobayashi, K. Niwa, K. Yamashita, *J. Biomed. Mater. Res.* 2006, 79A, 627-634.
63. M. Ueshima, S. Nakamura, M. Oghaki, K. Yamashita, *Solid State Ionics* 2002, 151, 29-34

The invention claimed is:

1. A permanently polarized hydroxyapatite, characterized in that its crystallinity is over 65% and its corresponding NMR $^{31}$P spectrum shows a unique peak at about 2.6 ppm corresponding to phosphate groups of hydroxyapatite, wherein said spectrum is carried out with solid hydroxyapatite using $H_3PO_4$ as a reference, and said permanently polarized hydroxyapatite has a surface capacitance which decreases less than 8% after 3 months.

2. A process for obtaining a permanently polarized hydroxyapatite according to claim 1, comprising the steps of:
   (a) obtaining sintered samples of hydroxyapatite and/or amorphous calcium phosphate at a temperature between 700° C. and 1200° C.;
   (b) applying a constant or variable DC voltage between 250 V and 2500 V or an equivalent electric field between 1.49 kV/cm and 15 kV/cm for at least 1 minute at a temperature between 900° C. and 1200° C. or applying an electrostatic discharge between 2500 V and 1500000 V or an equivalent electric field between 148.9 kV/cm and 8928 kV/cm for less than 10 minutes at a temperature between 900° C. and 1200° C.;

(c) cooling the samples while applying the constant or variable DC voltage or the equivalent electric field or cooling the samples while applying the electrostatic discharge or the equivalent electric field.

3. The process according to claim 2, wherein the sintered samples of hydroxyapatite obtained in step a) are selected from the group consisting of sintered samples of crystalline hydroxyapatite, sintered samples of amorphous hydroxyapatite and a mixture of said sintered samples.

4. The process according to claim 2, wherein the sintered samples obtained in step a) are sintered samples of crystalline hydroxyapatite and amorphous calcium phosphate.

5. A composition or material comprising the permanently polarized hydroxyapatite according to claim 1.

6. The composition or material according to claim 5, further comprising at least one of the followings: silicates; biocompatible polymers selected from polylactic acid (PLA), poly lactic-co-glycolic acid (PGLA), polyglycolide (PGA), polydioxanone (PDO), polyhydroxybutyrate (PHB), polysaccharides and proteins such as collagen; and metal ions.

7. A method of making a biomedical product, said method comprising incorporating the polarized hydroxyapatite according to claim 1 in biomedical products.

8. An electrode comprising the polarized hydroxyapatite according to claim 1.

9. A method for doping polymers comprising the step of applying the polarized hydroxyapatite according to claim 1.

10. A catalyst comprising the polarized hydroxyapatite according to claim 1.

11. The catalyst according to claim 10, wherein said catalyst is a photoelectrocatalyst or an electrocatalyst.

12. A method for adsorbing organic molecules comprising the step of applying the polarized hydroxyapatite according to claim 1.

13. A solid state battery comprising the polarized hydroxyapatite according to claim 1.

14. An energy harvesting chip comprising the polarized hydroxyapatite according to claim 1.

15. A composition or material comprising the permanently polarized hydroxyapatite prepared in accordance with claim 2.

16. The method according to claim 7, wherein said biomedical products are selected from the group consisting of cementum for teeth, bone, prosthesis, medical devices, drug-delivery, gene therapy and tissue regeneration.

17. The method according to claim 12, wherein said organic molecules are selected from the group consisting of carbohydrates, amino acids, lipids, DNA, RNA, ATP and biopolymers, wherein said biopolymers are selected from the group consisting of polylactic acid (PLA), poly lactic-co-glycolic acid (PGLA), polyhydroxybutyrate (PHB), polydioxanone (PDO), polysaccharides and proteins.

18. A method of making a biomedical product, said method comprising incorporating the permanently polarized hydroxyapatite prepared in accordance with claim 2 in biomedical products.

19. The permanently polarized hydroxyapatite of claim 1 having a residual electrostatic charge of at least about 12881 mC/cm2.

* * * * *